United States Patent [19]
Kubo et al.

[11] Patent Number: 5,500,427
[45] Date of Patent: Mar. 19, 1996

[54] CYCLIC COMPOUNDS AND THEIR USE

[75] Inventors: Keiji Kubo, Osaka; Yoshiyuki Inada; Takehiko Naka, both of Hyogo, all of Japan

[73] Assignee: Takeda Chemical Industries, Ltd., Osaka, Japan

[21] Appl. No.: 120,450

[22] Filed: Sep. 14, 1993

[30] Foreign Application Priority Data

Sep. 14, 1992 [JP] Japan .................... 4-245308
Dec. 24, 1992 [JP] Japan .................... 4-343855

[51] Int. Cl.$^6$ .................... C07D 413/12; A61K 31/41
[52] U.S. Cl. .................... 514/256; 514/313; 514/340; 514/342; 514/361; 514/364; 544/333; 546/162; 546/277; 548/129; 548/132
[58] Field of Search .................... 548/129, 132; 546/162, 277; 544/333; 514/756, 313, 361, 364, 340, 342

[56] References Cited

U.S. PATENT DOCUMENTS 5,243,054  9/1993  Naka .................... 548/132

FOREIGN PATENT DOCUMENTS 0434038  12/1990  European Pat. Off. .
0432737  6/1991   European Pat. Off. .
0475206  3/1992   European Pat. Off. .
0518033  4/1992   European Pat. Off. .
0520423  6/1992   European Pat. Off. .
0501892  9/1992   European Pat. Off. .

*Primary Examiner*—Robert Gerstl
*Attorney, Agent, or Firm*—Foley & Lardner

[57] ABSTRACT

The present invention relates to a compounds represented by the following formula or salts thereof.

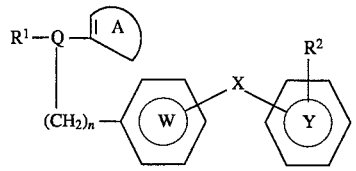

The above compounds have strong angiotensin II antagonistic action, antihypertensive action and action on central nervous system, which are useful for the treatment of circulatory diseases such as hypertension, heart diseases, cerebral apoplexy, nephritis, atherosclerosis or Alzheimer's disease and senile dementia, and for agents of improving cerebral function.

34 Claims, No Drawings

CYCLIC COMPOUNDS AND THEIR USE

FIELD OF THE INVENTION

The present invention relates to novel cyclic compounds having excellent pharmacological actions, their intermediates for the synthesis and salts thereof.

More specifically, the present invention relates to a compound represented by the general formula

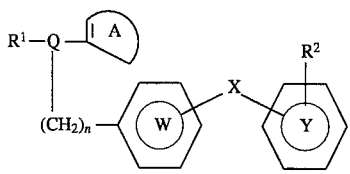

(I)

[wherein $R^1$ is an optionally substituted hydrocarbon residue which is optionally bound through a hetero-atom or an optionally substituted acyl group; $R^2$ is an optionally substituted 5–7 membered heterocyclic residue having, as a group capable of constituting the ring, carbonyl group, thiocarbonyl group, an optionally oxidized sulfur atom or a group convertible into them; Q is CH or N; X is a direct bond or a spacer having an atomic length of two or less between the ring Y and the ring W; W and Y are each an optionally substituted aromatic hydrocarbon residue optionally containing a hetero-atom or an optionally substituted heterocyclic residue; n is an integer of 1 or 2; the ring A is an optionally substituted 5–8 membered cyclic group, and two of the substituents are optionally bound to each other to form a ring] or a salt thereof, and to an angiotensin antagonistic agent containing same.

BACKGROUND OF THE INVENTION

The renin-angiotensin system is involved in the homeostatic function to control systemic blood pressure, the volume of body fluid, balance among the electrolytes, etc., associated with the aldosterone system. Relation between the renin-angiotensin system and hypertension has been clarified by the development of the inhibitors of angiotensin II (AII) converting enzyme (ACE) which produce angiotensin II having a strong vasoconstrictive action. Since angiotensin II constricts blood vessel to elevate blood pressure via the angiotensin II receptors on the cellular membranes, angiotensin II antagonists, like the ACE inhibitors, can be used for the therapy of hypertension caused by angiotensin II. It has been reported that a number of angiotensin II analogues such as saralasin, [$Sar^1$, $Ile^8$] AII and the like possess potent angiotensin II antagonism. It has, however, been reported that, peptide antagonists shows a short term action by parenteral administration and they are ineffective by oral administration [M. A. Ondetti and D. W. Cushman, Annual Reports in Medicinal Chemistry, 13, 82–91 (1978)].

On the other hand, for solving the problems observed in these peptide angiotensin II antagonists, studies on nonpeptide angiotensin II antagonists have been developed. In the earliest studies in this field, imidazole derivatives having angiotensin II antagonism have been disclosed in Japanese patent unexamined publication No. 56-71073 (JPA 56-71073), JPA 56-71074, JPA 57-98270 and JPA 58-157768, U.S. Pat. No. 4,355,040 and 4,340,598, etc. Later, improved imidazole derivatives are disclosed in EP-0253310, EP-0291969, EP-0324377, EP-403158, WO-9100277, JPA 63-23868 and JPA H-117876; pyrrole, pyrazole and triazole derivatives in EP-0323841, EP-0409332 and JPA 1-287071; benzimidazole derivatives in U.S. Pat. No. 4,880,804, EP-0392317, EP-0399732, EP-0400835 and JPA 3-63264; azaindene derivatives in EP-0399731; pyrimidone derivatives in EP-0407342; pyridine derivatives in EP-0475206 and EP-0499415; and quinazolinone derivatives in EP-0411766; as angiotensin II antagonists.

However, in order to become a practically useful therapeutic agent, angiotensin II antagonists are required to have a strong and long acting angiotensin II antagonistic and hypotensive action by oral administration. As shown in so far known literature references, the preferable structural feature as a strong angiotensin II antagonist is considered to have an acid group, for example, tetrazole group or carboxyl group on the biphenyl side chain, especially tetrazole group as most preferable one and clinical test of compounds having the tetrazole group for anti-hypertension agents is conducted [Y. Christen, B. Waeber, J. Nussberger, R. J. Lee, P. B. M. W. M. Timmermans, and H. R. Brunner, Am. J. Hypertens., 4, 350S (1991)]. However, compounds having tetrazole ring and azide compounds to be used for synthesizing them have been known as involving a danger of explosion, which becomes a serious problem to the large scale preparation and industrial production.

The present inventors considered that compounds acting to control renin-angiotensin system as well as being clinically useful for the treatment of circulatory diseases such as hypertension, cardiopathy (hypercardia, heart failure, cardiac infarction, etc.), cerebral apoplexy, and improving cerebral function, are required to have an angiotensin II receptor antagonistic activity and also have a strong and long active angiotensin II antagonistic activity and hypotensive action by oral administration, and they have made extensive and intensive studies.

As a result, the present inventors have found a novel cyclic compounds having a potent angiotensin II receptor antagonistic activity as well as a long-acting and strong AII antagonistic and anti-hypertensive actions by oral administration. The present inventors have further developed studies to accomplish the present invention.

SUMMARY OF THE INVENTION

The present invention is to provide the novel cyclic compounds having a heterocyclic residue substitutable for a strong acid group such as tetrazole or carboxylic group, which has a strong angiotensin II antagonistic action and antihypertensive action and which can be put to practical use satisfactorily as a medicinal agent.

More specifically, the present invention relates to
(1) Compounds represented by the formula (I):

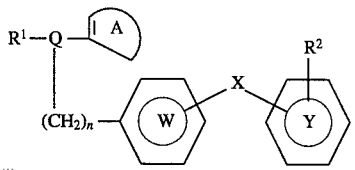

(I)

[wherein $R^1$ is an optionally substituted hydrocarbon residue which is optionally bound through a hetero-atom and or an optionally substituted acyl group; $R^2$ is an optionally substituted 5–7 membered heterocyclic residue having, as a group capable of constituting the ring, carbonyl group, thiocarbonyl group, an optionally oxidized sulfur atom or a group convertible into them; Q is CH or N; X is a direct bond or a spacer having an atomic length of two or less between the ring Y and the ring W; rings W and Y are each an optionally substituted aromatic hydrocarbon residue optionally containing a he,ere-atom or an optionally substituted heterocyclic residue; n is an integer of 1 or 2; the ring A is an optionally substituted 5–8 membered cyclic group, and two of the substituents are optionally bound to each other to form a ring] or a salt thereof, preferably, (2) a compound of the above general formula (I), wherein the atom adjacent to the position where the ring A is bound to Q is a carbon atom substituted with a group capable of liberating proton or a group convertible thereinto in a living body, or a salt thereof, and an angiotensin II antagonistic agent containing a compound of (1) or a salt thereof.

Referring to the above-mentioned general formula (I), examples of the hydrocarbon residue represented by $R^1$ include alkyl, alkenyl, alkynyl, cycloalkyl, cycloalkenyl, aryl and aralkyl groups. Among them, alkyl, alkenyl and cycloalkyl groups are preferable. The hydrocarbon residue may be bound to Q through a hetero atom, or may be further substituted with a substituent such as an optionally bound through the hetero atom and/or optionally substituted hydrocarbon residue represent by $R^1$.

The alkyl group represented by $R^1$ is a straight-chain or branched alkyl group having 1 to about 8 carbon atoms ($C_{1-8}$), as exemplified by methyl, ethyl, propyl, isopropyl, butyl, isobutyl, sec-butyl, t-butyl, pentyl, i-pentyl, hexyl, heptyl or octyl.

The alkenyl group represented by $R^1$ is a straight-chain or branched alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight-chain or branched alkynyl group having 2 to about 8 carbon atoms, as exemplified by ethynyl, 2-propinyl, 2-butynyl, 2-pentynyl or 2-octynyl.

The cycloalkyl group represented by $R^1$ is a cycloalkyl group having 3 to about 6 carbon atoms, as exemplified by cyclopropyl, cyclobutyl, cyclopentyl or cyclohexyl.

The cycloalkenyl group represented by $R^1$ is a cycloalkenyl group having 3 to 6 carbon atoms, as exemplified cyclopropenyl, cyclopentenyl or cyclohexenyl.

The above-mentioned alkyl, alkenyl, alkynyl or cycloalkyl or cycloalkenyl group may optionally be substituted with hydroxyl group, an optionally substituted amino group (e.g. amino, N—$C_{1-4}$ alkylamino or N,N-di-$C_{1-4}$ alkylamino), halogen, $C_{1-4}$ alkoxy group, or $C_{1-4}$ alkylthio group.

The aralkyl group represented by $R^1$ is, for example, a phenyl-$C_{1-4}$ alkyl such as benzyl or phenethyl, and the aryl group represented by $R^1$ is, for example, phenyl. The aralkyl or aryl group may be optionally substituted with, on an optional position of its aryl ring, for example, halogen (e.g. F, Cl or Br), nitro, an optionally substituted amino group (e.g. amino, N—$C_{1-4}$ alkylamino or N,N-di-$C_{1-4}$ alkylamino), $C_{1-4}$ alkoxy (e.g. methoxy or ethoxy), $C_{1-4}$ alkylthio (e.g. methylthio or ethylthio) or $C_{1-4}$ alkyl (e.g. methyl or ethyl).

Among the above-exemplified groups represented by $R^1$, optionally substituted alkyl or alkenyl groups (e.g. $C_{1-5}$ alkyl or $C_{2-5}$ alkenyl group optionally substituted with hydroxyl group, amino group, halogen or $C_{1-4}$ alkoxy group) are preferable.

$R^1$ may optionally bound through a hetero-atom (e.g. nitrogen [N($R^9$) ($R^9$ stands for hydrogen or optionally substituted lower ($C_{1-4}$) alkyl)], oxygen or sulfur [—S(O)m—(m denotes an integer of 0 to 2)], etc.), and, among them, optionally substituted alkyl or alkenyl group optionally bound through a hetero-atom (e.g. methyl, ethyl, propyl, isopropyl, acethyl, methylamino, ethylamino, propylamino, propenylamino, isopropylamino, allylamino, butyrylamino, isobutyrylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, sec-butylthio, t-butylthio, 2-butenylthio, 3-butenylthio, isobutenylthio, pentylthio, isopentylthio, hexylthio, ethoxymethyl, methoxyethyl, isopropoxymethyl, t-buthoxyethyl, methylthiomethyl, ethylthioethyl, t-buthylthioethyl, etc.) are preferable.

Examples of the acyl group represented by $R^1$ include alkanoyl, alkenoyl, alkynoyl, cycloalkylcarbonyl, aralkynoyl and benzoyl groups. Among them, alkanoyl, alkenoyl and cycloalkylcarbonyl groups are preferable. The acyl group may be further substituted with, for example, an optionally substituted hydrocarbon residue which is optionally bound through a hetero-atom represented by above-mentioned $R^1$.

The alkanoyl group represented by $R^1$ is a straight-chain or branched alkanoyl group having 1 to about 8 carbon atoms, as exemplified by formyl, acetyl, propionyl, butyryl, isobutyryl, valeryl, isovaleryl, hexanoyl, heptanoyl or octanoyl.

The alkenoyl group represented by $R^1$ is a straight-chain or branched alkenoyl group having 3 to about 8 carbon atoms, as exemplified by acryloyl, methacryloyl, crotonoyl, 2-butenoyl, 3-butenoyl, 2-pentenoyl, 3-pentenoyl, 2-hexenoyl, 2-heptenoyl or 2-octenoyl.

The alkynoyl group represented by $R^1$ is a straight-chain or branched alkynoyl group having 3 to about 8 carbon atoms, as exemplified by propionoyl, 2-butynoyl, 2-pentynoyl or 2-octynoyl.

The cycloalkylcarbonyl group represented by $R^1$ is a cycloalkylcarbonyl group having 4 to about 7 carbon atoms, as exemplified by cyclopropylcarbonyl, cyclobutylcarbonyl, cyclopentylcarbonyl or cyclohexylcarbonyl.

The above-mentioned alkanoyl, alkenoyl, alkynoyl or cycloalkylcarbonyl group may optionally be substituted with, for example, hydroxyl group, an optionally substituted amino group [e.g. amino, N—$C_{1-4}$ alkylamino, or N,N-di-$C_{1-4}$ alkylamino], halogen, $C_{1-4}$ alkoxy group or $C_{1-4}$ alkylthio group.

Examples of optionally substituted aromatic hydrocarbon residue or heterocyclic residue optionally containing a hetero-atom, which are represented by the ring Y and the ring W, include aromatic hydrocarbon residues such as phenyl, and 4- to 7-membered monocyclic or condensed heterocyclic residues containing one or more of N, S and O, for example, pyridyl, pyrimidinyl, pyridazinyl, pyrazinyl, thienyl, furyl, pyrrolyl, imidazolyl, pyrazolyl, isothiazolyl, isoxazolyl, isobenzofuranyl, benzofuranyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl and pteridinyl. Among them, phenyl is a preferable one.

The above-mentioned ring Y has a substituent represented by $R^2$ as exemplified by an optionally substituted 5- to 7-membered (preferably 5- to 6-membered) monocyclic heterocyclic residue containing one or more of N, S and O (preferably N-containing heterocyclic residue having hydrogen atom capable of being deprotonated) or a group convertible thereinto. Examples of the group represented by $R^2$ are shown below:

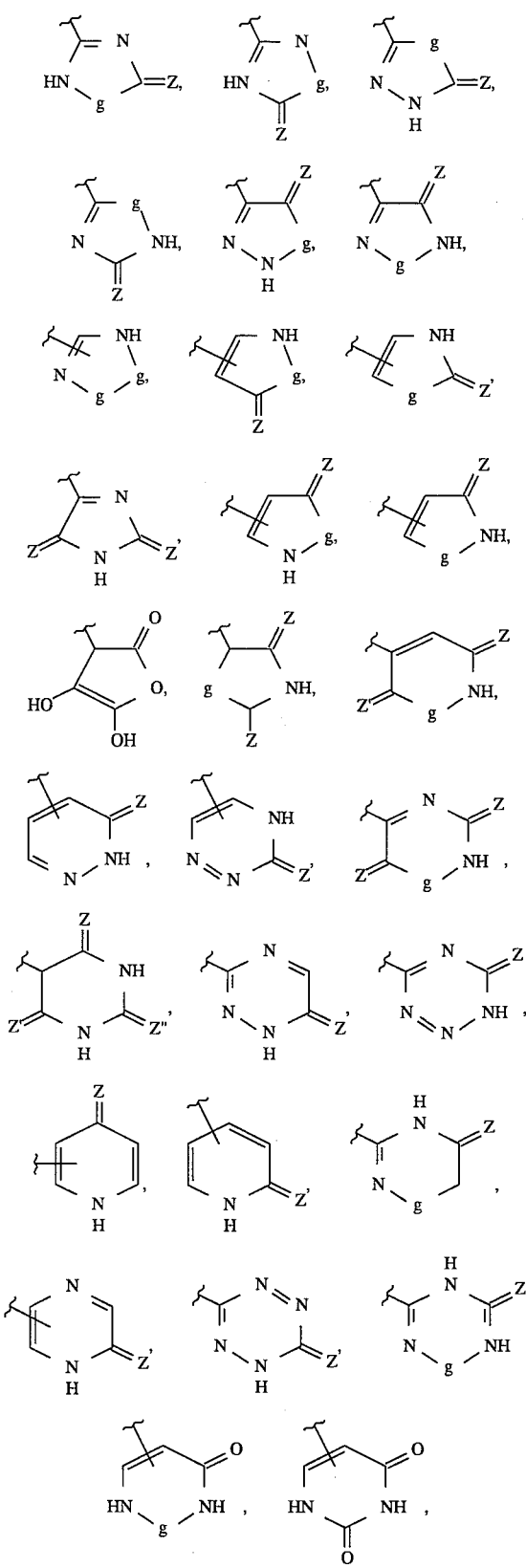

-continued

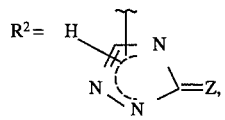

[In the above formula, $$g = -CH_2-, \quad -NR^9-, \quad -O- \text{ or } -\underset{\underset{(O)_m}{|}}{S}-;$$

$>=Z, \quad >=Z' \text{ and } >=Z''$ respectively stand for a carbonyl group, a thiocarbonyl group or an optionally oxidized sulfur atom (e.g. S, S(O), and $S(O)_2$) (preferably a carbonyl or thiocarbonyl group, more preferably a carbonyl group), m denotes an integer of 0, 1 or 2, and $R^9$ stands for hydrogen or an optionally substituted lower alkyl group].

And, besides the case of carbon-carbon linkage as in the above formulas, a group represented by $R^2$ may optionally be bound to an optionally substituted aromatic hydrocarbon optionally containing a hetero-atom or heterocyclic residue, which is represented by Y, in the case of g=—NH— in the above formulas, through one of the plural number of existing nitrogen atoms.

For example, when $$R^2 = H \begin{array}{c} \text{\scriptsize (structure)} \end{array}$$

specifically

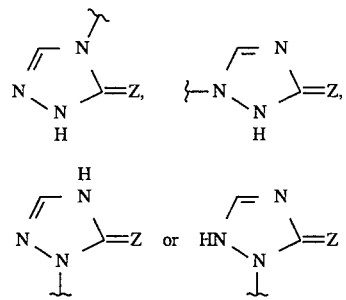

represents that group. Other examples of $R^2$ bonded through the nitrogen atom include

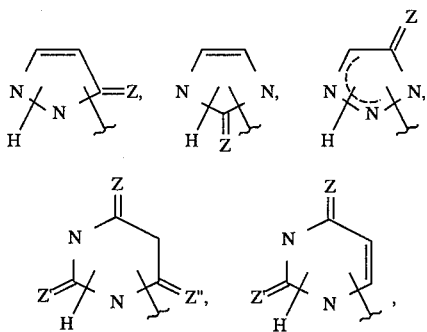

-continued

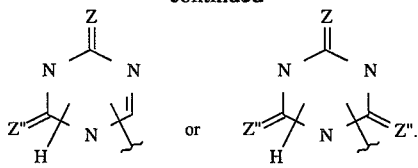

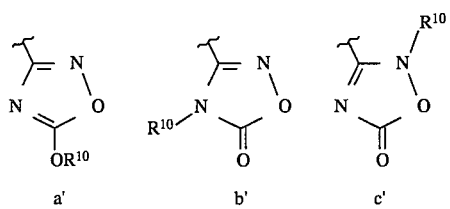

a'  b'  c'

Preferable groups represented by $R^2$ are, like 2,5-dihydro-5-oxo-1,2,4-oxadiazol-3-yl or 2,5-dihydro-5-oxo-1,2,4-thiadiazol-3-yl, those having —NH— or —OH group as proton-donor and carbonyl group, thiocarbonyl group or sulfinyl group as proton acceptor simultaneously. And, while the heterocyclic residue represented by $R^2$ may optionally form a condensed ring by the linkage of substituents on the ring, preferable ones are 5- to 6-membered heterocyclic residues, more preferably 5-membered ones. Among others, as $R^2$, groups of the formula

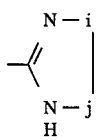

[wherein i is —O— or —S—, j is C=O, C=S or —S(O)$_m$—, and m is of the same meaning as defined above] (especially, 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl) are preferable. In case where the ring Y is, for example, phenyl, $R^2$ may be substituted at any of ortho-, meta- or para-position, preferably ortho-position.

And, while the above-mentioned heterocyclic residue ($R^2$) can exist in tautomeric forms as shown below, for example, three tautomers, a, b and c,

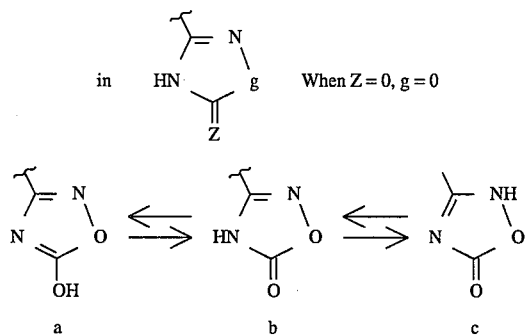

the heterocyclic residue represented by the formula

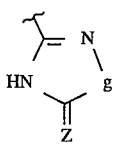

includes all of the above-mentioned tautomers a, b and c.

And, the above-mentioned a group convertible thereinto for $R^2$ may be a group capable of easily converting into the heterocyclic group mentioned above either chemically or biologically under physiological conditions. For example, such substitutes for $R^2$ may be mentioned, as shown below:

Examples of the group represented by $R^{10}$ include groups represented by the formula —CH($R^4$)—OCOR$^5$ [wherein $R^4$ stands for hydrogen, $C_{1-6}$ straight-chain or branched alkyl group (e.g. methyl, ethyl, n-propyl, isopropyl, t-butyl, n-pentyl, isopentyl, or neopentyl), $C_{2-6}$ straight-chain or branched alkenyl group or $C_{3-8}$ cycloalkyl group (e.g. cyclopentyl, cyclohexyl or cycloheptyl); $R^5$ stands for $C_{1-6}$ straight-chain or branched alkyl group (e.g. methyl, ethyl, n-propyl, isopropyl, n-butyl, isobutyl, sec-butyl, t-butyl, n-pentyl, isopentyl or neopentyl), $C_{2-6}$ straight-chain or branched alkenyl group, $C_{3-8}$ cycloalkyl group (e.g. cyclopentyl, cyclohexyl or cycloheptyl), $C_{1-3}$ alkyl group substituted with $C_{3-8}$ cycloalkyl group (e.g. cyclopentyl, cyclohexyl or cycloheptyl) or an optionally substituted aryl group such as phenyl (e.g. benzyl, p-chlorobenzyl, phenethyl, cyclopentylmethyl or cyclohexylmethyl), $C_{2-3}$ alkenyl group substituted with $C_{3-8}$ cycloalkyl or an optionally substituted aryl group such as phenyl (e.g. a group having alkenyl moiety such as vinyl (e.g. cinnamyl), propenyl, allyl or isopropenyl), an optionally substituted aryl group such as phenyl (e.g. phenyl, p-tolyl or naphthyl), $C_{1-6}$ straight-chain or branched alkoxy group (e.g. methoxy, ethoxy, n-propoxy, isopropoxy, n-butoxy, isobutoxy, sec-butoxy, t-butoxy, n-pentyloxy, isopentyloxy or neopentyloxy), $C_{2-8}$ straight-chain or branched alkenyloxy group (e.g. allyloxy or isobutenyloxy), $C_{3-8}$ cycloalkyloxy group (e.g. cyclopentyloxy, cyclohexyloxy or cycloheptyloxy), $C_{1-3}$ alkoxy group substituted with $C_{3-8}$ cycloalkyl (e.g. cyclopentyl, cyclohexyl or cycloheptyl) or with an optionally substituted aryl group such as phenyl (e.g. a group having alkoxy moiety such as methoxy, ethoxy, n-propoxy or isopropoxy) e.g. benzyloxy, phenethyloxy, cyclopentylmethyloxy or cyclohexylmethyloxy), $C_{2-3}$ alkenyloxy group substituted with $C_{3-8}$ cycloalkyl (e.g. cyclopentyl, cyclohexyl or cycloheptyl) or with an optionally substituted aryl group such as phenyl (e.g. a group having alkenyloxy moiety such as vinyloxy (e.g. cinnamyloxy), propenyloxy, allyloxy or isopropenyloxy), an aryloxy group including optionally substituted phenoxy (e.g. phenoxy, p-nitrophenoxy or napthoxy)], and an optionally substituted alkyl (e.g. $C_{1-4}$ alkyl) or acyl (e.g. $C_{2-5}$ alkanoyl or optionally substituted benzoyl). Examples of $R^{10}$ include methyl, ethyl, propyl, t-butyl, methoxymethyl, triphenylmethyl, cyanoethyl, acetyl, propionyl, pivaloyloxymethyl, 1-(cyclohexyloxycarbonyloxy)ethyl, (5-methyl-2-oxo-1,3-dioxolen-4-yl)methyl, acetoxymethyl, propionyloxymethyl, n-butyryloxymethyl, isobutyryloxymethyl, 1-(ethoxycarbonyloxy)ethyl, 1-(acetyloxy)ethyl, 1-(isobutyryloxy)ethyl, cyclohexylcarbonyloxymethyl, benzoyloxymethyl, cinnamylcarboxylmethyl and cyclopentylcarbonyloxymethyl. Such groups may include substituents which are capable of easily converting into the initial heterocyclic residue represented by the formula

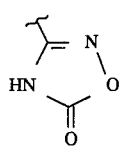

either chemically or biologically i.e. under physiological conditions (for example, in vivo reaction such as oxidation, reduction or hydrolysis catalyzed by in vivo enzymes) (what is called prodrug).

As the above-mentioned tautomers of heterocyclic residues (a, b and c) and the heterocyclic residue (a', b' and c') substituted with $R^{10}$ are included in the heterocyclic residues represented by the substituent $R^2$ in the present invention, so the tautomers and their substituted compounds of various heterocyclic residues described in the foregoing are, as a matter of course, included in the substituent $R^2$ in the present invention. And, the substituent $R^2$ may have further substituents other than those represented by $R^{10}$ described above, as exemplified by an optionally substituted alkyl group (e.g. methyl and triphenylmethyl), halogen (e.g. F, Cl and Br), nitro, cyano, $C_{1-4}$ alkoxy, and an optionally substituted amino group (e.g. amino, methylamino and dimethylamino), among others.

The ring W includes optionally substituted aromatic hydrocarbon residue and heterocyclic residue optionally containing one or more of N, O and S atom, as exemplified by phenyl, pyridyl, pyrazinyl, pyridazinyl, pyrazinyl, thienyl, furyl, pyrrolyl, imidazolyl, pyrazolyl, isothiazolyl and isoxazolyl (preferably phenyl).

And, the aromatic hydrocarbon residue and the heterocyclic residue which may optionally contain one or more of N, O and S atom, represented by the ring W and the ring Y, may optionally have substituents as exemplified by halogen (e.g. F, Cl and Br), nitro, cyano, $C_{1-4}$ alkoxy, an optionally substituted amino group (e.g. amino, methylamino and dimethylamino).

X shows that the adjacent ring W (e.g. phenylene group) is bound to the ring (e.g. phenyl group) directly or through a spacer with an atomic chain of 2 or less (preferably direct bond). As the spacer, any one can be exemplified, so long as it is a divalent chain in which the number of atoms constituting the straight chain is 1 or 2, and it may have a side chain, more specifically, $C_{1-4}$ alkylene, —CO—, —O—, —S—, —NH—, —CO—NH—, —O—CH$_2$—, —S—CH$_2$— and —CH=CH—.

The symbol n denotes an integer of 1 or 2 (preferably 1).

Among the compounds shown by $R^2$, W, X, Y and n described above represented by the formula

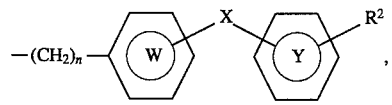

those represented by the formula

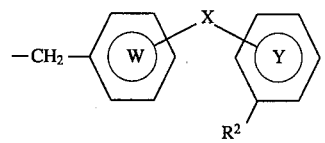

for example,

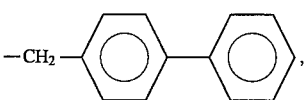

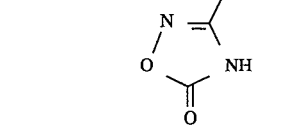

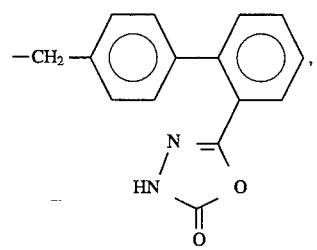

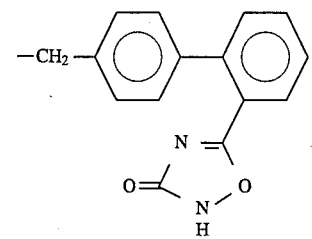

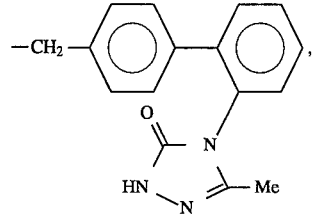

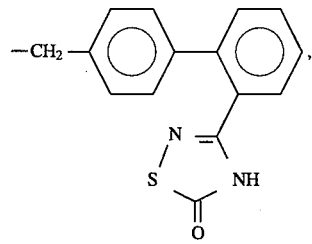

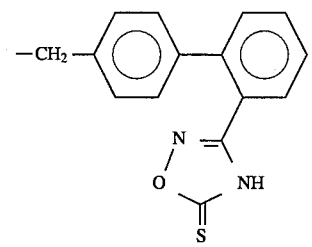

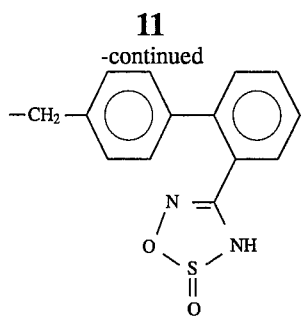

are preferable.

The ring A is a cyclic hydrocarbon residue or heterocyclic ring having at least one unsaturated bond. Typical examples of these cyclic compounds are specifically shown as below.

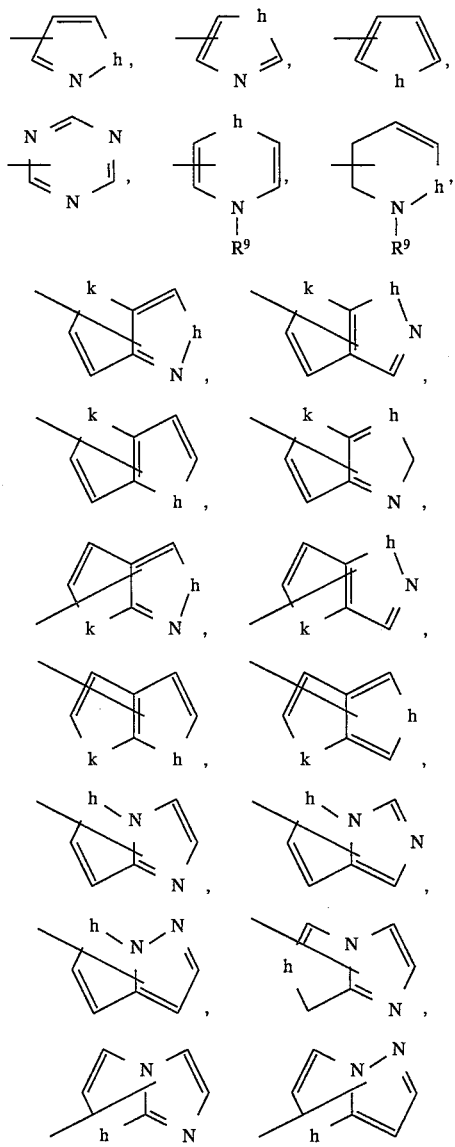

[wherein h and k independently stand for —CH2—, C=O, C=S, S(O)$_m$, N—R$^9$, —O—, —CH=CH—, —N=CH—, —CH=N—, —CO—N(R$^9$)—, —N(R$^9$)—CO—, —N=N—, —N(R$^9$)—CO—N(R$^9$)—, —CH=CH—CO—; R$^{9,}$ stands for H or an optionally substituted lower (C$_{1-4}$) alkyl group; m and R$^9$ are of the same meaning as defined above].

These are mere examples, and the present invention should not be limited thereto.

The above-mentioned ring A may optionally be substituted with, besides the atom represented by Q, a group represented by R$^3$, for example, a group capable of liberating proton or a group convertible thereinto in vivo. The substitution position of R$^3$ is preferably the position adjacent to the carbon atom to which Q is bonded.

Examples of the group R$^3$ capable of liberating proton or a group convertible thereinto in vivo include optionally esterified or amidated carboxyl, tetrazolyl, trifluoromethane-sulfonic acid amide (—NHSO$_2$CF$_3$), phosphoric acid and sulfonic acid groups. These groups may optionally be protected with an optionally substituted lower alkyl group or acyl group, and may be any one if only they are capable of forming anion under biological or physiological conditions (for example, in vivo reaction such as oxidation, reduction or hydrolysis by in vivo enzymes).

Examples of optionally esterified or amidated carboxyl represented by R$^3$ include groups represented by the formula —CO—D [wherein D stands for hydroxyl group, optionally substituted amino (e.g. amino, N—C$_{1-4}$ alkylamino, and N,N-di-C$_{1-4}$ alkylamino) or optionally substituted alkoxy {e.g. C$_{1-6}$ alkoxy group, whose alkyl moiety is optionally substituted with hydroxyl group, optionally substituted amino (e.g. amino, dimethylamino, diethylamino, piperidino and morpholino), halogen, C$_{1-6}$ alkoxy, C$_{1-6}$ alkylthio or optionally substituted dioxolenyl (e.g. 5-methyl-2-oxo-1,3-dioxolen-4-yl), or group represented by the formula —O—CH(R$^4$)—OCOR$_5$ [wherein R$^4$ stands for hydrogen, C$_{1-6}$ straight-chain or branched alkyl group (e.g. methyl, ethyl, n-propyl, isopropyl, n-butyl, isobutyl, t-butyl, n-pentyl, isopentyl and neopentyl), C$_{2-6}$ straight-chain or branched alkenyl group or C$_{3-8}$ cycloalkyl group (e.g. cyclopentyl, cyclohexyl and cycloheptyl), and R$^5$ stands for C$_{1-6}$ straight-chain or branched alkyl group (e.g. methyl, ethyl, n-propyl, isopropyl, n-butyl, isobutyl, sec-butyl, t-butyl, n-pentyl, isopentyl and neopentyl), C$_{2-6}$ straight-chain or branched alkenyl group, C$_{3-8}$ cycloalkyl group (e.g. cyclopentyl, cyclohexyl and cycloheptyl), C$_{1-3}$ alkyl group substituted with C$_{3-8}$ cycloalkyl (e.g. cyclopentyl, cyclohexyl and cycloheptyl) or an optionally substituted aryl group such as phenyl (e.g. benzyl, p-chlorobenzyl, phenethyl, cyclopentylmethyl and cyclohexylmethyl), C$_{2-3}$ alkenyl group optionally substituted with C$_{3-8}$ cycloalkyl or an optionally substituted aryl group such as phenyl (e.g. cinnamyl, etc. having alkenyl moiety such as vinyl, propenyl, ally, and isopropenyl), an aryl group such as optionally substituted phenyl (e.g. phenyl, p-tolyl, naphthyl), C$_{1-6}$ straight-chain or branched alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), C$_{2-8}$ straight-chain or branched alkenyloxy group (e.g. allyloxy and isobutenyloxy), C$_{3-8}$ cycloalkyloxy group (e.g. cyclopentyloxy, cyclohexyloxy and cycloheptyloxy), C$_{1-3}$ alkoxy group substituted with C$_{3-8}$ cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), C$_{2-3}$ alkenyloxy group substituted with C$_{3-8}$ cycloalkyl (e.g. cyclopentyl, cyclohexyl and cycloheptyl) or an aryl group such as optionally substituted phenyl (e.g. cinnamyloxy having alkenyloxy moiety such as vinyloxy, propenyloxy, allyloxy, isopropenyloxy) and an aryloxy group such as optionally substituted phenoxy (e.g. phenoxy, p-nitrophenoxy and naphthoxy)]}]. And, examples of the substituent represented by $R^3$ may also include a group capable of liberating proton or a group convertible thereinto in vivo (e.g. tetrazolyl, trifluoromethanesulfonic acid amide, phosphoric acid or sulfonic acid optionally protected with alkyl (e.g. $C_{1-4}$ alkyl) or acyl (e.g. $C_{2-5}$ alkanoyl and optionally substituted benzoyl).

Examples of the substituent $R^3$ include —COOH— and a salt thereof, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolen-4-yl)methoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl and cyclopentylcarbonyloxymethoxycarbonyl. As such groups as above, mention is made of any one capable of liberating proton or a group convertible thereinto under biological or physiological conditions (e.g. in vivo reaction such as oxidation, reduction or hydrolysis catalyzed by in vivo enzymes). $R^3$ may be carboxyl group or a prodrug thereof.

$R^3$ may also be groups convertible into anion in vivo, for example, biologically or chemically.

And, a compound, in which $R^3$ is a group capable of liberating proton or a group convertible thereinto (e.g. optionally protected carboxyl group, tetrazolyl group, carbaldehyde group and hydroxymethyl group; and cyano group) chemically (e.g. oxidation, reduction or hydrolysis), is useful as synthetic intermediate.

Among the groups described as $R^3$, preferable ones include carboxyl, esterified carboxyl (e.g. methyl ester, ethyl ester or an ester formed by bonding of a group represented by the above-mentioned formula —O— CH($R^4$)—OCOR$^5$ to carbonyl) and optionally protected tetrazolyl, carbaldehyde and hydroxymethyl.

The ring A may optionally have, besides the groups represented by Q and $R^3$, further substituents, as exemplified by halogen (e.g. F, Cl and Br), nitro, cyano, an optionally substituted amino group [e.g. amino, N—$C_{1-4}$ alkylamino (e.g. methylamino), N,N-di-$C_{1-4}$ alkylamino (e.g. dimethylamino), N-arylamino (e.g. phenylamino), alicyclic amino (e.g. morpholino, piperidino, piperazino and N-phenylpiperazino)], groups represented by the formula —U—$R^6$ [wherein U stands for a bond, —O—, —S— or —CO— and $R^6$ stands for hydrogen, an optionally substituted lower alkyl group (e.g. $C_{1-4}$ alkyl optionally substituted with hydroxyl group, an optionally substituted amino group (e.g. amino), halogen, nitro, cyano or $C_{1-4}$ alkoxy group], groups represented by the formula —(CH$_2$),—CO—D' [wherein D' stands for hydrogen, hydroxyl group, optionally substituted amino (e.g. amino, N—$C_{1-4}$ alkylamino and N-N-di-$C_{1-4}$ alkylamino), or optionally substituted alkoxy (e.g. $C_{1-6}$ alkoxy group whose alkyl moiety is optionally substituted with hydroxyl group, optionally substituted amino (e.g. amino, dimethylamino, diethylamino, piperidino and morpholino and morpholino), halogen, $C_{1-6}$ alkoxy, $C_{1-6}$ alkylthio, or optionally substituted dioxolenyl (e.g. 5-methyl-2-oxo-1,3-dioxolen-4-yl) or groups represented by the formula —OCH($R^7$)OCOR$^8$ [wherein $R^7$ stands for hydrogen, $C_{1-6}$ straight-chain or branched alkyl group (e.g. methyl, ethyl n-propyl, isopropyl, n-butyl, isobutyl, t-butyl, n-pentyl, isopentyl and neopentyl) or $C_{5-7}$ cycloalkyl group (cyclopentyl cyclohexyl and cycloheptyl), and $R^8$ stands for $C_{1-6}$ straight-chain or branched alkyl group (e.g. methyl, ethyl, n-propyl, isopropyl, n-butyl, isobutyl, sec-butyl, t-butyl, n-pentyl, isopentyl and neopentyl), $C_{2-8}$ alkenyl group (e.g. vinyl, propenyl, allyl and isopropenyl), $C_{5-7}$ cycloalkyl group (e.g. cyclopentyl cyclohexyl and cycloheptyl), $C_{1-3}$ alkyl group substituted with $C_{5-7}$ cycloalkyl group (e.g. cyclopentyl, cyclohexyl and cycloheptyl) or an aryl group such as phenyl (e.g. benzyl, p-chlorobenzyl, phenethyl, cyclopentylmethyl and cyclohexylmethyl), $C_{2-3}$ alkenyl group substituted with $C_{5-7}$ cycloalkyl (e.g. cyclopentyl, cyclohexyl and cycloheptyl) or an aryl group such as phenyl (e.g. cinnamyl having alkenyl moiety such as vinyl, propenyl, allyl or isopropenyl), an optionally substituted aryl group such as phenyl (e.g. phenyl, p-tolyl and naphthyl), $C_{1-6}$ straight-chain or branched alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), $C_{2-8}$ straight-chain or branched alkenyloxy group (e.g. allyloxy and isobutenyloxy), $C_{1-7}$ cycloalkyloxy group (e.g. cyclopentyloxy, cyclohexyloxy and cycloheptyloxy), $C_{1-3}$ alkoxy group substituted with $C_{5-7}$ cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), $C_{2-3}$ alkenyloxy group, substituted with $C_{5-7}$ cycloalkyl (e.g. cyclopentyl, cyclohexyl and cycloheptyl) or an optionally substituted aryl group such as phenyl (e.g. cinnamyloxy having alkenyloxy moiety such as vinyloxy, propenyloxy, allyloxy and isopropenyloxy)) and an aryloxy group such as optionally substituted phenoxy (e.g. phenoxy, p-nitrophenoxy and naphthoxy)], and l denotes 0 or 1] or tetrazolyl, trifluoromethanesulfonic acid amide, phosphoric acid or sulfonic acid, each optionally protected with alkyl (e.g. $C_{1-4}$ alkyl) or acyl (e.g. $C_{2-5}$ alkanoyl and optionally substituted benzoyl).

One or two of these substituents may optionally be substituted simultaneously on optional positions of the ring. When two or more of these substituents exist, (preferably the case where two substituents exist in two ring-forming groups adjacent to each other), they may be bonded to each other to form a 5- to 8-membered aromatic hydrocarbon residue or heterocyclic residue (preferably aromatic ring such as phenyl), taken together with the two ring-forming atoms. These rings may further substituted with any of the above-described substituents.

Among the heterocyclic rings as ring A, the following, for example, are preferable:

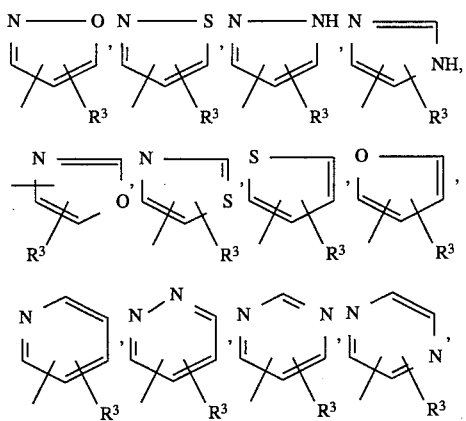

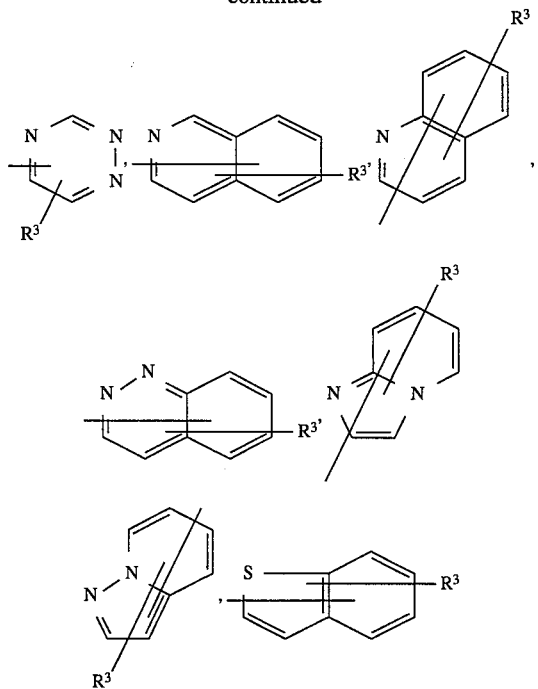

(preferably, thiophene, pyrazole, pyridine, pyrimidine, pyrazine, quinoline, isoquinoline (especially pyridine, pyrimidine) skeleton) [[wherein $R^3$ is of the same meaning as defined above].

Among the compounds represented by the formula (I), preferable ones are represented by the formula

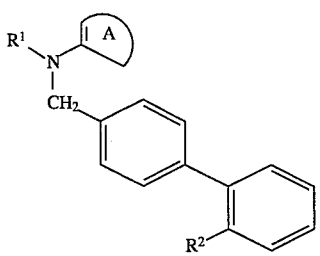

(I$^a$)

wherein $R^1$ stands for an optionally substituted $C_{1-6}$ alkyl group which may be bound through a hetero-atom (e.g. O, N(H), and S) (preferably $C_{2-4}$ alkyl group), $R^2$ stands for oxo- or thioxo-substituted oxadiazolyl or thiadiazolyl optionally protected with an optionally substituted $C_{1-4}$ alkyl group (e.g. methyl, triphenylmethyl, methoxymethyl, acetyloxymethyl, methoxycarbonyloxymethyl, cyclohexyloxycarbonyloxyethyl, and pivaloyloxymethyl) or an acyl group (e.g. $C_{2-5}$ alkanoyl and benzoyl), and examples of the cyclic group represented by the ring A include those shown by the following formula,

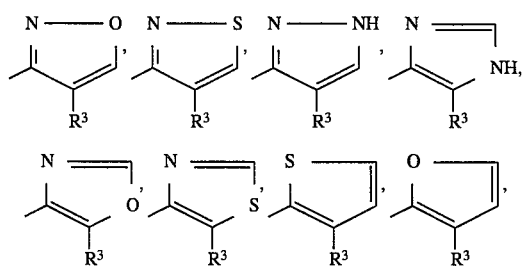

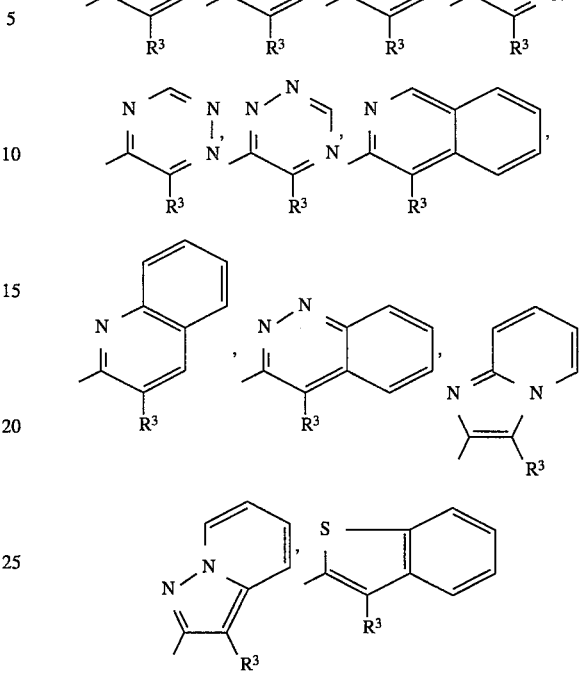

in the above formula, $R^3$ stands for groups represented by the formula —CO—D" [wherein D" stands for hydroxyl group, amino, N—$C_{1-4}$ alkylamino group, N,N-di-$C_{1-4}$ alkylamino group or $C_{1-4}$ alkoxy group whose alkyl moiety may optionally substituted with hydroxyl group, amino, halogen, $C_{2-6}$ alkanoyloxy group (e.g. acetyloxy and pivaloyloxy), 1-$C_{1-6}$ alkoxycarbonyl group (e.g. methoxycarbonyloxy, ethoxycarbonyloxy and cyclohexyloxycarbonyloxy) or $C_{1-4}$ alkoxy group] or tetrazolyl optionally protected with $C_{1-4}$ alkyl group or an acyl group (e.g. $C_{2-5}$ alkanoyl group and benzoyl)].

And, compounds represented by the above-mentioned formula (Ia) wherein $R^2$ stands for N-hydroxycarbamimidoyl (—C(=N—OH)—NH$_2$) are useful intermediates for synthesizing compounds of the formula (Ia) wherein $R^2$ is oxo- or thioxo substituted oxadiazolyl or thiadiazolyl.

Production Method

The compounds of the general formula (I) can be produced by, for example, methods as illustrated below.

Reaction (a)

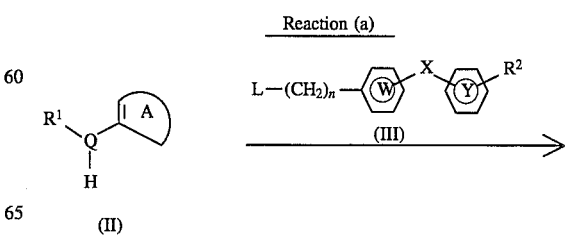

-continued
Reaction (a)

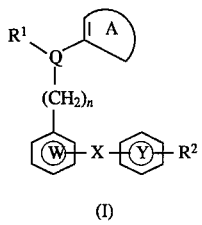

(I)

[wherein A, $R^1$, $R^2$, Q, W, x, Y and n are of the same meaning as defined above, and L stands for a halogen atom or a substituted sulfonic acid ester group.

The above-mentioned reaction (a) is alkylation using an alkylating agent (III) in the presence of a base.

The alkylation is conducted, employing approximately 1 to 3 moles each of the base and the alkylating agent relative to one mole of the compound (II), usually in an organic solvent such as amides (e.g. dimethylformamide or dimethylacetamide), sulfoxides (e.g. dimethylsulfoxide), nitriles (e.g. acetonitrile), ketones (e.g. acetone or ethyl methyl ketone) and ethers (e.g. tetrahydrofuran or dioxane).

Examples of the base include butyl lithium, sodium hydride, potassium t-butoxide, potassium carbonate and sodium carbonate.

As the alkylating agent (III), use is made of, for example, substituted halides (e.g. chloride, bromide and iodide) and substituted sulfonic acid esters (e.g. p-toluenesulfonic acid ester, benzenesulfonic acid ester and methanesulfonic acid ester).

While the reaction conditions vary with the combination of the base and the alkylating agent then employed, it is preferable to conduct the reaction usually at temperatures ranging from −78° C. to 100° C. for about 1 to about 50 hours.

Reaction (b)

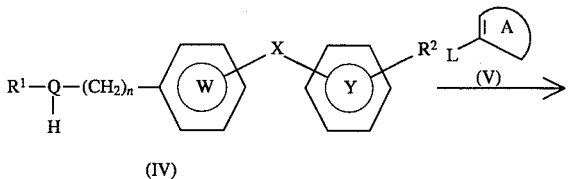

(IV)

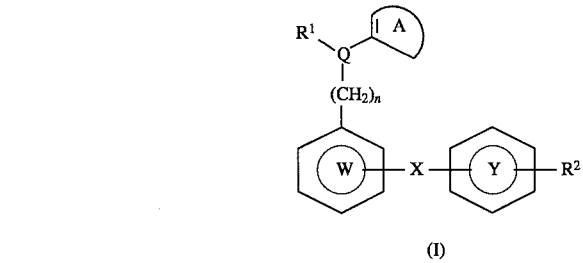

(I)

[wherein A, $R^1$, $R^2$, L, Q, w, x, Y and n are of the same meaning as defined above].

The above-mentioned reaction (b) is arylation by allowing an arylating agent (V) to act on the compound (IV) in the presence of a base.

The arylation is conducted, employing 1 to 3 moles each of the base and the arylating agent (V) relative to 1 mole of the compound (IV), usually in an organic solvent such as amides (e.g. dimethylformamide or dimethylacetamide), sulfoxides (e.g. dimethylsulfoxide), nitriles (e.g. acetonitrile), ketones (e.g. acetone or ethyl methyl ketone) and ethers (e.g. tetrahydrofuran or dioxane).

Examples of the base include butyl lithium, sodium hydride, potassium t-butoxide, potassium carbonate and sodium carbonate.

As the arylating agent (V), use is made of, for example, substituted halogenides such as chloride, bromide and iodide, and substituted sulfonic acid esters such as p-toluenesulfonic acid ester, benzenesulfonic acid ester and methanesulfonic acid ester.

While the reaction conditions vary with the combination of the base and the arylating agent then employed, it is preferable to conduct the reaction usually at temperatures ranging from about −78° C. to about 100° C. for about 1 to about 50 hours.

Reaction (c)

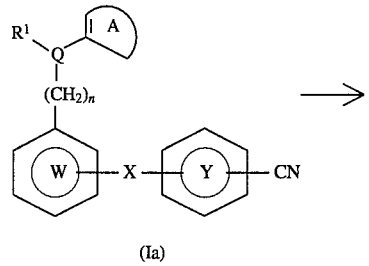

(Ia)

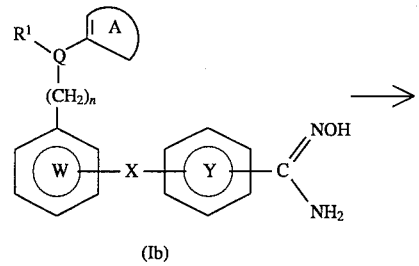

(Ib)

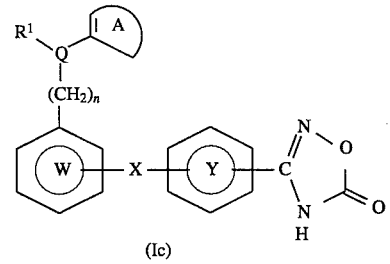

(Ic)

[wherein A, $R^1$, W, Y, Z and n are of the same meaning as defined above].

The above-mentioned reaction (c) is to obtain the oxadiazole compound (Ic) by converting the cyano compound (Ia) into the amidoxime (Ib) followed by the ring formation.

The reaction for obtaining the compound (Ib) is conducted by using approximately 2 to 10 moles of hydroxylamine relative to 1 mole of the compound (Ia) in a conventional organic solvent.

Examples of the solvent include amides (e.g. dimethylformamide and dimethylacetamide), sulfoxides (e.g. dimethylsulfoxide), alcohols (e.g. methanol and ethanol), ethers (e.g. dioxane and tetrahydrofuran) and halogenated hydrocarbons (e.g. methylene chloride and chloroform).

When an inorganic acid salt (e.g. hydroxylamine hydrochloride or hydroxylamine sulfate) or an organic acid salt (e.g. hydroxylamine oxalate) is employed as hydroxylamine source, the reaction is conducted in the presence of a suitable base (e.g. potassium carbonate, sodium carbonate, sodium hydroxide, triethylamine, sodium methoxide, sodium ethoxide and sodium hydride) of about equimolar amount. While the reaction conditions vary with the reagent or solvent then employed, the reaction is preferably conducted at about 50° C. to about 100° C. for about 2 to about 24 hours, after the hydroxylamine hydrochloride is treated with sodium methoxide or triethylamine in dimethyl sulfoxide.

The thus-obtained amidoxime (Ib) is allowed to react with chloroformate (e.g. methyl ester and ethyl ester) in a conventional organic solvent (e.g. chloroform, methylene chloride, dioxane, tetrahydrofuran, acetonitrile and pyridine) in the presence of a base (e.g. triethylamine, pyridine, potassium carbonate and sodium carbonate) to give an o-acyl compound.

Preferably, the reaction is usually conducted by using 2 to 5 moles of ethyl chloroformate relative to one mole of the amidoxime (Ib) in the presence of about 2 to about 5 moles of triethylamine in tetrahydrofuran at temperatures ranging from 0° C. to room temperatures for about 1 to about 5 hours.

By heating thus-obtained o-acyl amidoxime in a conventional organic solvent, the cyclized compound (Ic) is easily obtained.

Examples of the solvent include aromatic hydrocarbons (e.g. benzene, toluene and xylene), ethers (e.g. dioxane and tetrahydrofuran) and halogenated hydrocarbons (e.g. dichloroethane and chloroform). Preferable reaction conditions comprise heating o-acyl amidoxime compound for about 1 to about 3 hours under reflux in xylene.

Reaction (d)

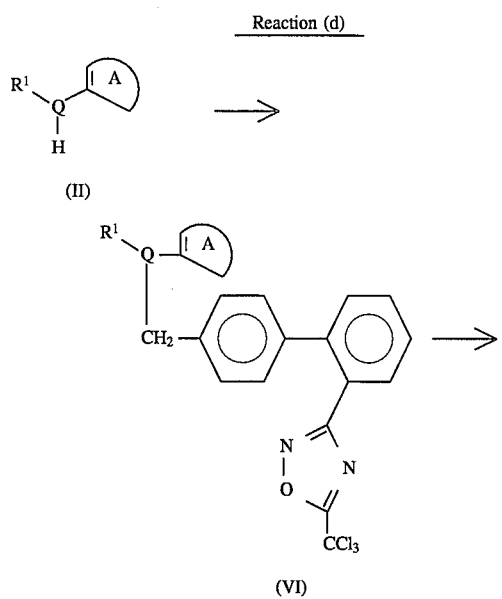

-continued
Reaction (d)

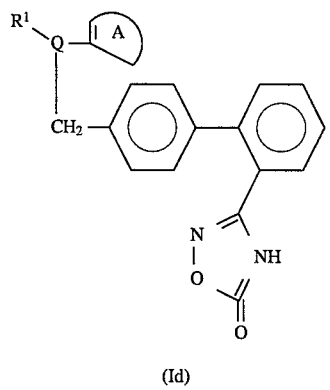

[wherein A, $R^1$ and Q are of the same meaning as defined above].

The above-mentioned reaction (d) is to obtain the oxadiazolone (Id) by hydrolyzing the compound (VI) produced by alkylation of the compound (II) with the alkylating agent (Xd) obtained in the reaction (k) described later.

Examples of the organic solvent include ethers (e.g. dioxane and tetrahydrofuran) and alcohols (e.g. methanol and ethanol).

As the alkali, mention is made of sodium hydroxide, potassium hydroxide and lithium hydroxide.

Preferably, the compound (VI) is reacted at 0° C. to room temperatures for about 0.5 to about 2 hours with about 2 to about 10 moles of a 0.5 to 1N aqueous solution of sodium hydroxide.

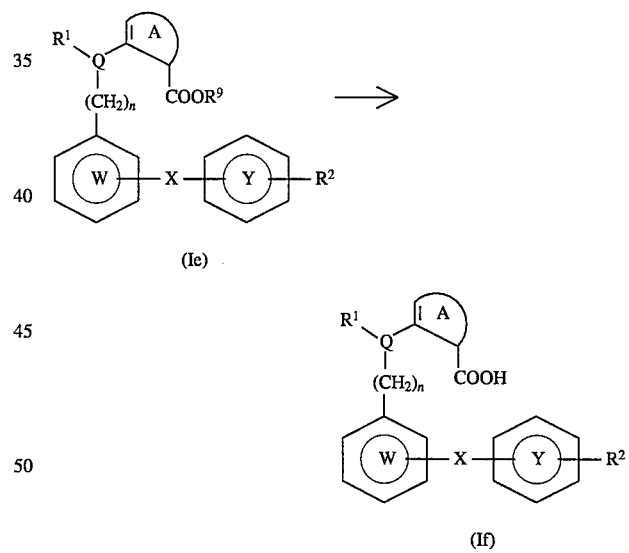

[wherein $R^1$, $R^2$, $R^9$, Q, w, X, Y and n are of the same meaning as defined above].

The above-mentioned reaction (e) is to obtain carboxylic acid (If) by alkali hydrolysis of the ester compound (Ie).

This reaction is conducted by using alkali in an amount of about 1 to about 3 moles relative to one mole of the compound (Ie) usually in a solvent such as aqueous alcohols (e.g. methanol, ethanol and methyl cellosolve).

Examples of the alkali include lithium hydroxide, sodium hydroxide and potassium hydroxide.

The reaction is conducted at room temperature to about 100° C. for about 1 to about 10 hours, preferably at about the boiling point of the solvent for about 3 to about 5 hours.

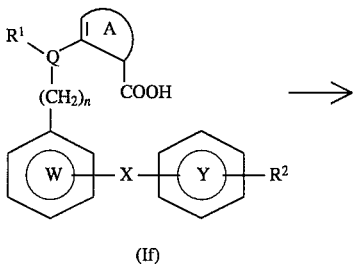

(If)

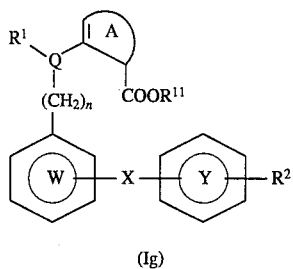

(Ig)

[wherein A, $R^1$, $R^2$, Q, w, X, Y and n are of the same meaning as defined above, and $R^{11}$ stands for optionally substituted alkyl group shown by the afore-mentioned $R^{10}$].

The above reaction (f) is alkylation by an alkylating agent in the presence of a base.

The alkylation is conducted by using 1 to 3 moles of the base and about 1 to about 3 moles of the alkylating agent relative to 1 mole of the compound (If) usually in a solvent such as dimethylformamide, dimethylacetamide, dimethyl sulfoxide, acetonitrile, acetone and ethyl methyl ketone.

Examples of the base include sodium hydroxide, potassium t-butoxide, potassium carbonate and sodium carbonate.

Examples of the alkylating agent include substituted halides (e.g. chloride, bromide and iodide) and substituted sulfonic acid esters (e.g. p-toluenesulfonic acid ester).

While the reaction conditions vary with combination of the base and the alkylating agent then employed, it is preferable to conduct the reaction at 0° C. to room temperatures for about 1 to about 10 hours.

And, when chloride or bromide is employed as the alkylating agent, it is preferable to add potassium iodide or sodium iodide to the reaction system to accelerate the reaction.

Reaction (g)

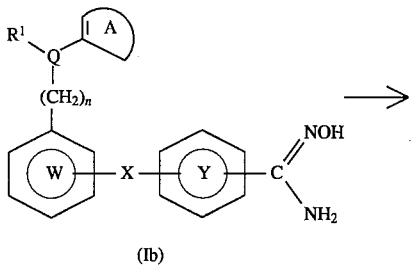

(Ib)

-continued
Reaction (g)

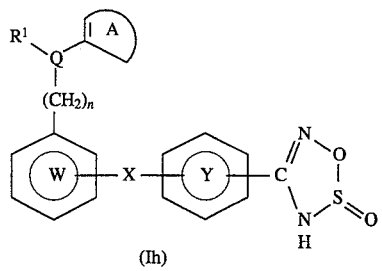

(Ih)

[wherein A, $R^1$, Q, w, X, Y and n are of the same the meaning as defined above]

The above-mentioned reaction (g) is to obtain oxathiadiazole (Ih) by cyclization of the amidoxime compound (Ib) obtained by the reaction (c).

The compound (Ih) is obtained by allowing the amidoxime (Ib) to react with thionyl chloride in a conventional organic solvent (e.g. dichloromethane, chloroform, dioxane and tetrahydrofuran) in the presence of a base (e.g. pyridine and triethylamine).

It is preferable to conduct the reaction, adding about 2 to about 10 moles of thionyl chloride to the reaction system, under cooling at 0° C. to −30° C., in the presence of about 1 to about 3 moles of pyridine relative to one mole of the amidoxime compound (Ib), using dichloromethane as the solvent, for about 0.5 to about 1 hour.

Reaction (h)

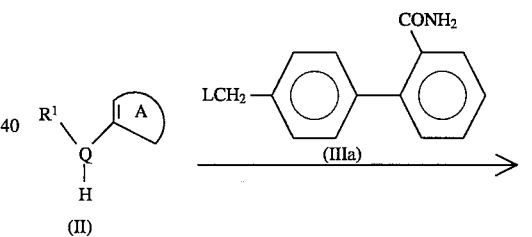

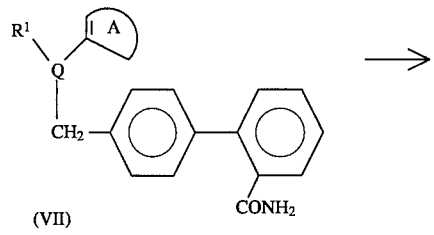

(VII)

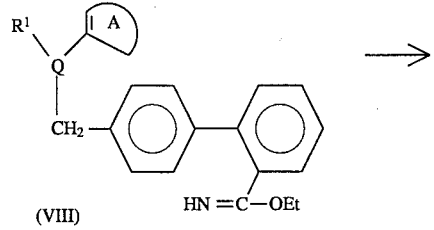

(VIII)

Reaction (h) -continued

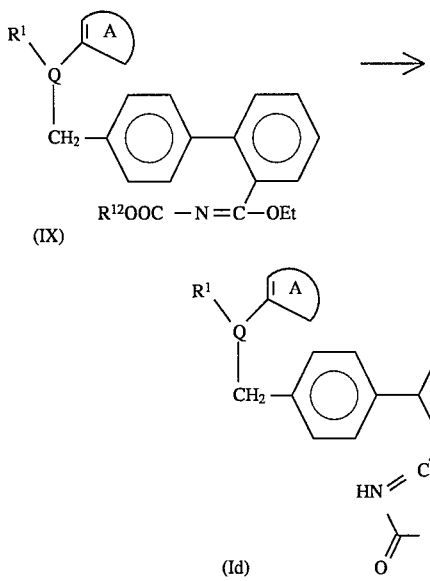

[wherein A, R¹, L and Q are of the same meaning as defined above, and $R^{12}$ stands for a lower ($C_{1-8}$) alkyl group]. In the above-mentioned reaction scheme (h), the compound (VII) is alkylated with the alkylating agent (IIIa) obtained in the reaction (1) to be illustrated later is allowed to react with about 1 to about 2 times as much moles of triethyl oxonium tetrafluoroborate in halogenated hydrocarbon (e.g. methylene chloride and chloroform) for about 0.5 to about 2 hours at temperatures ranging from 0° C. to room temperature to give the imidate (VIII) in a good yield.

Subsequently, the imidate (VIII) is allowed to react with about 1 to about 2 times as much moles of chloroformate (e.g. chloromethyl formate and chloroethyl formate) in a conventional organic solvent (e.g. benzene, toluene, methylene chloride, chloroform, dioxane and pyridine) in the presence of about 1 to about 2 times as much moles of a base (e.g. 2,4,6-trimethylpyridine, triethylamine, dimethylpyridine, methylpyridine and diethylaniline). The N-alkoxycarbonyl compound (IX) is obtained in a good yield by conducting the reaction in toluene at about 80 to about 100° C. for about 1 to about 3 hours. The N-alkoxycarbonyl compound (IX) thus obtained is cyclized by the reaction of about 2 times as much moles of hydroxylamine hydrochloride with a base (e.g. sodium methoxide, sodium ethoxide and potassium carbonate) in alcohol (e.g. methanol and ethanol). The reaction is preferably conducted at temperatures ranging from 50° C. to about the boiling point of the solvent then employed for about 3 to about 10 hours.

Reaction (i)

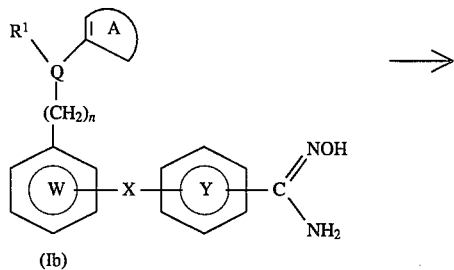

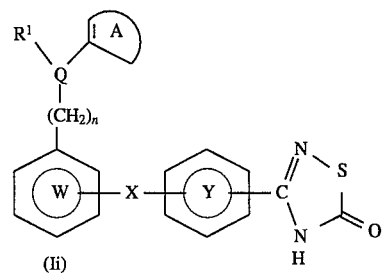

[wherein A, R¹, Q, W, X, Y and n are of the same meaning as defined above].

The above-mentioned reaction (i) is to obtain the thiadiazole (Ii) by cyclization of the amidoxime (Ib) obtained by the afore-mentioned reaction (c).

The reaction to obtain the compound (Ii) is conducted, by using about 1 to about 2 moles of 1,1'-thiocarbonyldiimidazole, in a conventional organic solvent in the presence of 1 to 10 equivalents of a Lewis acid (boron trifluoride diethyl ether, stannous chloride, stannic chloride, zinc chloride, cuprous chloride and silica gel).

Examples of the solvent include ethers (e.g. dioxane and tetrahydrofuran) and halogenated hydrocarbons (e.g. methylene chloride and chloroform).

Alternatively, it is preferable that the compound (Ib) is dissolved in a mixture of methanol and chloroform, to which is added 1,1'-thiocarbonyldiimidazole whole stirring together with silica gel at temperatures ranging from 0° C. to room temperature, followed by allowing the reaction to proceed for about 0.5 to about 2 hours at about room temperatures.

Reaction (j)

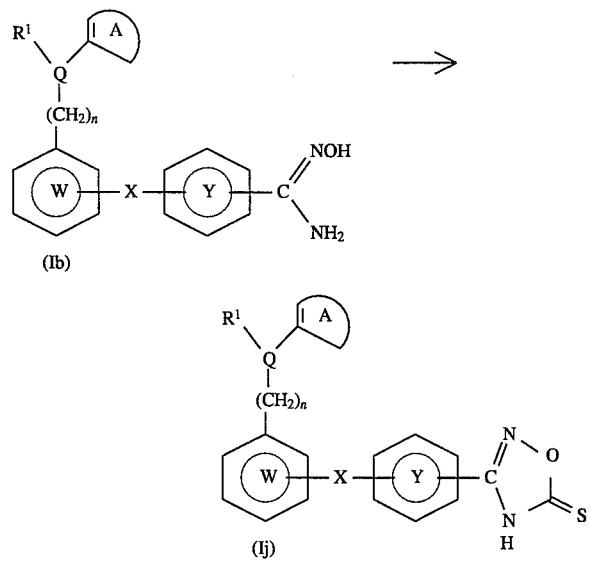

[wherein A, R¹, Q, W, X, Y and n are of the same meaning as defined above].

The above-mentioned reaction (j) is to obtain the thioketone derivative (Ij) by subjecting the amidoxime (Ib) obtained in the afore-mentioned reaction (c) to cyclization.

The reaction to obtain the compound (Ij) is conducted, using about 1 to about 10 moles of 1,1'-thiocarbonyl diimidazole, in a conventional solvent in the presence of a base.

As the solvent, use is made of, for example, ethers (e.g. dioxane and tetrahydrofuran), halogenated hydrocarbons (e.g. methylene chloride and chloroform), acetonitrile and acetone.

As the base, mention is made of, for example, amines (e.g. triethylamine, pyridine, 2,6-dimethylpyridine, 1,5-diazabicyclo[4.3.0] non-5-ene, 1,8-diazabicyclo[5.4.0]-7-undecene).

The reaction is preferably conducted by dissolving the compound (Ib) in acetonitrile and allowing the reaction to proceed at 0° C. to about room temperatures for about 10 minutes to about 24 hours.

The reaction (j) can be conducted also under such reaction conditions as the following.

The reaction is conducted, using about 1 to about 10 moles of acetic anhydride relative to 1 mole of the compound (Ib), in a conventional solvent in the presence of a base.

As the solvent, use is made of, for example, halogenated hydrocarbons (e.g. methylene chloride and chloroform) and ethers (e.g. dioxane and tetrahydrofuran).

As the base, mention is made of amines (e.g. triethylamine and pyridine). The reaction is preferably conducted, dissolving the compound (Ib) in methylene chloride, at temperatures ranging from 0° C. to room temperature for about 1 to about 5 hours.

By allowing 1 mole of O-acetylamidoxime thus obtained to react with about 3 to about 10 moles of carbon disulfide in an organic solvent in the presence of a base, thioketone (Ij) is obtained.

As the solvent, use is made of amides (e.g. N,N-dimethylformamide and dimethylacetamide) or dimethyl sulfoxide.

As the base, mention is made of sodium hydride or potassium t-butoxide. The reaction of O-acetylamidoxime with carbon disulfide is preferably conducted in dimethylformamide for about 1 to about 3 hours, adding sodium hydride portionwise to the reaction system while stirring at room temperatures.

The reaction products obtained as above by the reactions (a) to (j) can easily be isolated by conventional isolation and purification process, for example, column chromatography and recrystallization.

Incidentally, these compounds (I) can be converted, by conventional methods, to salts with physiologically acceptable acids or bases. These salts include, for example, salts with an inorganic acid such as hydrochloric acid, sulfuric acid and nitric acid and, depending on the compounds, salts with an organic acid such as acetic acid, oxalic acid, succinic acid and maleic acid, salts with an alkali metal such as sodium and potassium, and salts with an alkaline earth metal such as calcium.

The starting compounds can be synthesized by the methods described as follows.

Reaction (k)

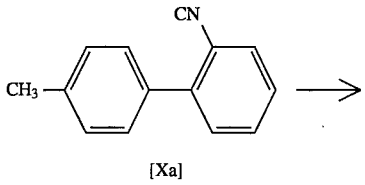

[Xa]

-continued
Reaction (k)

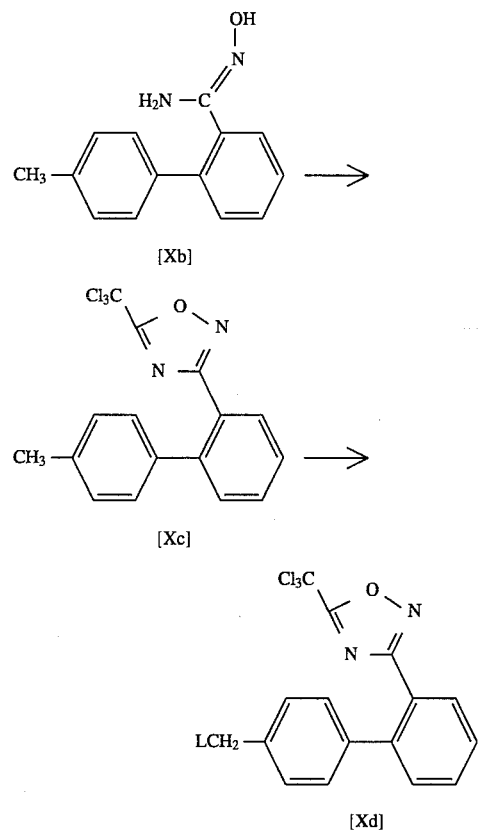

[wherein L is of the same meaning as defined above].

The above reaction (k) is to obtain the compound (Xd), by converting the cyano compound (Xa) to the amidoxime compound (Xb) under substantially the same reaction conditions as in the reaction (c), then subjecting the amidoxime compound (Xb) to cyclization to give the oxadiazole compound (Xc), followed by subjecting the oxadiazole compound (Xc) to halogenation.

The amidoxime compound (Xb) obtained from the compound (Xa) by substantially the same procedure as in reaction (c) is allowed to react with about 1 to about 10 moles of trichloroacetic anhydride or hexachloroacetone relative to one mole of the amidoxime (Xb) in accordance with the method described in the literature reference [F. Eloy, et al., Helv. Chim. Acta, 49, 1430(1966)] to give the oxadiazole compound (Xc), then the compound (Xc) thus obtained is allowed to react with a halogenating agent (e.g. N-bromosuccinimide and N-bromoacetamide) (molar ratio= about 1:1 to 1:1.5) in halogenated hydrocarbon (e.g. carbon tetrachloride) at temperatures ranging from 50° C. to the boiling point of the solvent then employed for about 1 to about 3 hours, in the presence of a catalytic amount of an initiator (e.g. benzoyl peroxide and azobisisobutyronitrile). This reaction can also be carried out under irradiation of light.

Reaction (l)

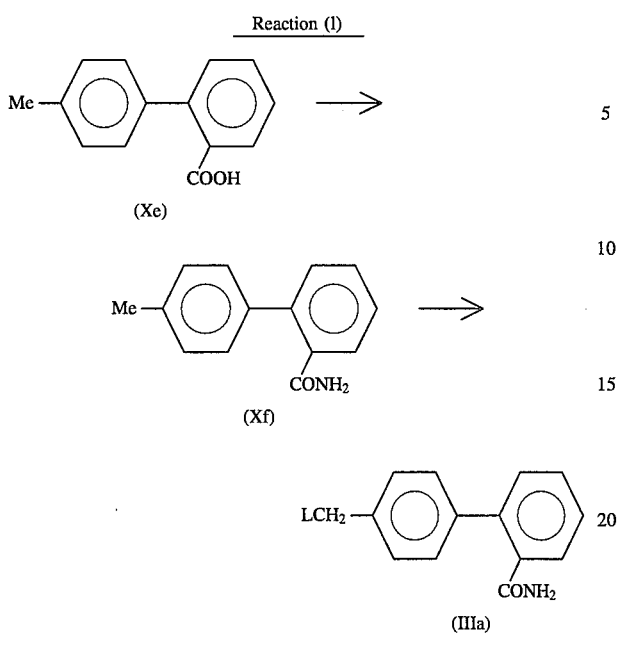

[wherein L is of the same meaning as defined above].

The reaction (l) comprises converting carboxylic acid (Xe) to amide (Xf) by a conventional manner, then leading (Xf) to the halogenide (IIIa).

The carboxylic acid (Xe) is allowed to react with about 2 to about 5 moles of a halogenating agent (e.g. oxalyl chloride or thionyl chloride) in an organic solvent (e.g. tetrahydrofuran, chloroform or methylene chloride) at temperatures ranging from room temperature to the boiling point of the solvent then used for about 1 to about 20 hours. It is preferable to accelerate this reaction by the addition of a catalytic amount of dimethylformamide. The acid halide thus obtained is preferably allowed to to react with an excess amount of aqueous ammonia in an organic solvent (e.g. tetrahydrofuran or dioxane) at temperatures ranging from 0° C. to room temperature for about 1 to about 10 hours, so that the amide derivative (Xf) can be obtained in a good yield.

The reaction to obtain the halide (IIIa) from the amide derivative (Xf) is conducted preferably in substantially the same manner as described in the reaction (k).

Reaction (m)

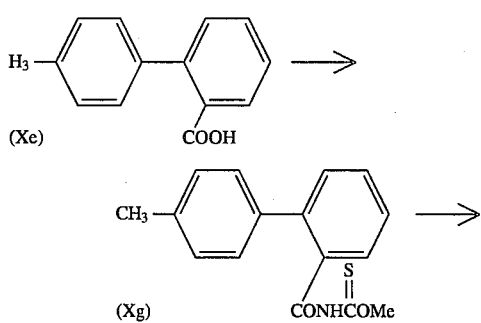

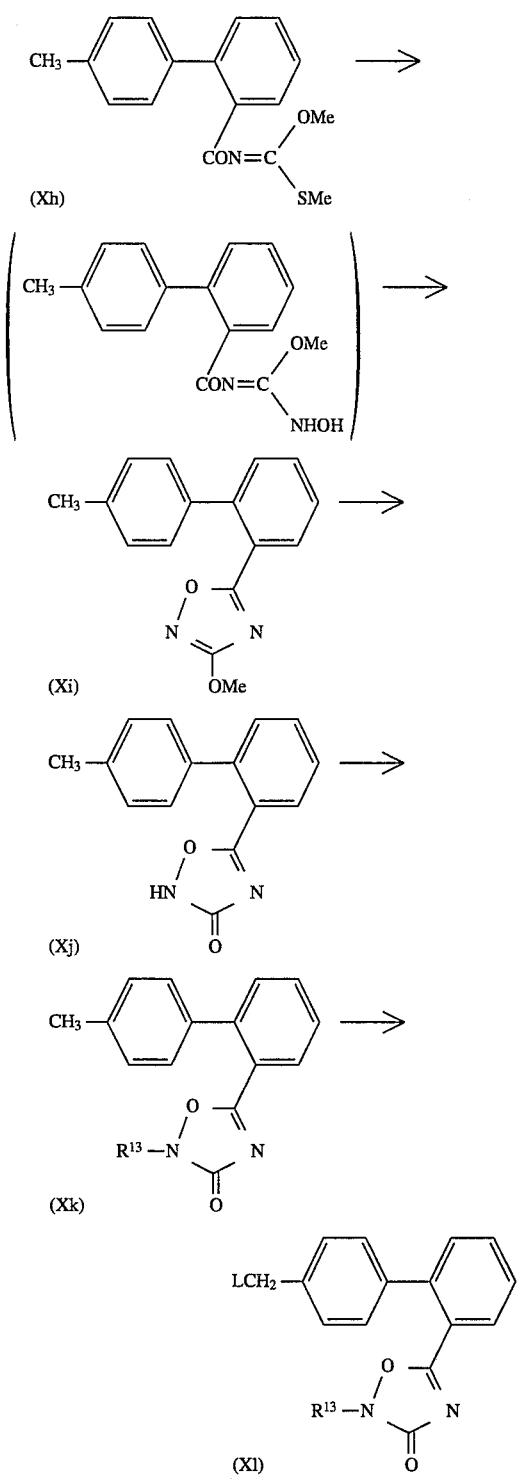

[wherein $R^{13}$ stands for an optionally substituted alkyl group shown by the above-mentioned $R^{10}$ (e.g. triphenyl methyl, methoxy methyl and cyanoethyl) or t-butyldimethyl silyl group; and L is of the same meaning as defined above].

The reaction (m) is to obtain the oxadiazole compound (Xi), which comprises leading carboxylic acid (Xe) to acyl isothiocyanate by a conventional method, allowing the latter to react with alcohol to give carbonyl thiocarbamate (Xg), subjecting the compound (Xg) to methylation to give carbonate (Xh), then allowing the compound (Xh) to react with hydroxylamine, followed by cyclization under heating.

In the reaction for obtaining carbonyl thiocarbamate (Xg), the compound (Xe) is allowed to react with about 2 to about 5 moles of a halogenating agent (e.g. thionyl chloride) relative to 1 mole of (Xe) in halogenated hydrocarbon (e.g. chloroform and methylene chloride) for about 1 to about 5 hours at temperatures ranging from 50° C. to the boiling point of the solvent then employed to give acid chloride. The acid chloride thus obtained is allowed to react with about 2 to about 5 moles of thiocyanate (e.g. sodium salt and potassium salt) in ether (e.g. dioxane and tetrahydrofuran) at temperatures ranging from 50° C. to the boiling point of the solvent then employed for about 1 to about 3 hours to give isothiocyanate. It is preferable to subject the isothiocyanate thus obtained to heating together with about 2 to about 10 moles of alcohol (e.g. methanol and ethanol) at temperatures ranging from about 50° C. to the boiling point of the solvent then employed for about 15 minutes to one hour.

In the reaction for obtaining iminomonothiocarbonate (Xh) from the compound (Xg), it is preferable to allow the compound (Xg) to react with methyl iodide (molar ratio=1:1 to 1:2) in an organic solvent (e.g. methanol, ethanol, dimethylformamide (DMF) and acetonitrile), in the presence of about 1 to about 2 moles, relative to one mole of (Xg), of a base (e.g. NaOMe, Na$_2$CO$_3$ and K$_2$CO$_3$) at temperatures ranging from room temperature to about 50° C. for about 10 to about 24 hours.

In the reaction for obtaining oxadiazole compound (Xi) from the compound (Xh), it is preferable to allow (Xh) to react with hydroxylamine (molar ratio=about 1:1 to 1:2) in alcohol (e.g. methanol and ethanol) at temperatures ranging from room temperature to about 50° C. for about 10 to about 20 hours, followed by subjecting the reaction mixture to heating in an organic solvent (e.g. toluene and benzene) in the presence of about a catalytic amount of an acid (e.g. p-toluenesulfonic acid) at temperatures ranging from about 50° C. to the boiling point of the solvent then employed for about 1 to about 3 hours.

In the reaction for obtaining the demethylated compound (Xj) from the compound (Xi), it is preferable to subject an excess amount of pyridine hydrochloride and (Xi) to fusing reaction under nitrogen atmosphere at temperatures ranging from about 150 to about 160° C. for about 0.5 to about 1 hour.

In the reaction for obtaining the compound (Xk) from the compound (Xj), it is preferable to allow the compound (Xj) to react with an alkylating agent (e.g. triphenylmethyl chloride, methoxymethyl chloride and cyanoethyl chloride) (molar ratio=about 1:1 to 1: about 2) in an organic solvent (e.g. chloroform, methylene chloride, dioxane, tetrahydrofuran and pyridine) in the presence of about 1 to about 2 moles of a base (e.g. potassium carbonate, sodium carbonate, triethylamine and pyridine) at temperatures ranging from 0° C. to about room temperature for about 1 to about 3 hours.

The reaction for obtaining the compound (Xl) by halogenating the compound (Xk) can be conducted in substantially the same manner as in the reaction for obtaining the compound (Xd) from the compound (Xc) in the above reaction (k).

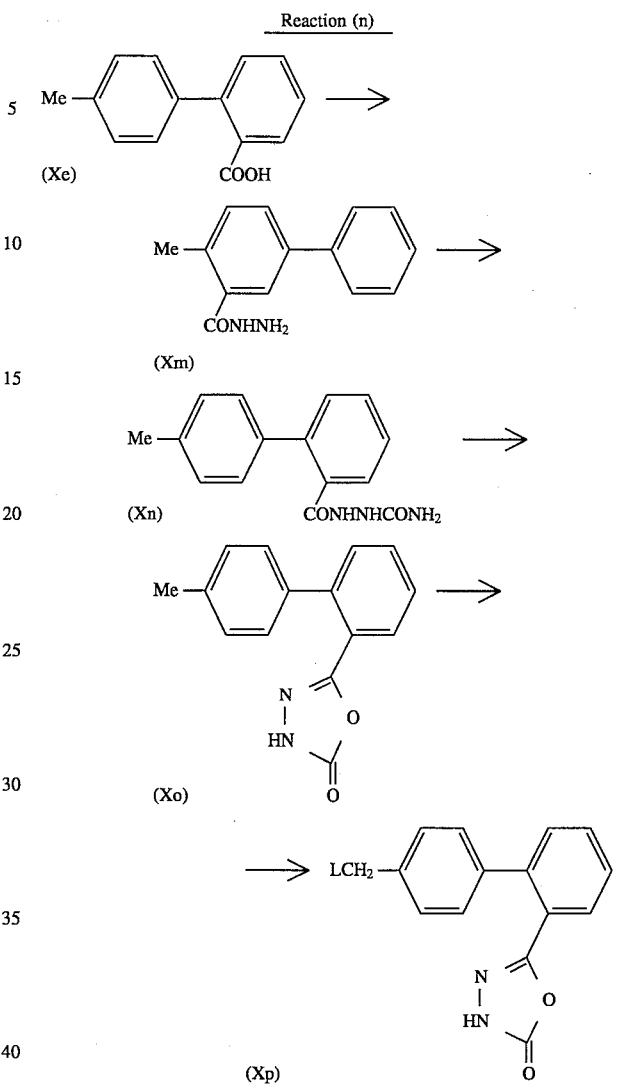

[wherein L is of the same meaning as defined above].

The reaction (n) comprises converting carboxylic acid (Xe) to semicarbazide (Xn) via hydrazide (Xm) by a conventional manner, then subjecting (Xn) to dehydrocyclization to give oxadiazolone (Xo), followed by leading (Xo) to the halogenated compound (Xp).

In the reaction for obtaining hydrazide (Xm) from carboxylic acid (Xe), (Xe) is allowed to react with about 2 to about 5 moles of a halogenating agent (e.g. oxalyl chloride and thionyl chloride) in an organic solvent (e.g. tetrahydrofuran, chloroform and methylene chloride) at temperatures ranging from room temperature to the boiling point of the solvent then employed for about 1 to about 20 hours. In this case, it is preferable to add a catalytic amount of dimethylformamide to accelerate the reaction. The acid chloride thus obtained is allowed to react with about 2 to about 5 moles of hydrazine hydrate in an organic solvent (e.g. tetrahydrofuran and dioxane) at temperatures ranging from room temperature to about 50° C. for about 1 to about 10 hours to obtain (Xm).

In the reaction for producing semicarbazide (Xn) from the hydrazide (Xm) thus obtained, it is preferable to allow (Xm) to react with about 2 to 5 moles of isocyanate (e.g. sodium or potassium salt) in an aqueous solution in the presence of an acid (e.g. hydrochloric acid or sulfuric acid) in an amount equal to that of the isocyanate then employed at temperatures ranging from 0° C. to room temperature for about 1 to about 5 hours.

In the reaction for producing oxadiazolone (Xo) from the semicarbazide (Xn) thus obtained, it is preferable to heat (Xn) in an organic solvent (e.g. benzene and xylene) at about the boiling point of the solvent then employed for about 5 to about 20 hours.

The reaction for producing the halogenated compound (Xp) from the oxadiazolone (Xc) thus obtained is preferably conducted in a manner similar to that described in the reaction (k) mentioned above.

The compounds (I) and their salts are relatively less toxic, strongly inhibit the vasoconstrictive and pressor response induced by angiotensin II, exert a hypotensive effect in animals, especially mammals (e.g. human being, dog, rabbit and rat), and therefore the angiotensin II antagonistic agent of this invention containing the compound (I) or a salt thereof is useful as a therapeutic agent for not only hypertension but also circulatory diseases such as cardiac diseases (hypertrophy of the heart, cardiac insufficiency, cardiac infarction or the like), cerebral apoplexy, nephropathy and arteriosclerosis. And, the compound (I) is useful also as an agent of improving cerebral functions observed in Alzheimer's disease or senile dementia, through its action on central nervous system, and further has an action of antianxiety and antideprementia.

For such therapeutic use as above, the compound (I) or a salt thereof can be safely administered orally, parenterally by inhalation, rectally or topically as pharmaceutical compositions or formulations (e.g. powders, granules, tablets, pills, capsules, injections, suppositories, syrups, emulsions, elixir, suspensions and solutions), comprising at least one species of the compounds of the present invention alone or in admixture with pharmaceutically acceptable carriers, adjuvants, excipients, vehicles and/or diluents.

Pharmaceutical compositions can be formulated in accordance with conventional procedures. In the present specification, "parenterally" includes subcutaneous injection, intravenous injections, intramuscular injection, intraperitoneal injection or instillation. Injectable preparations, for example, sterile injectable aqueous suspensions or oil suspensions can be prepared by known procedure in the fields concerned, using a suitable dispersant or wetting agent and suspending agent. The sterile injections may be in the state of, for example, a solution or a suspension, which is prepared with a non-toxic diluent administrable parenterally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. Any nonvolatile oil and a fatty acid can be used for this purpose, which includes natural, synthetic or semi-synthetic fatty acid oil or fatty acid and natural or synthetic or semi-synthetic mono- or di- or tri-glycerides.

Rectal suppositories can be prepared by mixing the drug with a suitable non-irritable vehicle, for example, cocoa butter and polyethylene glycol, which is in the solid state at room temperatures, in the liquid state at temperatures in intestinal tubes and melts in rectum to release the drug.

As a solid formulation for oral administration, mention is made of powders, granules, tablets, pills and capsules as referred to above. In such formulations as exemplified above, the active component can be mixed with at least one additive, for example, sucrose, lactose, cellulose, sugar, mannitol, maltitol, dextrin, starch, agar, alginate, chitin, chitosan, pectin, tragacanth, gum arabic, gelatin, collagen, casein, albumin, synthetic or semi-synthetic polymer or glyceride. Conventionally, these formulations can contain further additives, for example, an inactive diluent, a lubricant such as magnesium stearate, a preservative such as paraben or sorbic acid, an anti-oxidant such as ascorbic acid, α-tocopherol or cysteine, a disintegrator, a binder, a thickening agent, a buffer, a sweetener, a flavoring agent and a perfuming agent. Tablets and pills can further be prepared with enteric coating. Examples of liquid preparations for oral administration include pharmaceutically acceptable emulsions, syrups, elixirs, suspensions and solutions, which may contain an inactive diluent, for example, water, which is conventionally employed in the field concerned.

The dose of a specific patient is decided depending on the age, body weight, general health conditions, sex, diet, dose interval, administration routes, excretion rate, combinations of drugs and conditions of the diseases then treated, while taking them and any other necessary factors into consideration.

The dose varies with the diseases to be treated, conditions of such diseases, subject patients and administration routes, and it is preferable that a daily dose of about 1 to about 100 mg (preferably about 1 to about 50 mg) for oral administration or about 0.01 to about 50 mg (preferably about 0.3 to about 30 mg) for intravenous injection is given once or divided into two or three administrations when used as an agent for the therapy of essential hypertension of an adult human.

EXAMPLES

By the following reference examples, working examples, experimental examples and formulation examples, the present invention will be illustrated more concretely, and it is needless to say that they should not be construed as limiting the invention thereto.

Reference Example 1

4-Methylbiphenyl-2-carboxamido oxime

To a solution of hydroxylamine hydrochloride (17.9 g) in dimethyl sulfoxide (120 ml) was added a methanolic solution of sodium methoxide prepared from metallic sodium (5.92 g) and anhydrous methanol (50 ml). The mixture was stirred for 10 minutes at room temperature, to which was added 2'-cyano-4-methylbiphenyl (10 g). The reaction mixture was stirred for 5 hours at 100° C. The reaction mixture was partitioned between ethyl acetate and water, and the aqueous layer was extracted with ethyl acetate. The organic layers were combined, washed with water and dried, then the solvent was distilled under reduced pressure. The residue was purified by column chromatography on silica gel to afford the title compound as white amorphous product (11.2 g, 96%). $^{1}$H-NMR (200MHz, CDCl$_3$) δ: 2.39(3H,s), 4.42(2H,br s), 7.22(2H,d), 7.31–7.50(5H,m), 7.56–7.60(1H, m). IR(KBr) cm$^{-1}$: 3490, 3380, 1642, 1575, 1568.

Reference Example 2

5-Trichloromethyl-3-(4'-methylbiphenyl-2-yl)-1, 2,4-oxadiazole

To a benzene (100 ml) solution of the compound (10 g) obtained in Reference Example 1 in benzene (100 ml) was added dropwise trichloroacetic anhydride (16.4 g). The reaction mixture was then heated under reflux for two hours. The reaction mixture was cooled and concentrated to dryness. The residue was partitioned between ether and water. The aqueous layer was extracted with ether. The extract was combined with the organic layer, which was washed with water and dried, then the solvent was distilled under reduced pressure. The residue was purified by column chromatography on silica gel to afford the title compound as a pale yellow oil (12 g, 77%). $^1$H-NMR (200MHz,CDCl$_3$) δ: 2.38(3H,s), 7.16(4H,s), 7.44–7.64(3H,m), 7.88–7.93(1H,m). IR (neat) cm$^{-1}$: 3025, 1600, 1580, 1561, 1508.

Reference Example 3

5-Trichloromethyl-3-(4'-bromomethylbiphenyl-2-yl)-1,2,4-oxadiazole

To a solution of the compound (24.8 g) obtained in Reference Example 2 in carbon tetrachloride (300 ml) were added N-bromosuccinimide (12.5 g) and α, α'-azobisisobutyronitrile (1.15 g). The mixture was heated for two hours under reflux, which was then cooled. White insoluble material was filtered off, and the filtrate was diluted with dichloromethane. The organic layer was washed with water and dried, then the solvent was distilled under reduced pressure. The residue was recrystallized from ether-hexane to afford the the title compound as colorless crystals (23.0 g, 76%), m.p. 77°–79° C.

| Elemental Analysis for C$_{16}$H$_{10}$N$_2$OBrCl$_3$.0.5H$_2$O: | | | |
|---|---|---|---|
| | C (%) | H (%) | N (%) |
| Calcd.: | 43.52; | 2.51; | 6.34 |
| Found: | 43.76; | 2.33; | 6.31 |

$^1$H-NMR (200MHz,CDCl$_3$) δ: 4.52(2H,s), 7.23(2H,d), 7.38(2H,d), 7.44–7.65(3H,m), 7.91–7.95(1H,m). IR (KBr) cm$^{-1}$: 1600, 1560, 1475, 1428, 1332.

Reference Example 4

4'-Bromomethylbiphenyl-2-carboxamide

4'-Methylbiphenyl-2-carboxamide (2.1 g), N-bromosuccinic acid imide (2.5 g) and azobisisobutyronitrate (AIBN: 82 mg) were added benzene (20 ml), then the mixture was stirred for 20 hours at 60°–70° C. Resulting crystalline precipitate was collected by filtration and washed with isopropyl ether, which were suspended in water. The suspension was stirred for 30 minutes. Insoluble material was collected by filtration and dried. Crude crystals thus obtained were recrystallized from ethyl acetate-methanol to afford colorless needles (1.6 g, 55%), m.p. 220°–221° C. (d).

| Elemental Analysis for C$_{14}$H$_{12}$BrNO: | | | |
|---|---|---|---|
| | C (%) | H (%) | N (%) |
| Calcd.: | 57.95; | 4.17; | 4.83 |
| Found: | 57.85; | 4.16; | 4.77 |

$^1$H-NMR (200MHz, DMSO-d$_6$) δ: 4.75(2H,s), 7.31–7.69(10H,m). IR (KBr) cm$^{-1}$: 3150, 3000, 1570, 1540, 1520, 1500, 1300, 665.

Working Example 1

Ethyl 2-[N-propyl-N-[2'-(2,5-dihydro-5-oxo-1,2,4-oxadiazol-3-yl)biphenyl-4-yl]methyl]aminopyridine-3-carboxylate a) Ethyl 2-chloropyridine-3-carboxylate 2-Chloropyridine-3-carboxylic acid (7.9 g) and thionyl chloride (45 ml) were heated for 3 hours in benzene (65 ml) under reflux. The reaction mixture was concentrated to leave an oil, which was added dropwise to ethanol (40 ml). The mixture was heated for further one hour under reflux. The solvent was distilled, and the residue was dissolved in toluene. The solution was dried over anhydrous magnesium sulfate. The solvent was distilled to leave the title compound (8.4 g, 90%) as a pale yellow oil. $^1$H-NMR (200MHz, CDCl$_3$) δ: 1.42(3H,t), 4.44(2H,q), 7.34(1H,dd), 8.17(1H, dd), 8.52(1H,dd).

b) Ethyl 2-propylaminopyridine-3-carboxylate

The compound (4.6 g) obtained in Working Example 1 a) and propylamine (9 ml) were dissolved in ethanol. The solution was heated in a sealed tube for 6 hours at 100° C. The reaction mixture was concentrated and the residue was dissolved in ethyl acetate. The solution was washed with a sodium hydroxide solution and dried over anhydrous magnesium sulfate. The solvent was distilled to give an oil, which was purified by column chromatography on silica gel to afford the title compound (4.1 g, 79%) as a colorless oil. $^1$H-NMR (200MHz,CDCl$_3$) δ: 1.01(3H,t), 1.38(3H,t), 1.60–1.74(2H,m), 3.48(2H,dt), 4.32(2H,q), 6.50(1H,dd), 8.01(1H,br), 8.12(1H,dd), 8.28(1H,dd).

c) Ethyl 2-[N-[2'-(2,5-dihydro-5-oxo-1,2,4-oxadiazol-3-yl)biphenyl-4-yl]methyl-N-propyl]aminopyridine-3-carboxylate To a solution of the compound (0.62 g) obtained in Working Example 1 c) and 1,3-dimethyl-3,4,5,6-tetrahydro-2(1H)-pyrimidone (0.73 g) in tetrahydrofuran (2 ml) was added dropwise, under ice-cooling, lithium hexamethyl disilaxide prepared from hexamethyl disilazane (0.72 g) and a 1.6M butyryl lithium tetrahydrofuran solution (2.8 ml). The mixture was stirred for 10 minutes, to which was then added dropwise a solution of the compound (2.0 g) obtained in Reference Example 3 in tetrahydrofuran (6 ml). The reaction mixture was stirred for 3 days at room temperature and the resulting mixture was poured into 1N HCl (10 ml), followed by adjusting at pH 6–7 with 1N NaOH. The resulting solution was extracted with ethyl acetate, and the extract was washed with water and dried over anhydrous magnesium sulfate. The solvent was distilled, and the residue was purified by column chromatography on silica gel. A crude product thus obtained was recrystallized from ethyl acetate-hexane to afford the tile compound (0.20 g, 14%) as colorless needles, m.p.168°–169° C.

| Elemental Analysis for C$_{26}$H$_{26}$N$_4$O$_4$: | | | |
|---|---|---|---|
| | C (%) | H (%) | N (%) |
| Calcd.: | 68.11; | 5.72; | 12.22 |
| Found: | 67.85; | 5.72; | 12.37 |

$^1$H-NMR (200MHz,CDCl$_3$) δ: 0.72(3H,t), 1.29(3H,t), 1.42–1.61(2H,m), 3.17(2H,t), 4.25(2H,q), 4.64(2H,s), 6.61(1H,dd), 7.17(2H,d), 7.30(2H,d), 7.33–7.57(3H,m), 7.77–7.85(2H,m), 8.07(1H,dd). IR(KBr) cm$^{-1}$: 1770, 1725, 1585, 1565, 1495, 1480, 1460, 1440, 1280, 1250, 1225, 1120, 1090, 1060, 760.

Working Example 2

2-[N-[2'-(2,5-dihydro-5-oxo-1,2,4-oxadiazol-3-yl)biphenyl-4-yl]methyl]-N-propyl]aminopyridine-3-carboxylic acid The compound (0.15 g) obtained in Working Example 1 c), 1N NaOH (1.5 ml) and methanol (1 ml) were mixed, and the mixture was heated for 1.5 hour under reflux. The reaction mixture was diluted with water, which was adjusted at pH 3–4 with 1N HCl followed by extraction with chloroform. The extract solution was washed with water and dried over anhydrous magnesium sulfate. The solvent was distilled and the residue was purified by column chromatography on silica gel. Crude crystals thus obtained were recrystallized from ethyl acetate-methanol to afford the title compound (0.11 g, 79%) as colorless prisms, m.p.203°–204° C.

| Elemental Analysis for $C_{24}H_{22}N_4O_4$: | | | |
|---|---|---|---|
| | C (%) | H (%) | N (%) |
| Calcd.: | 66.97; | 5.15; | 13.02 |
| Found: | 66.96; | 5.17; | 13.18 |

$^1$H-NMR (200MHz,DMSO-d$_6$) δ: 0.74(3H,t), 1.43–1.61(2H,m), 3.26(2H,t), 4.74(2H,s), 6.80(1H,dd), 7.25(2H,d), 7.35(2H,d), 7.51–7.70(4H,m), 7.86–7.91(1H,m), 8.23–8.26(1H,m). IR (KBr) cm$^{-1}$: 1780, 1590, 1495, 1470, 1455, 1430, 1380, 1220, 1200, 930, 850, 840, 790, 760, 755, 740.

Working Example 3

Ethyl 2-[N-[2'-(2,5-dihydro-5-oxo-1,2,4-thiadiazol-3-yl)biphenyl-4-yl]methyl-N-propyl]aminopyridine-3-carboxylate a) Ethyl 2-[N-(2'-cyanobiphenyl-4-yl)methyl-N-propyl]pyridine-3-carboxylate To a solution of the compound (2.0 g) obtained in Working Example 1 b) in N,N-dimethylformamide (10 ml) was added 60% sodium hydride in oil (0.42 g). The mixture was stirred for 3 hours at room temperature, to which was added 4'-bromomethyl-2-cyanobiphenyl (3.1 g), followed by stirring for further 19 hours at room temperature. The reaction mixture was diluted with ethyl acetate and dried over anhydrous magnesium sulfate. The solvent was distilled, and the residue was purified by column chromatography on silica gel to afford the title compound (1.3 g, 34%) as a colorless oil. $^1$H-NMR (200MHz,CDCl$_3$) δ: 0.81(3H,t), 1.37(3H,t), 1.59(2H,m), 3.29(2H,t), 4.33(2H,q), 4.79(2H,s), 6.70(1H,dd), 7.38–7.67(7H,m), 7.75(1H,dd), 7.91(1H,dd), 8.26(1H,dd). IR (neat) cm$^{-1}$: 2225, 1715, 1585, 1560, 1480, 1470, 1445, 1410, 1365, 1280, 1225, 1125, 1085, 765.

b) Ethyl 2-[N-[2'-(hydroxycarbamimidoyl)biphenyl-4-yl]methyl-N-propyl]pyridine-3-carboxylate To a solution of hydroxylamine hydrochloride (2.6 g) in dimethyl sulfoxide (DMSO) (25 ml) was added triethylamine (3.8 g), and the mixture was stirred for 30 minutes at room temperature. To the reaction mixture was added tetrahydrofuran (50 ml) and resulting precipitate was filtered off. From the filtrate was distilled off tetrahydrofuran. To a solution of hydroxylamine in DMSO was added the compound (1.5 g) obtained in Working Example 3 a), and the mixture was stirred for two days at 60°–65° C. To the reaction mixture was added water, which was extracted with ethyl acetate. The ethyl acetate solution was extracted with dilute hydrochloric acid. The aqueous layer was adjusted to pH 9–10, which was extracted with ethyl acetate. The extract was washed with water and dried over anhydrous magnesium sulfate. The solvent was distilled, and the residue was purified by column chromatography on silica gel to afford the title compound (1.2 g, 75%) as a colorless oil. $^1$H-NMR (200MHz,CDCl$_3$) δ: 0.81(3H,t), 1.36(3H,t), 1.59(2H,m), 3.30(2H,t), 4.32(2H,q), 4.38(2H,s), 4.74(2H,s), 6.68(1H,dd), 7.30–7.60(8H,m), 7.89(1H,dd), 8.25(1H,dd). IR (neat) cm$^{-1}$: 1710, 1650, 1580, 1555, 1480, 1440, 1360, 1280, 1220, 1120, 1080, 760.

c) Ethyl 2-[N-[2'-(2,5-dihydro-5-oxo-1,2,4-thiadiazol-3-yl)biphenyl-4-yl]methyl-N-propyl]aminopyridine-3-carboxylate The compound (1.2 g) obtained in Working Example 3 b) and 1,1'-thiocarbonyldiimidazole (0.55 g) were added tetrahydrofuran (6 ml). The mixture was stirred for 20 minutes at room temperature and the solvent was distilled off. The residue was dissolved in ethyl acetate. The solution was washed with water and dried over anhydrous magnesium sulfate. The solvent was distilled, and the residue was dissolved in tetrahydrofuran (6 ml). To the solution was added boron trifluoride diethyl etherate (0.64 g), and the mixture was stirred for 30 minutes at room temperature. The reaction mixture was diluted with water, which was extracted with ethyl acetate. The extract was washed with water, dried over anhydrous magnesium sulfate and, then the solvent was distilled off. The residue was purified by column chromatography on silica gel. Crude crystals thus obtained were recrystallized from ethyl acetate-hexane to afford the title compound (0.34 g, 26%) as colorless needles, m.p.134°–135° C.

| Elemental Analysis for $C_{26}H_{26}N_4O_3S$: | | | |
|---|---|---|---|
| | C (%) | H (%) | N (%) |
| Calcd.: | 65.80; | 5.52; | 11.81 |
| Found: | 66.00; | 5.46; | 11.87 |

$^1$H-NMR (200MHz,CDCl$_3$) δ: 0.80(3H,t), 1.37(3H,t), 1.53–1.64(2H,m), 3.25(2H,t), 4.34(2H,q), 4.75(2H,s), 6.70(1H,dd), 7.25(2H,d), 7.38–7.60(5H,m), 7.86–7.94(2H,m), 8.21(1H,dd), 8.43(1H,br s).

Working Example 4

2-[N-2'-(2,5-dihydro-5-oxo-1,2,4-thiadiazol-3-yl)biphenyl-4-yl]methyl-N-propylamino]pyridine-3-carboxylic acid Starting from the compound (0.24 g) obtained in Working Example 3 c), substantially the same procedure as in Working Example 2 was followed to afford the title compound as a colorless powder (0.18 g, 78%), m.p.91°–93° C.

| Elemental Analysis for $C_{24}H_{22}N_4O_3S \cdot 0.4H_2O$: | | | |
|---|---|---|---|
| | C (%) | H (%) | N (%) |
| Calcd.: | 63.53; | 5.06; | 12.35 |
| Found: | 63.66; | 4.95; | 12.07 |

$^1$H-NMR(200MHz,CDCl$_3$) δ: 0.86(3H,t), 1.43(2H,m), 3.21(2H,t), 4.29(2H,s), 7.18–7.59(8H,m), 7.74(1H,dd), 8.46(1H,dd), 8.66(1H,dd), 9.65(1H,br). IR(KBr)cm$^{-1}$: 1695, 1580, 1460, 1430, 765.

Working Example 5

Ethyl 2-[N-butyl-N-[2'-(2,5-dihydro-5-oxo-1,2,4-oxadiazol-3-yl)biphenyl-4-yl]methylamino]pyridine-3-carboxylate a) Ethyl 2-butylaminopyridine-3-carboxylate Starting from the compound (2.3 g) obtained in Working Example 1 a), substantially the same procedure as in Working Example 1 b) was followed to afford the title compound as a colorless oil (2.5 g, 93%). $^1$H-NMR(200MHz,CDCl$_3$) δ: 0.96(3H,t), 1.37(3H,t), 1.36–1.72(4H,m), 3.46–3.56(2H,m), 4.32(2H,q), 6.49(1H,dd), 7.97(1H,br), 8.11(1H,dd), 8.27(1H,dd). IR(neat)cm$^{-1}$: 3375, 1690, 1600, 1585, 1520, 1295, 1250, 1125.

b) Ethyl 2-[N-butyl-N-(2'-cyanobiphenyl-4-yl)methylamino]pyridine-3-carboxylate

Starting from the compound (2.4 g) obtained in Working Example 5 a), substantially the same procedure as in Working Example 3 a) was followed to afford the title compound as a colorless oil (2.4 g, 53%). $^1$H-NMR(200MHz,CDCl$_3$) δ: 0.85(3H,t), 1.17–1.31(2H,m), 1.37(3H,t), 1.48–1.63(2H,m), 3.33(2H,t), 4.33(2H,q), 4.78(2H,s), 6.70(1H,dd), 7.38–7.77(8H,m), 7.91(1H,dd), 8.26(1H,dd). IR(neat)cm$^{-1}$: 2230, 1715, 1590, 1560, 1480, 1445, 1410, 1370, 1285, 1250, 1225, 1125, 1085, 1060, 760.

c) Ethyl 2-[N-butyl-N-(2'-hydroxycarbamimidoylbiphenyl-4-yl)methylamino]pyridine-3-carboxylate Starting from the compound (2.4 g) obtained in Working Example 5 b), substantially the same procedure as in Working Example 3 b) was followed to afford the title compound as colorless prisms (1.0 g, 38%), m.p.181°–182° C. (chloroform-methanol).

| Elemental Analysis for $C_{26}H_{30}N_4O_3$: | | | |
|---|---|---|---|
| | C (%) | H (%) | N (%) |
| Calcd.: | 69.93; | 6.77; | 12.55 |
| Found: | 70.07; | 6.73; | 12.58 |

$^1$H-NMR(200MHz,CDCl$_{13}$) δ: 0.84(3H,t), 1.14–1.31(2H, m), 1.37(3H,t), 1.55(2H,m), 3.34(2H,t), 4.33(2H,q), 4.38(2H,s), 4.74(2H,s), 6.70 (1H,dd), 7.31–7.60(8H,m), 7.90(1H,q), 8.26(1H,dd). IR(KBr)cm$^{-1}$: 3480, 3360, 3220, 1680, 1660, 1580, 1560, 1460, 1430, 1380, 1365, 1305, 1285, 1260, 1220, 1130, 1120, 920, 780, 770.

d) Ethyl 2-[N-butyl-N-[2'-(2,5-dihydro-5-oxo-1,2,4-oxadiazol-3-yl)biphenyl-4-yl]methylamino]pyridine-3-carboxylate To a solution of the compound (0.5 g) obtained in Working Example 5 c) and triethylamine (0.44 g) in chloroform (15 ml) was added dropwise ethyl chloroformate (0.24 g). The reaction mixture was stirred for one hour at room temperature, which was then washed with water and dried over anhydrous magnesium sulfate. The solvent was distilled under reduced pressure, and the residue was dissolved in ethyl acetate (10 ml). The solution was heated with 1,5-diazabicyclo[5,4,0]undec-7-ene (0.67 g) for two hours under reflux. The reaction mixture was adjusted to pH 4–5, which was washed with water and dried over anhydrous magnesium sulfate. The solvent was distilled under reduced pressure. The residue was purified by column chromatography on silica gel. The resulting crude product was recrystallized from ethyl acetate-hexane to afford the title compound as colorless prisms (0.38 g, 73%), m.p.146°–147° C.

| Elemental Analysis for $C_{27}H_{28}N_4O_4$: | | | |
|---|---|---|---|
| | C (%) | H (%) | N (%) |
| Calcd.: | 68.63; | 5.97; | 11.86 |
| Found: | 68.78; | 6.04; | 11.88 |

$^1$H-NMR(200MHz,CDCl$_3$) δ: 0.84(3H,t), 1.13–1.27(2H,m), 1.37(3H,t), 1.47–1.6 2(2H,m), 3.29(2H,t), 4.32(2H,q), 4.70(2H,s), 6.69(1H,dd), 7.22–7.64(7H,m), 7.84–7.94(2H, m), 8.13(1H,dd). IR(KBr)cm$^{-1}$: 1775, 1720, 1585, 1565, 1495, 1480, 1455, 1440, 1365, 1280, 1250, 1220, 1170, 1120.

Working Example 6

2-[N-butyl-N-[2'-(2,5-dihydro-5-oxo-1,2,4-oxadiazol-3-yl) biphenyl-4-yl]methylamino]pyridine-3-carboxylic acid Starting from the compound (0.25 g) obtained in Working Example 5 d), substantially the same procedure as in Working Example 2 was followed to afford the title compound as a colorless powder (0.18 g, 75%), m.p.95°–98° C.

| Elemental Analysis for $C_{25}H_{24}N_4O_4 \cdot 0.5H_2O$: | | | |
|---|---|---|---|
| | C (%) | H (%) | N (%) |
| Calcd.: | 66.21; | 5.56; | 12.36 |
| Found: | 66.25; | 5.36; | 12.26 |

$^1$H-NMR(200MHz,CDCl$_3$) δ: 0.87(3H,t), 1.24–1.44(4H,m), 3.41(2H,t), 3.41(2H,t), 4.31(2H,s), 7.09(2H,q), 7.22(2H,d), 7.38–7.62(4H,m), 7.72(1H,dd), 8.46(1H,dd), 8.67(1H,dd). IR(KBr)cm$^{-1}$: 1780, 1600, 1585, 1495, 1470, 1430, 1375, 940, 760.

Working Example 7

Methyl 2-[N-[2'-(2,5-dihydro-5-oxo-1,2,4-oxadiazol-3-yl)biphenyl-4-yl]methyl-N-valerylamino]thiophene-3-carboxylate a) Methyl 2-valerylaminothiophene-3-carboxylate Valeryl chloride (1.3 g) was added to a solution of methyl 2-aminothiophene-3-carboxylate (1.6 g) [Y. Kuwada et al. Chem. Abst. 82, 156252(1975)] and triethylamine (1.2 g) in dichloroethane (20 ml) under ice-cooling. The mixture was stirred for two hours. The reaction mixture was washed with water and dried over anhydrous magnesium sulfate. The solvent was distilled under reduced pressure. The residue was purified by column chromatography on silica gel to afford the title compound as a colorless oil (2.3 g, 96%). $^1$H-NMR(200MHz,CDCl$_3$) δ: 0.96(3H,t), 1.33–1.52(2H,m), 1.68–1.83(2H,m), 2.51(2H,t), 3.89(3H,s), 6.72(1H,dd), 7.19(1H,d), 10.97(1H,brs). IR(neat)cm$^{-1}$: 3300, 1700, 1680, 1550, 1500, 1440, 1295, 1240, 1200, 1165, 1025, 700.

b) Methyl 2-[N-(2'-cyanobiphenyl-4-yl)methyl-N-valerylamino]thiophene-3-carboxylate Starting from the compound (2.3 g) obtained in Working Example 7 a), substantially the same procedure as in Working Example 3 a) was followed to afford the title compound as a colorless oil (4.0 g, 95%). $^1$H-NMR(200MHz,CDCl$_3$) δ: 0.85(3H,t), 1.17–1.36(2H,m), 1.54–1.69(2H,m), 2.19(2H,t), 3.74(3H,s), 4.53(2H,brs), 5.33(1H,d), 7.12(1H,d), 7.30–7.49(7H,m), 7.59–7.67(1H,m), 7.75(1H,dd). IR(neat)cm$^{-1}$: 2220, 1720, 1680, 1540, 1480, 1440, 1390, 1345, 1275, 1230, 1190, 1155, 1005, 765, 1720 c) Methyl 2-[N-(2'-hydroxycarbamimidoylbiphenyl-4-yl)methyl-N-valerylamino]thiophene-3-carboxylate Starting from the compound (4.0 g) obtained in Working Example 7 b), substantially the same procedure as in Working Example 3 b) was followed to afford the title compound as a colorless oil (1.5 g, 35%). $^1$H-NMR(200MHz,CDCl$_3$) δ: 0.85(3H,t), 1.17–1.36(2H,m), 1.54–1.69(2H,m), 2.19(2H,t), 3.69(3H,s), 4.45(2H,brs), 4.83(1H,d), 4.99(1H,d), 7.14(1H,d), 7.20(2H,d), 7.32–7.59(7H,m). IR (neat) cm$^{-1}$: 1720, 1650, 1580, 1540, 1440, 1390, 1340, 1270, 1230 1190, 1155, 1005, 750, 715.

d) Methyl 2-[N-[2'-(2,5-dihydro-5-oxo-1,2,4-oxadiazol-3-yl)biphenyl-4-yl]methyl-N-valerylamino]thiophene-3-carboxylate Starting from the compound (0.7 g) obtained in Working Example 7 c), substantially the same procedure as in Working Example 5 d) was followed to afford the title compound as colorless prisms (0.50 g, 68%), m.p.154°–155° C. (ethyl acetate - hexane).

Elemental Analysis for C$_{26}$H$_{25}$N$_3$O$_5$S:

|  | C (%) | H (%) | N (%) |
| --- | --- | --- | --- |
| Calcd.: | 63.53; | 5.13; | 8.55 |
| Found: | 63.61; | 5.23; | 8.74 |

$^1$H-NMR(200MHz,CDCl$_3$) δ: 0.86(3H,t), 1.19–1.38(2H,m), 1.56–1.71(4H,m), 2.25(2H,t), 3.73(3H,s), 4.77(1H,d), 5.08(1H,d), 7.13–7.29(5H,m), 7.43–7.67(4H,m), 7.89(1H, dd), 8.23(1H,brs). IR(KBr)cm$^{-1}$: 1765, 1715, 1650, 1460, 1435, 1400, 1270, 1250, 1220, 1180, 1160, 940, 760, 730.

Working Example 8

2-[N-[2'-(2,5-dihydro-5-oxo-1,2,4-oxadiazol-3-yl)biphenyl-4-yl]methyl-N-valerylamino]thiophene-3-carboxylic acid Starting from the compound (0.30 g) obtained in Working Example 7 d), substantially the same procedure as in Working Example 2 was followed to afford the title compound as colorless prisms (0.20 g, 67%), m.p.183°–185° C. (decomp.) (chloroform-ether).

Elemental Analysis for C$_{25}$H$_{23}$N$_3$O$_5$S.H$_2$O:

|  | C (%) | H (%) | N (%) |
| --- | --- | --- | --- |
| Calcd.: | 60.59; | 5.08; | 8.48 |
| Found: | 60.56; | 4.80; | 8.39 |

$^1$H-NMR(200MHz,CDCl$_3$) δ: 0.86(3H,t), 1.16–1.38(2H,m), 1.56–1.71(2H,m), 2.17–2.34(2H,t), 3.79(1H,d), 6.00(1H,d), 7.15–7.68(9H,m), 7.92(1H,dd), 9.10(1H,brs). IR(KBr)cm$^{-1}$ 1770, 1680, 1640, 1450, 1435, 1395, 1280, 1240, 760, 720.

Working Example 9

Methyl 2-[N-[2,-(2,5-dihydro-5-oxo-1,2,4-thiadiazol-3-yl)biphenyl-4-yl]methyl-N-valerylamino]thiophene3-carboxylate Starting from the compound (0.80 g) obtained in Working Example 7 c), substantially the same procedure as in Working Example 3 c) was followed to afford the title compound as colorless prisms (0.40 g, 47%), m.p.116°–117° C. (ethyl acetate - hexane).

Elemental Analysis for C$_{26}$H$_{25}$N$_3$O$_4$S$_2$:

|  | C (%) | H (%) | N (%) |
| --- | --- | --- | --- |
| Calcd.: | 61.52; | 4.96; | 8.28 |
| Found: | 61.43; | 4.94; | 8.31 |

$^1$H-NMR(200MHz,CDCl$_3$) δ: 0.85(3H,t), 1.17–1.36(2H,m), 1.46–1.69(2H,m), 2.18(2H,t), 3.80(3H,s), 4.31(1H,d), 5.56(1H,d), 7.15(1H,d 7.27(4H,s-like), 7.36–7.62(4H,m), 7.92(1H,dd), 8.22(1H,brs). IR(KBr)cm$^{-1}$: 1680 1660, 1540, 1435, 1395, 1270, 1250, 1155, 760, 720.

Working Example 10

2-[N-[2'-(2,5-dihydro-5-oxo-1,2,4-thiadiazol-3-yl)biphenyl-4-yl]methyl-N-valerylamino]thiophene-3-carboxylic acid Starting from the compound (0.25 g) obtained in Working Example 9, substantially the same procedure as in Working Example 2 was followed to afford the title compound as colorless crystals (87 mg, 33%), m.p.148°–149° C. (chloroform-ether).

Elemental Analysis for C$_{25}$H$_{23}$N$_3$O$_4$S$_2$.0.25CHCl$_3$:

|  | C (%) | H (%) | N (%) |
| --- | --- | --- | --- |
| Calcd.: | 57.94; | 4.48; | 8.03 |
| Found: | 57.92; | 4.45; | 7.98 |

$^1$H-NMR(200MHz,CDCl$_3$) δ: 0.87(3H,t), 1.21–1.40(2H,m), 1.57–1.72(2H,m), 2.17–2.40(2H,t), 3.75 (1H,d), 6.03(1H,d), 7.03–7.20 (5H,m), 7.34 (1H,d), 7.40–7.61(3H,m), 7.93(1H, dd), 10.06(1H,brs) IR(KBr)cm$^{-1}$: 1700, 1680, 1535, 1455, 1430, 1395, 1280, 1260, 1180, 760, 720.

Working Example 11

Methyl 5-methyl-2-[N-butyryl-N-[2'-(2,5-dihydro-5-oxo-1,2,4-oxadiazol-3-yl)biphenyl-4-yl]methylamino]thiophene-3-carboxylate a) Methyl 2-butyrylamino-5-methylthiophene-3-carboxylate

To a solution of methyl 2-amino-5-methylthiophene-3-carboxylate (2.6 g) [(Y. Kuwada et al. Chem. Abst. 82, 156252 (1975)] in pyridine (20 ml) was added dropwise under ice-cooling butyric anhydride (2.8 g). The reaction mixture was stirred for 18 hours at 60° C. The reaction mixture was concentrated and dissolved in ethyl acetate. The solution was washed with water, which was dried over anhydrous magnesium sulfate. The solvent was distilled off, and the residue was purified by column chromatography on silica gel to afford the title compound as a brownish oil (2.2 g, 62%). $^1$H-NMR(200MHz,CDCl$_3$) δ: 1.01(3H,t), 1.69–1.88(2H,m), 2.37(3H,d), 2.46(2H,t), 3.86(3H,s), 6.82(1H,t), 10.86(1H,brs). IR(neat)cm$^{-1}$: 3300, 1670, 1560, 1540, 1450, 1385, 1275, 1230, 1200, 1175.

b) Methyl 5-methyl-2-[N-butyryl-N-(2'-cyanobiphenyl-4-yl)methylamino]thiophene-3-carboxylate Starting from the compound (2.2 g) obtained in Working Example 11 a), substantially the same procedure as in Working Example 3 a) was followed to afford the title compound as a yellowish oil (3,9 g, 100%). $^1$H-NMR(200MHz),CDCl$_3$) δ: 0.89(3H,t), 1.61–1.72(2H,m), 2.20(2H,t), 2.40(3H,d), 3.70(3H,s), 4.55(1H,d), 5.27(1H,d), 7.03(1H,d), 7.35(2H,d),7.40–7.52(4H,m), 7.64(1H,dt), 7.76(1H,dd). IR(neat)cm$^{-1}$: 2220, 1720, 1675, 1440, 1390, 1250, 1190, 1165, 760.

c) Methyl 5-methyl-2-[N-butyryl-N-(2'-hydroxycarbamimidoylbiphenyl-4-yl)methylamino]thiophene-3-carboxylate Starting from the compound (3.0 g) obtained in Working Example 11 b), substantially the same procedure as in Working Example 3 b) was followed to afford the title compound as a colorless oil (1.7 g, 53%). $^1$H-NMR(200MHz,CDCl$_3$) δ: 0.89(3H,t), 1.60–1.72(2H,m), 2.20(2H,t), 2.41(3H,d), 3.65(3H,s), 4.45(2H,brs), 4.88(2H,s), 6.99(1H,t), 7.22(2H,d), 7.35–7.61(7H,m). IR (neat) cm$^{-1}$: 3480, 3370, 1720, 1660, 1580, 1560, 1490, 1440, 1380, 1340, 1250, 1190, 1165, 1005, 760 d) Methyl 5-methyl-2-[N-butyryl-N-[2'-(2,5-dihydro-5-oxo-1,2,4-oxadiazol-3-yl)biphenyl-4-yl]methylamino]thiophene-3-carboxylate Starting from the compound (0.70 g) obtained in Working Example 11 c), substantially the same procedure as in Working Example 5 d) was followed to afford the title compound as colorless needles (0.45 g, 61%), m.p.156°–157° C. (ethyl acetate - hexane).

Elemental Analysis for C$_{26}$H$_{25}$N$_3$O$_5$S:

|  | C (%) | H (%) | N (%) |
|---|---|---|---|
| Calcd.: | 63.53; | 5.13; | 8.55 |
| Found: | 63.33; | 5.08; | 8.34 |

$^1$H-NMR(200MHz,CDCl$_3$) δ: 0.91(3H,t) 1.68(2H,m), 2.26(2H,t), 2.44(3H,d), 3.66(3H,s), 4.52(1H,d), 5.24(1H,d), 7.09–7.29(5H,m), 7.43–7.54(2H,m), 7.63(1H,dd), 7.87(1H,dd), 8.45(1H,brs). IR(KBr)cm$^{-1}$: 1760, 1715, 1645, 1490, 1460, 1440, 1400, 1390, 1380, 1250, 1235, 1190, 1160, 940, 760.

Working Example 12

5-Methyl-2-[N-butyryl-N-[2'-(2,5-dihydro-5-oxo-1,2,4-oxadiazol-3-yl)biphenyl-4-yl]methylamino]thiophene-3-carboxylic acid Starting from the compound (0.25 g) obtained in Working Example 11 d), substantially the same procedure as in Working Example 2 was followed to afford the title compound as colorless prisms (0.17 g, 71%), m.p.210°–211° C. (decomp.) (ethyl acetate-hexane).

Elemental Analysis for C$_{25}$H$_{23}$N$_3$O$_5$S:

|  | C (%) | H (%) | N (%) |
|---|---|---|---|
| Calcd.: | 62.88; | 4.85; | 8.80 |
| Found: | 62.65; | 4.92; | 8.62 |

$^1$H-NMR(200MHz,CDCl$_3$) δ: 0.89(3H,t), 1.57–1.76(2H,m), 2.22–2.35(2H,m), 2.50(3H,d), 3.76(1H,d), 5.95(1H,d), 6.80(1H,m), 7.20(4H,s-like), 7.41–7.55(2H,m), 7.62(1H,dd), 7.90(1H,dd), 9.20(1H,brs). IR(KBr)cm$^{-1}$: 1760, 1680, 1600, 1560, 1495, 1470, 1460, 1375, 1340, 1270, 1255, 1240, 1180, 1005, 995, 950, 840, 780, 760, 740, 725.

Working Example 13

Methyl 5-methyl-2-[N-butyryl-N-[2'-(2,5-dihydro-5-oxo-1,2,4-thiadiazol-3-yl)biphenyl-4-yl]methylamino]thiophene-3-carboxylate Starting from the compound (0.90 g) obtained in Working Example 11 c), substantially the same procedure as in Working Example 3 c) was followed to afford the title compound as colorless prisms (0.34 g, 35%), m.p.131°–132° C. (ethyl acetate - hexane).

Elemental Analysis for C$_{26}$H$_{25}$N$_3$O$_4$S$_2$:

|  | C (%) | H (%) | N (%) |
|---|---|---|---|
| Calcd.: | 61.52; | 4.96; | 8.28 |
| Found: | 61.38; | 4.98; | 8.17 |

$^1$H-NMR(200MHz,CDCl$_3$) δ: 0.88(3H,t), 1.66(2H,m), 2.19(2H,t), 2.41(3H,d), 3.75(3H,s), 4.41(1H,d), 5.39(1H,d), 7.04(1H,m), 7.17–7.62(7H,m), 7.90(1H,dd), 8.35(1H,brs). IR(KBr)cm$^{-1}$: 1720, 1690, 1660, 1555, 1485, 1460, 1435, 1400, 1345, 1250, 1225, 1190, 1165, 1005, 760.

Working Example 14

5-Methyl-2-[N-butyryl-N-[2'-(2,5-dihydro-5-oxo-1,2,4-thiadiazol-3-yl)biphenyl-4-yl]methylamino]thiophene-3-carboxylic acid Starting from the compound (0.20 g) obtained in Working Example 13, substantially the same procedure as in Working Example 2 was followed to afford the title compound as colorless prisms (0.15 g, 83%), m.p.193°–195° C. (decomp.) (ethyl acetate-hexane).

| Elemental Analysis for $C_{25}H_{23}N_3O_4S_2$: | | | |
|---|---|---|---|
| | C (%) | H (%) | N (%) |
| Calcd.: | 60.83; | 4.70; | 8.51 |
| Found: | 60.74; | 4.80; | 8.35 |

$^1$H-NMR(200MHz,CDCl$_3$) δ: 0.91(3H,t), 1.55–1.78(2H,m), 2.27–2.46(2H,m), 2.50(3H,d), 3.70(1H,d), 6.01(1H,d), 6.75(1H,m), 7.06(2H,d), 7.17(2H,d), 7.40–7.62(3H,m), 7.92(1H,dd), 10.09(1H,brs). IR(KBr)cm$^{-1}$: 1680, 1555, 1490, 1460, 1435, 1380, 1340, 1260, 1240, 1180, 760, 720.

Working Example 15

Ethyl 4-[N-butyl-N-[2'-(2,5-dihydro-5-oxo-1,2,4-oxadiazol- 3-yl)biphenyl-4-yl]methyl]aminopyrimidine-5-carboxylate a) 4'-Butylaminomethyl-2-cyanobiphenyl To a solution of 4'-bromomethyl-2-cyanobiphenyl (10.0 g) in tetrahydrofuran (100 ml) was added butylamine (26.8 g). The mixture was stirred for 3 hours at room temperature. The reaction mixture was concentrated and diluted with water, followed by extraction with chloroform. The extract was washed with water and dried. The solvent was distilled under reduced pressure. The residue was purified by column chromatography on silica gel to afford the title compound as a pale yellow oil (10.7 g, quantitatively). $^1$H-NMR(200MHz,CDCl$_3$) δ: 0.93(3H,t), 1.28–1.60(4H,m), 2.68(2H,t), 3.86(2H,s), 7.39–7.56(6H,m), 7.64(1H,dt), 7.76(1H,dd). IR(neat)cm$^{-1}$: 2220, 1480, 760 b) Ethyl 4-chloropyrimidine-5-carboxylate

To a mixture of ethyl 3,4-dihydro-4-oxopyrimidine-5-carboxylate (3.54 g) (synthesized according to the method reported by A. R. Todd and F. Bergel on J. Chem. Soc., 364 (1937)) and triethylamine (2.13 g) was added dropwise under ice-cooling phosphorus oxychloride (21 ml), and the mixture was then heated for 1.5 hour under reflux. The reaction mixture was concentrated to dryness, which was poured into ice-water, followed by partitioning between chloroform and a saturated aqueous solution of sodium hydrogencarbonate. The organic layer was washed with a saturated aqueous solution of sodium hydrogencarbonate and then dried. The solvent was distilled under reduced pressure. The residue was purified by column chromatography on silica gel to afford the title compound as a pale yellow oil (3.42 g, 86%). $^1$H-NMR(200MHz, CDCl$_3$) δ: 1.44(3H,t), 4.47(2H,q), 9.08(1H,s), 9.13(1H,s).

c) Ethyl 4-[N-butyl-N-(2'-cyanobiphenyl-4-yl)methyl]aminopyrimidine-5-carboxylate To a solution of the compound (5.53 g) obtained in Working Example 15 b) and triethylamine (6.34 g) in tetrahydrofuran (50 ml) was added a solution of the compound (3.90 g) obtained in Working Example 15 a) in tetrahydrofuran (20 ml). The mixture was stirred for two hours at room temperature. The reaction mixture was diluted with water, which was extracted with ethyl acetate. The extract solution was washed with water and dried, followed by distilling off the solvent under reduced pressure. The reside was purified by column chromatography on silica gel to afford-the title compound as a pale yellow oil (8.77 g, quantitatively). $^1$H-NMR(200MHz,CDCl$_3$) δ: 0.89(3H,t), 1.81–1.36(5H,m), 1.54–1.69(2H,m), 3.47(2H,t), 4.29(2H,q), 4.88(2H,s), 7.34(2H,d), 7.40–7.78(6H,m), 8.59(1H,s), 8.63(1H,s). IR(neat)cm$^{-1}$: 2230, 1751, 1575, 1535, 1145, 765.

d) Ethyl 4-[N-butyl-N-(2'-hydroxycarbamimidoylbiphenyl-4-yl)methylamino]pyrimidine-5-carboxylate Starting from the compound (4.00 g) obtained in Working Example 15 c), substantially the same procedure as in Working Example 3 b) was followed to afford the title compound as a pale yellow oil (0.82 g, 11%). $^1$H-NMR(200MHz,CDCl$_3$) δ: 0.89(3H,t), 1.21–1.37(2H,m), 1.33(3H,t), 1.53–1.68(2H,m), 3.48(2H,t), 4.29(2H,s), 4.41(2H,brs), 4.84(2H,s), 7.22–7.60(8H,m), 8.59(1H,s), 8.62(1H,s). IR(neat)cm$^{-1}$: 1730, 1715, 1575, 1540, 1370, 1240, 1145.

e) Ethyl 4-[N-butyl-N-[2'-(2,5-dihydro-5-oxo-1,2,4-oxadiazol-3-yl)biphenyl-4-yl]methylamino] pyrimidine-5-carboxylate Starting from the compound (0.78 g) obtained in Working Example 15 c), substantially the same procedure as in Working Example 5 d) was followed to afford the title compound as a colorless powder (0.30 g, 35%), m.p.65°–69° C.

| Elemental Analysis for $C_{26}H_{27}N_5O_4 \cdot 0.3H_2O$: | | | |
|---|---|---|---|
| | C (%) | H (%) | N (%) |
| Calcd.: | 65.20 | 5.81 | 14.62 |
| Found: | 65.16 | 5.96 | 14.32 |

$^1$H-NMR(200MHz,CDCl$_3$) δ: 0.89(3H,t), 1.21–1.36(2H,m), 1.34(3H,t), 1.52–1.67(2H,m), 3.44(2H,t), 4.29(2H,q), 4.83(2H,s), 7.26(4H,s-like), 7.42(1H,dd), 7.51(1H,dt), 7.62(1H,dt), 7.83(1H,dd), 8.40(1H,s), 8.43(1H,s). IR(KBr)cm$^{-1}$: 1780, 1730, 1715. 1590, 1540, 1505, 1495, 1475, 1460, 1285, 1240, 1145, 1075, 935 765.

Working Example 16

4-[N-butyl-N-[2'-(2,5-dihydro-5-oxo-1,2,4-oxadiazol-3-yl)biphenyl-4-yl]methylamino]pyrimidine-5-carboxylic acid To a suspension of the compound (0.28 g) obtained in Working Example 15 e) in tetrahydrofuran (8 ml) -water (4 ml) was added lithium hydroxide hydrate (0.17 g). The mixture was stirred for 24 hours at 70° C. The reaction mixture was adjusted at pH 4 with 1N HCl followed by extraction with ethyl acetate. The extract solution was washed with water and dried. The solvent was distilled under reduced pressure. Resulting crystals were recrystallized from chloroform—methanol —hexane to afford the title compound as a colorless crystal (0.12 g, 46%), m.p.143°–147° C. (decomp.).

| Elemental Analysis for $C_{24}H_{23}N_5O_4 \cdot 0.5H_2O$: | | | |
|---|---|---|---|
| | C (%) | H (%) | N (%) |
| Calcd.: | 63.43 | 5.32 | 15.41 |
| Found: | 63.67 | 5.23 | 15.53 |

$^1$H-NMR(200MHz,DMSO-d$_6$) δ: 0.83(3H,t), 1.10–1.62(2H, m), 1.47–1.62(2H,m), 3.42(2H,t), 4.89(2H,s), 7.29(4H,s-like), 7.51–7.73(4H,m), 8.49(1H,s), 8.56(1H,s). IR(KBr)cm$^{-1}$: 1775, 1635, 1585, 1545, 1535, 1345, 765.

Working Example 17

Ethyl 4-[N-[[2'-(2,5-dihydro-5-oxo-1,2,4-oxadiazol-3-yl)biphenyl-4-yl]methyl]-N-propylamino]-2-methylpyrimidine-5-carboxylate a) 4'-Propylaminomethyl-2-cyanobiphenyl

Starting from 4'-bromomethyl-2-cyanobiphenyl (5.4 g), substantially the same procedure as in Working Example 15 a) was followed to afford the title compound as a pale yellow oil (4.8 g, 96%). $^1$H-NMR(200MHz,CDCl$_3$) δ: 0.95(3H,t), 1.47–1.66(2H,m), 2.65(2H,t), 3.86(2H,s), 7.38–7.78(8H,m). IR(neat)cm$^{-1}$: 2220, 1480, 1460, 1440, 760 b) Ethyl 4-[N-[(2'-cyanobiphenyl-4-yl)methyl]-N-Propylamino]-2-methylpyrimidine-5-carboxylate To a solution of ethyl 3,4-dihydro-4-oxo-2-methylpyrimidine-5-carboxylate (3.45 g) (synthesized according to the method reported by A. R. Todd and F. Bergel on J. Chem. Soc., 364(1937)) and triethylamine (4.78 g) in N,N-dimethylformamide (30 ml) was added p-toluenesulfonyl chloride (3.78 g). The mixture was stirred for 30 minutes at room temperature. To the reaction mixture was added a solution of the compound (4.30 g) obtained in Working Example 17 a) in toluene (5 ml), and the mixture was stirred for 16 hours at room temperature. The reaction mixture was concentrated under reduced pressure. The residue was diluted with water, followed by extraction with ethyl acetate. The extract was washed with water and dried. The solvent was distilled under reduced pressure. The residue was purified by column chromatography on silica gel to afford the title compound as a yellow oil (4.99 g, 70%). $^1$H-NMR(200MHz,CDCl$_3$) δ: 0.85(3H,t), 1.32(3H,t), 1.54–1.74(2H,m), 2.54(3H,s), 3.40(2H,t), 4.28(2H,q), 4.89(2H,s), 7.34–7.78(8H,m), 8.54(1H,s). IR(neat)cm$^{-1}$: 1715, 1575, 1540, 1535, 1510, 1435, 1090, 760.

c) Ethyl 4-[N-[(2'-hydroxycarbamimidoylbiphenyl-4-yl)methyl]-N-propylamino]-2-methylpyrimidine-5-carboxylate Starting from the compound (4.49 g) obtained in Working Example 17 b), substantially the same procedure as in Working Example 3 b) was followed to afford the title compound as a colorless powder (2.49 g, 51%). $^1$H-NMR(200MHz,CDCl$_3$) δ: 0.84(3H,t), 1.32(3H,t), 1.54–1.72(2H,m), 2.53(3H,s), 3.41(2H,t), 4.28(2H,q), 4.41(2H,s), 4.85(2H,s), 7.24–7.59(8H,m), 8.53(1H,s).

d) Ethyl 4-[N-[[2'-(2,5-dihydro-5-oxo-1,2,4-oxadiazol-3-yl)biphenyl-4-yl]methyl]-N-propylamino]-2-methylpyrimidine-5-carboxylate Starting from the compound (0.80 g) obtained in Working Example 17 c), substantially the same procedure as in Working Example 5 d) was followed to afford the title compound as pale yellow needles (0.60 g, 70%), m.p.176°–177° C. (ethyl acetate-hexane).

| Elemental Analysis for C$_{26}$H$_{27}$N$_5$O$_4$: | | | |
|---|---|---|---|
| | C (%) | H (%) | N (%) |
| Calcd.: | 65.95 | 5.75 | 14.79 |
| Found: | 65.88 | 5.78 | 14.56 |

$^1$H-NMR(200MHz,CDCl$_3$) δ: 0.82(3H,t), 1.32(3H,t), 1.50–1.68(2H,m), 2.28(3H,s), 3.33(2H,t), 4.28(2H,q), 4.83(2H,s), 7.19(4H,s-like), 7.41(1H,dd), 7.52(1H,dt), 7.62(1H,dt), 7.83(1H,dd), 8.06(1H,s). IR(KBr)cm$^{-1}$: 1780, 1725, 1715, 1585, 1535, 1440, 1430, 1260, 1090, 765.

Working Example 18

4-[N-[[2'-(2,5-dihydro-5-oxo-1,2,4-oxadiazol-3-yl)biphenyl-4-yl]methyl]-N-propylamino]-2-methylpyrimidine-5-carboxylic acid Starting from the compound (0.45 g) obtained in Working Example 17 d), substantially the same procedure as in Working Example 2 was followed to afford the title compound as colorless crystals (0.40 g, 87%), m.p.182°–186° C. (chloroform-methanol).

| Elemental Analysis for C$_{24}$H$_{23}$N$_5$O$_4$·0.5H$_2$O: | | | |
|---|---|---|---|
| | C (%) | H (%) | N (%) |
| Calcd.: | 63.43 | 5.32 | 15.41 |
| Found: | 63.55 | 5.40 | 15.29 |

$^1$H-NMR(200MHz,DMSO-d$_6$) δ: 0.76(3H,t), 1.45–1.64(2H,m), 2.41(3H,s), 3.38(2H,t), 4.88(2H,s), 7.27(2H,d), 7.33(2H,d), 7.50–7.74(4H,m), 8.42(1H,s). IR(KBr)cm$^{-1}$: 1775, 1635, 1585, 1545, 1535, 1345, 765.

Working Example 19

Ethyl 4-[N-[[2'-(2,5-dihydro-5-oxo-1,2,4-thiadiazol-3-yl)biphenyl-4-yl]methyl]-N-propylamino]-2-methylpyrimidine-5-carboxylate Starting from the compound (0.80 g) obtained in Working Example 17 c), substantially the same procedure as in Working Example 3 c) was followed to afford the title compound as colorless needles (91 mg), m.p.173°–175° C. (ethyl acetate-hexane).

| Elemental Analysis for C$_{26}$H$_{27}$N$_5$O$_3$S: | | | |
|---|---|---|---|
| | C (%) | H (%) | N (%) |
| Calcd.: | 63.78 | 5.56 | 14.30 |
| Found: | 63.51 | 5.72 | 14.02 |

$^1$H-NMR(200MHz,CDCl$_3$) δ:0.83(3H,t), 1.33(3H,t), 1.50–1.69(2H,m), 2.41(3H,s), 3.33(2H,t), 4.28(2H,q), 4.87(2H,s), 7.19(2H,d), 7.28(2H,d), 7.38 (1H,dd), 7.46–7.61(2H,m), 7.85(1H,dd), 8.27(1H,s). IR(KBr)cm$^{-1}$: 1720, 1700, 1585, 1540, 1450, 1435, 1260, 1090.

Working Example 20

4-[N-[[2'-(2,5-dihydro-5-oxo-1,2,4-thiadiazol-3-yl)-biphenyl-4-yl]methyl]-N-propylamino]-2-methylpyrimidine-5-carboxylic acid Starting from the compound (0.07 g) obtained in Working Example 19, substantially the same procedure as in Working Example 16 was followed to afford the title compound as colorless crystals (55 mg, 81%), m.p. 219°–220° C. (decomp.).

Elemental Analysis for $C_{24}H_{23}N_5O_3S \cdot H_2O$:

|  | C (%) | H (%) | N (%) |
|---|---|---|---|
| Calcd.: | 60.11 | 5.25 | 14.60 |
| Found: | 59.95 | 5.08 | 14.56 |

$^1$H-NMR(200MHz,DMSO-d$_6$) δ: 0.76(3H,t), 1.44–1.62(2H, m), 2.41(3H,s), 3.35(2H,t), 4.85(2H,s), 7.20(2H,d), 7.29(2H,d), 7.46–7.66(4H,m), 8.42(1H,s). IR(KBr)cm$^{-1}$: 1685, 1640, 1535, 1340.

Working Example 21

Ethyl 4-[N-[[2'-(2,5-dihydro-5-thioxo-1,2,4-oxadiazol-3-yl)biphenyl-4-yl]methyl]-N-propylamino]-2-methylpyrimidine-5-carboxylate To a solution of the compound (0.40 g) obtained in Working Example 17 c) in acetonitrile (10 ml) were added 1,1'-thiocarbonyldiimidazole (0.24 g) and 1,8-diazabicyclo[5.4.0]-7-undecene (0.54 g). The mixture was stirred for one hour at room temperature. The reaction mixture was diluted with water and adjusted to pH4 with 1N HCl followed by extraction with ethyl acetate. The extract was washed with a saturated aqueous saline solution and dried. The solvent was distilled under reduced pressure. The residue was purified by column chromatography on silica gel. Recrystallization of thus obtained crude crystals from ethyl acetate-hexane afforded the title compound as pale yellow needles (0.26 g), m.p.170°–172° C.

Elemental Analysis for $C_{26}H_{27}N_5O_3S \cdot 0.5H_2O$:

|  | C (%) | H (%) | N (%) |
|---|---|---|---|
| Calcd.: | 62.63 | 5.66 | 14.05 |
| Found: | 62.96 | 5.59 | 13.81 |

$^1$H-NMR(200MHz,CDCl$_3$) δ: 0.83(3H,t), 1.34(3H,t), 1.47–1.65(2H,m), 2.08(3H,s), 3.30(2H,t), 4.35(2H,q), 4.70(2H,s), 7.03(2H,d), 7.14(2H,d), 7.45–7.68(3H,m), 7.81–7.84(1H,m), 8.00(1H,s). IR(KBr)cm$^{-1}$: 1725, 1590, 1545, 1535, 1450, 1340, 1305, 1255, 1090.

Working Example 22

4-[N-[[2'-(2,5-dihydro-5-thioxo-1,2,4-oxadiazol-3-yl)biphenyl-4-yl]methyl]-N-propylamino]-2-methylpyrimidine-5-carboxylic acid Starting from the compound (0.20 g) obtained in Working Example 21, substantially the same procedure as in Working Example 2 was followed to afford the title compound as colorless crystals (0.14 g), m.p.212°–214° C. (decomp.) (chloroform-methanol).

Elemental Analysis for $C_{24}H_{23}N_5O_3S \cdot 0.8H_2O$:

|  | C (%) | H (%) | N (%) |
|---|---|---|---|
| Calcd.: | 60.57 | 5.21 | 14.71 |
| Found: | 60.73 | 5.11 | 14.80 |

$^1$H-NMR(200MHz,DMSO-d$_6$) δ: 0.78(3H,t), 1.48–1.66(2H, m), 2.45(3H,s), 3.42(2H,t), 4.91(2H,s), 7.23(2H,d), 7.31(2H,d), 7.47–7.57(2H,m), 7.62–7.70(2H,m), 8.50(1H, s). IR(KBr)cm$^{-1}$: 1640, 1540, 1490, 1340, 1295, 775.

Working Example 23

Ethyl 3-[N-[[2'-(2,5-dihydro-5-oxo-1,2,4-oxadiazol-3-yl)biphenyl-4-yl]methyl]-N-propylamino]-1-methylpyrazole-4-carboxylate a) Ethyl 3-[N-(2'-cyanobiphenyl-4-yl)methylamino]-1-methylpyrazole-4-carboxylate To a mixture of ethyl 3-amino-1-methylpyrazole-4-carboxylate (P. Schmidt et al. Hel. Chim. Acta., 1959, 41, 349.) (2.30 g) and potassium carbonate in N,N-dimethylformamide (70 ml), was added portionwise 4-bromomethyl-2'-cyanobiphenyl (4.81 g). The solvent was distilled under reduced pressure. To the residue was added ice-water and an aqueous solution of potassium carbonate. The mixture was extracted with ethyl acetate. The extract was washed with water and a saturated aqueous saline solution, which was dried over magnesium sulfate. The solvent was distilled off under reduced pressure to give crude crystals, which were recrystallization from ethyl acetate-isopropylether to afford the title compound as white crystals (3.7 g, 76%), m.p.151°–152° C.

Elemental Analysis for $C_{21}H_{20}N_4O_2$:

|  | C (%) | H (%) | N (%) |
|---|---|---|---|
| Calcd.: | 69.98; | 5.59; | 15.55 |
| Found: | 69.72; | 5.62; | 15.29 |

$^1$H-NMR(200MHz,CDCl$_3$) δ: 1.32(3H,t), 3.74(3H,s), 4.25(2H,q), 4.58(2H,d), 5.73(1H,bd), 7.33–7.70(8H,m), 7.75 (1H,d). IR(nujol)cm$^{-1}$: 3390, 2220, 1685, 1565, 1555, 1365, 1245, 1160, 1120.

b) Ethyl 3-[N-(2'-cyanobiphenyl-4-yl)methyl-N-propylamino]-1-methylpyrazole-4-carboxylate To a solution of diisopropylamine (1.05 ml) in tetrahydrofuran (10 ml) was added at –10° C. n-butyl lithium (1.6M hexane solution, 4.1 ml). The mixture was stirred for 30 minutes at –10° C. —5° C. To the reaction mixture was added dropwise at –78° C. a solution of the compound (1.80 g) obtained in Working Example 23 a) in tetrahydrofuran (15 ml). The reaction mixture was stirred for 30 minutes, to which was added dropwise at the same temperature a solution of propyl iodide (0.73 ml) in tetrahydrofuran (3 ml). The reaction mixture was allowed to warm to room temperature. The reaction mixture was stirred for further two hours, which was poured into a saturated aqueous solution of ammonium chloride, followed by extraction with ethyl acetate. The extract was washed with water and a saturated aqueous saline solution, followed by drying over magnesium sulfate. The solvent was distilled under reduced pressure. The residue was purified by column chromatography on silica gel to afford the title compound as an oil (1.75 g, 87%). $^1$H-NMR(200MHz,CDCl$_3$) δ: 0.84(3H,t), 1.30(3H,t), 1.50–1.75(2H,m), 3.18–3.33(2H,s), 3.75(3H,s), 4.14(2H,q), 4.62(2H,s), 7.36–7.80(9H,m). IR(neat)cm$^{-1}$: 2960, 2220, 1700, 1550, 1500, 1475, 1440, 1365, 1300, 1245, 1160, 1090.

c) Ethyl 3-[N-(2'-hydroxycarbamimidoylbiphenyl-4-yl)methyl-N-propylamino]-1-methylpyrazole-4-carboxylate Starting from the compound (1.80 g) obtained in Working Example 23 b), substantially the same procedure as in Working Example 3 b) was followed to afford the title compound as colorless crystals (1.08 g, 55%), m.p.171°–173° C. (recrystallized from ethyl acetate-isopropylether).

| Elemental Analysis for C$_{24}$H$_{29}$N$_5$O$_3$.0.2H$_2$O: | | | |
|---|---|---|---|
| | C (%) | H (%) | N (%) |
| Calcd.: | 65.64; | 6.75; | 15.96 |
| Found: | 65.97; | 6.90; | 15.62 |

$^1$H-NMR(200MHz,CDCl$_3$) δ: 0.82(3H,t), 1.30(3H,t), 1.46–1.69(2H,m), 3.14–3.28(2H,m), 3.73(3H,s), 4.23(2H,q), 4.40(2H,bds), 4.59(2H,s), 7.29–7.62(8H,m), 7.74(1H,s). IR(neat)cm$^{-1}$: 3470, 3350, 1680, 1640, 1595, 1545, 1495, 1255, 1190, 1100, 920, 770.

d) Ethyl 3-[N-(2'-methoxycarbonyloxycarbamimidoylbiphenyl-4-yl)methyl-N-propylamino]-1-methylpyrazole-4-carboxylate To a solution of the compound (0.68 g) of the working Example 23 c) and triethylamine was added in tetrahydrofuran at 0° C. methyl chlorocarbonate. The mixture was stirred for two hours at room temperature. The solvent was distilled under reduced pressure. To the residue was added ethyl acetate (20 ml), which was washed with water and a saturated aqueous saline solution, followed by drying over magnesium sulfate. The solvent was distilled under reduced pressure, and the residue was purified by column chromatography on silica gel to afford the title compound as a powder (0.72 g, 93%). $^1$H-NMR(200MHz,CDCl$_3$) δ: 0.82(3H,t), 1.30(3H,t), 1.48–1.75(2H,m), 3.22(2H,t-like), 3.75(3H,s), 3.90(3H,s), 4.24(2H,q), 4.59(4H,bds), 7.28–7.57(7H,m), 7.65(1H,d), 7.76(1H,s). IR(KBr)cm$^{-1}$: 3470, 3340, 2950, 1760, 1700, 1630, 1550, 1500, 1390, 1235, 1160.

e) Ethyl 3-[N-[2'-(2,5-dihydro-5-oxo-1,2,4-oxadiazol-3-yl)biphenyl-4-yl]methyl-N-Propylamino]-1-methylpyrazole-4-carboxylate A solution of the compound (0.70 g) of working Example 23 d) and 1,8-diazabicyclo-[5.4.0]-7-undecene (0.63 ml) in ethyl acetate (30 ml) was heated for 1.5 hour under reflux. The reaction mixture was washed with a 10% aqueous solution of potassium hydrogensulfate, water and a saturated aqueous saline solution, successively, followed by drying over magnesium sulfate. The solvent was distilled under reduced pressure. Crude crystals thus obtained were recrystallized from ethyl acetate-isopropyl ether to afford the title compound as colorless crystals (0.56 g, 86%), m.p.182°–183° C.

| Elemental Analysis for C$_{25}$H$_{27}$N$_5$O$_4$.0.2H$_2$O: | | | |
|---|---|---|---|
| | C (%) | H (%) | N (%) |
| Calcd.: | 64.67; | 6.02; | 14.62 |
| Found: | 64.59; | 6.04; | 14.66 |

$^1$H-NMR(200MHz,CDCl$_3$) δ: 0.84(3H,t), 1.31(3H,t), 1.44–1.65(2H,m), 3.14–3.28(2H,m), 3.60(3H,s), 4.23(2H,q), 4.47(2H,s), 7.17–7.68(7H,m), 7.73(1H,s), 7.86(1H,dd), 8.64 (1H,bd). IR(nujol)cm$^{-1}$: 1775, 1710, 1565, 1520, 1490, 1325, 1245, 1175, 1130, 1100, 935, 875, 765.

Working Example 24

3-[N-[2'-(2,5-dihydro-5-oxo-1,2,4-oxadiazol-3-yl)biphenyl-4-yl]methyl-N-propylamino]-1-methylpyrazole-4-carboxylic acid Starting from the compound (0.23 g) obtained in Working Example 23 e), substantially the same procedure as in Working Example 2 was followed to afford the title compound as colorless crystals (0.16 g, 76%), m.p.124°–126° C.

| Elemental Analysis for C$_{23}$H$_{23}$N$_5$O$_4$.0.2AcEt.0.2hexane: | | | |
|---|---|---|---|
| | C (%) | H (%) | N (%) |
| Calcd.: | 64.12; | 5.85; | 14.95 |
| Found: | 64.06; | 6.09; | 14.86 |

$^1$H-NMR(200MHz,CDCl$_3$) δ: 0.93(3H,t), 1.48–1.70(2H,m), 3.13–3.27(2H,m), 3.86(3H,s), 4.19(2H,s), 7.12–7.31(4H,m), 7.40–7.53(2H,m), 7.56–7.68(1H,m), 7.77(1H,d), 7.93(1H,s), 8.96(1H,bd). IR(nujol)cm$^{-1}$: 1770, 1670, 1565, 1510, 1410, 1310, 1240, 1175, 1135, 1105, 940.

Working Example 25

Ethyl 3-[N-[2,-(2,5-dihydro-5-oxo-1,2,4-thiadiazol-3-yl)biphenyl-4-yl]methyl-N-propylamino]1-methylpyrazole-4-carboxylate Starting from the compound (0.44 g) obtained in Working Example 23 c), substantially the same procedure as in Working Example 3 c) was followed to afford the title compound as colorless crystals (0.18 g, 38%), m.p.147°–149° C. (recrystallized from ethyl acetate-isopropyl ether).

| Elemental Analysis for C$_{25}$H$_{27}$N$_5$O$_3$S: | | | |
|---|---|---|---|
| | C (%) | H (%) | N (%) |
| Calcd.: | 62.87; | 5.70; | 14.66 |
| Found: | 62.49; | 5.77; | 14.30 |

$^1$H-NMR(200MHz,CDCl$_3$) δ: 0.83(3H,t), 1.30(3H,t), 1.46–1.64(2H,m), 3.23(2H,t-like), 3.71(3H,s)4.24(2H,q), 4.56(2H,s), 7.23(2H,d), 7.34–7.62(5H,m) 7.74(1H,s), 7.90(1H,dd), 8.42(1H,bd). IR(nujol)cm$^{-1}$: 1715, 1690, 1565, 1520, 1445 1165 1090.

Working Example 26

3-[N-[2'-(2,5-dihydro-5-oxo-1,2,4-thiadiazol-3-yl)biphenyl-4-yl]methyl-N-propylamino]-1-methylpyrazole-4-carboxylic acid Starting from the compound (0.12 g) obtained in Working Example 25, substantially the same procedure as in Working Example 2 was followed to afford the title compound as colorless crystals (0.10 g, 90%), m.p. 110°–112° C. (recrystallized from ethyl acetate-isopropyl ether).

Elemental Analysis for $C_{23}H_{23}N_5O_3S.0.1iPr_2O$:

|         | C (%) | H (%) | N (%) |
|---------|-------|-------|-------|
| Calcd.: | 61.65; | 5.35; | 15.23 |
| Found:  | 61.47; | 5.42; | 15.14 |

$^1$H-NMR(200MHz,CDCl$_3$) δ: 0.79(3H,t), 1.38–1.63(2H,m), 2.96–3.14(2H,m), 3.81(3H,s), 4.27(2H,s), 7.14–7.63(7H,m), 7.74(1H,s), 7.80(1H,d), 9.40(1H,bd). IR(nujol)cm$^{-1}$: 1695, 1560, 1550, 1505, 1160, 760.

Working Example 27

Ethyl 3-[N-butyryl-N-[2'-(2,5-dihydro-5-oxo-1,2,4-thiadiazol-3-yl)biphenyl-4-yl]methylamino]-1-methylpyrazole-4-carboxylate a) Ethyl 3-[N-butyryl-N-(2'-cyanobiphenyl-4-yl)methyl amino]-1-methylpyrazole-4-carboxylate To a solution of the compound (1.80 g) obtained in Working Example 23 a), triethylamine (1.4 ml) and 4-dimethylaminopyridine (0.31 g) in 1,2-dichloroethane (50 ml) was added dropwise at 0° C. butyryl chloride (1.04 ml). The reaction mixture was stirred overnight and the solvent was distilled off. To the residue was added ethyl acetate, which was washed with water, a 10% aqueous solution of potassium hydrogensulfate, water and a saturated aqueous saline solution successively, followed by drying over magnesium sulfate. The solvent was distilled off to give crude crystals, followed by recrystallization from ethyl acetate-isopropyl ether to afford the title compound as colorless crystals (1.85 g, 86%), m.p.118°–119° C.

Elemental Analysis for $C_{25}H_{26}N_4O_3$:

|         | C (%) | H (%) | N (%) |
|---------|-------|-------|-------|
| Calcd.: | 69.75; | 6.09; | 13.01 |
| Found:  | 69.77; | 6.09; | 12.86 |

$^1$H-NMR(200MHz,CDCl$_3$) δ: 0.86(3H,t), 1.28(3H,t), 1.45–1.78(2H,m), 2.14(2H,t), 3.87(3H,s), 4.20(2H,q), 4.93(2H,s), 7.31–7.68(7H,m), 7.73(1H,d), 7.87(1H,s). IR (nujol)cm$^{-1}$: 2225, 1705, 1660, 1545, 1500, 1285, 1245, 1165, 1135, 1110, 1045, 770.

b) Ethyl 3-[N-butyryl-N-(2'-hydroxycarbamimidoylbiphenyl-4-yl)methylamino]-1-methylpyrazol-4-carboxylate Starting from the compound (1.07 g) obtained in Working Example 27 a), substantially the same procedure as in Working Example 3) was followed to afford the title compound as a powder (0.50 g, 43%). $^1$H-NMR(200MHz, CDCl$_3$) δ: 0.86(3H,t), 1.26(3H,t), 1.54–1.75(2H,m), 2.18(2H,t), 3.88(3H,s), 4.15(2H,q), 4.29(2H,bds), 4.90(2H,s), 7.20–7.50(7H,m), 7.55(1H,d), 7.86(1H,s). IR(neat)cm$^{-1}$: 3460, 3370 2970 1715 1705, 1650, 1635, 545, 1495, 1370, 1240, 1170, 1130, 1040.

c) Ethyl 3-[N-butyryl-N-[2'-(2,5-dihydro-5-oxo-1,2,4-oxadiazol-3-yl)biphenyl-4-yl]methylamine]-1-methylpyrazol-4-carboxylate Starting from the compound (0.49 g) obtained in Working Example 27 b), substantially the same procedure as in Working Example 5 d) was followed to afford the title compound as a powder (0.45 g, 88%).

Elemental Analysis for $C_{26}H_{27}N_5O_5.0.2H_2O$:

|         | C (%) | H (%) | N (%) |
|---------|-------|-------|-------|
| Calcd.: | 63.33; | 5.60; | 14.20 |
| Found:  | 63.27; | 5.33; | 14.29 |

$^1$H-NMR(200MHz,CDCl$_3$) δ: 0.8 9(3H,t), 1.31(3H,t), 1.56–3.90(3H,s), 4.12(2H,q), 1.87(2H,m), 2.16(2H,t-like), 7.43–7.70(3H,m), 4.92(2H,bd), 7.13–7.33(4H,m), 7.83(1H,d), 8.12(1H,s), 9.18(1H,bd). IR(nujol)cm$^{-1}$: 1780, 1715, 1665, 1640, 1545, 1495, 1400, 1305, 1220, 1170, 1130, 1105, 1040, 940, 760.

Working Example 28

3-[N-butyryl-N-[2'-(2,5-dihydro-5-ox-1,2,4-oxadiazol-3-yl)biphenyl-4-yl]methylamino]-1-methylpyrazole-4-carboxylic acid Starting from the compound (0.35 g) obtained in Working Example 27 c), substantially the same procedure as in Working Example 2 was followed to afford the title compound as colorless crystals (0.27 g, 83%), m.p.220°–222° C. (recrystallized from ethyl acetate-isopropyl ether).

Elemental Analysis for $C_{24}H_{23}N_5O_5$:

|         | C (%) | H (%) | N (%) |
|---------|-------|-------|-------|
| Calcd.: | 62.47; | 5.02; | 15.18 |
| Found:  | 62.21; | 5.14; | 15.20 |

$^1$H-NMR(200MHz,CDCl$_3$) δ: 0.85(3H,t), 1.50–1.73(2H,m), 2.08(2H,t), 3.97(3H,s), 4.90(2H,bd), 7.20(2H,d), 7.31–7.67(5H,m), 7.88(1H,s), 8.02(1H,d). IR(nujol)cm$^{-1}$: 3190, 1790, 1700, 1660, 1545, 1500, 1400, 1255, 1215, 1165, 1140, 935, 760.

Working Example 29

Ethyl 3-[N-butyryl-N-[2'-(2,5-dihydro-5-oxo-1,2,4-thiadiazol-3-yl)biphenyl-4-yl]methylamino]-1-methylpyrazole-4-carboxylate Starting from the compound (0.25 g) obtained in Working Example 27 b), substantially the same procedure as in Working Example 3 c) was followed to afford the title compound as a powder (0.14 g, 52%). $^1$H-NMR(200MHz, CDCl$_3$) δ: 0.87(3H,t), 1.30(3H,t), 1.52–1.74(2H,m), 2.15(2H,t), 3.88(3H,s), 4.21(2H,q), 4.92(2H,s), 7.16–7.63(7H,m), 7.83–7.92(1H,m), 7.94(1H,s), 8.70(1H,bd). IR(neat)cm$^{-1}$: 3130, 3060, 2960, 1700, 1545, 1495, 1440, 1395, 130–5, 1260, 1215, 1170, 1125, 1100.

Working Example 30

3-[N-butyryl-N-[2'-(2,5-dihydro-5-oxo-1,2,4-thiadiazol-3-yl]biphenyl-4-yl]methylamino]-1-methylpyrazole-4-carboxylic acid Starting from the compound (0.14 g) obtained in Working Example 29, substantially the same procedure as in Working Example 2 was followed to afford the title compound as colorless crystals (79 mg, 61%), m.p. 217°–219° C. (recrystallized from ethyl acetate-isopropyl ether).

| Elemental Analysis for $C_{24}H_{23}N_5O_4S$: | | | |
|---|---|---|---|
| | C (%) | H (%) | N (%) |
| Calcd.: | 60.36; | 4.85; | 14.67 |
| Found: | 60.12; | 4.84; | 14.36 |

$^1$H-NMR(200MHz,CDCl$_3$) δ: 0.87(3H,t), 1.54–1.76(2H,t), 3.98(3H,s), 4.89(2H,bd), 7.09–7.24 (4H,m), 7.32–7.40(1H, m), 7.44–7.62(2H,m), 7.79(1H,s), 7.95(1H,dd), 9.48 (1H, bd). IR(nujol)cm$^{-1}$: 3200, 1720, 1695, 1660, 1540, 1505, 1395, 1250, 1210, 1160, 1135, 760.

Working Example 31

Ethyl 5-[N-[2'-(2,5-dihydro-5-oxo-1,2,4-oxadiazol-3-yl)biphenyl-4 -yl]methyl-N-propylamino]-1-methylpyrazole-4-carboxylate a) Ethyl 5- (2'-cyanobiphenyl-4-yl)methylamino-1-methylpyrazole-4 -carboxylate To a solution of ethyl 5-amino-1-methylpyrazole-4-carboxylate (1.6 9 g) (P. Schmidt et al. Helv. Chim. Acta., 1959, 42, 349) in tetrahydrofuran (30 ml) was added at 0° C. sodium hydride (about 60% in oil, 0.48 g). The mixture was stirred for one hour at room temperature. To the reaction mixture was added portionwise at 0° C. 4-bromomethyl-2'-cyanobiphenyl (3.27 g). The mixture was stirred overnight at room temperature. The reaction mixture was poured into a saturated aqueous solution of ammonium chloride, which was extracted with ethyl acetate. The extract was washed with water and a saturated aqueous saline solution, followed by drying over magnesium sulfate. The solvent was distilled under reduced pressure to give crude crystals. Recrystallization from ethyl acetate-isopropyl ether afforded the title compound as colorless crystals (2.47 g, 69%), m.p.107°–108° C.

| Elemental Analysis for $C_{21}H_{20}N_4O_2$: | | | |
|---|---|---|---|
| | C (%) | H (%) | N (%) |
| Calcd.: | 69.98; | 5.59; | 15.55 |
| Found: | 70.02; | 5.62; | 15.65 |

$^1$H-NMR (200MHz, CDCl$_3$) δ: 1.33(3H,t), 3.78(3H,s), 4.27(2H,q), 4.53(2H,bds), 6.18(1H,bd), 7.40–7.72(8H,m), 7.74–7.83(1H,m). IR(nujol)cm$^{-1}$: 3330, 3050, 2225, 1675, 1585, 1540, 1480, 1220, 1170, 1080, 1040, 770, 760.

b) Ethyl 5-[N-(2'-cyanobiphenyl-4-yl)methyl-N-propylamino]-1-methylpyrazole-4-carboxylate To a solution of the compound (0.51 g) obtained in Working Example 31 a) in N,N-dimethylformamide (3 ml) was added, at 0° C., sodium hydride (about 60% in oil, 68 mg). The mixture was stirred for 30 minutes at room temperature. To the reaction mixture was added at 0° C. propyl iodide (0.17 ml), and the mixture was stirred for one hour at room temperature. To the reaction mixture was added a saturated aqueous solution of ammonium chloride, followed by extraction with ethyl acetate. The extract was washed with water and a saturated aqueous saline solution, followed by drying over magnesium sulfate. The solvent was distilled off under reduced pressure and the residue was purified by column chromatography on silica gel to afford the title compound as an oil (0.39 g, 69%). $^1$H-NMR(200MHz,CDCl$_3$) δ: 0.86(3H,t), 1.30–1.52(2H,m), 1.40(3H,t), 3.04–3.18(2H,m), 3.60(3H,s), 4.32(2H,s), 4.33(2H,q), 7.29–7.53(6H,m), 7.57–7.68(1H,m), 7.71–7.78(1H,m), 7.85(1H,s). IR(neat)cm$^{-1}$: 2960, 2870, 2220, 1705, 1480, 1375, 1225, 1195, 1045.

c) Ethyl 5-[N-(2'-hydroxycarbamimidoylbiphenyl- 4-yl)methyl-N-propylamino]-1-methylpyrazole-4-carboxylate Starting from the compound (1.30 g) obtained in Working Example 31 b), substantially the same procedure as in Working Example 3 b) was followed to afford the title compound as an oil (0.28 g, 20%). $^1$H-NMR(200MHz, CDCl$_3$) δ: 0.90(3H,t), 1.32–1.54(2H,m), 1.39(3H,t), 3.17(2H,t), 3.47(3H,s), 4.28(2H,s), 4.33(2H,q), 4.51(2H, bds), 7.17(2H,d), 7.23–7.60(6H,m), 7.81(1H,s). IR(neat)cm$^{-1}$: 3480, 3360, 2970, 1735, 1705, 1645, 1545, 1490, 1375, 1240, 1195, 1150.

d) Ethyl 5-[N-[2'-(2,5-dihydro-5-oxo-1,2,4-oxadiazol-3-yl)biphenyl-4-yl]methyl-N-propylamino]-1-methylpyrazole-4-carboxylate Starting from the compound (0.28 g) obtained in Working Example 31 c), substantially the same procedure as in Working Example 5 d) was followed to afford the title compound as colorless crystals (0.22 g, 76%), m.p.174°–175° C. (recrystallized from ethyl acetate-isopropyl ether).

| Elemental Analysis for $C_{25}H_{27}N_5O_4$: | | | |
|---|---|---|---|
| | C (%) | H (%) | N (%) |
| Calcd.: | 65.06; | 5.90; | 15.17 |
| Found: | 65.03; | 5.97; | 14.96 |

$^1$H-NMR(200MHz,CDCl$_3$) δ: 0.87(3H,t), 1.27–1.50(2H,m), 1.35(3H,t), 3.09(2H,t), 3.55(3H,s), 4.25(2H,q), 4.26(2H,s), 7.23(4H,s-like), 7.36–7.66(3H,m), 7.74(1H,s), 7.80(1H,dd), 8.85(1H,bd). IR(nujol)cm$^{-1}$: 1755, 1700, 1600, 1545, 1485, 1430, 1250, 1195, 1050, 950, 765.

Working Example 32

5-[N-[2'-(2,5-dihydro-5-oxo-1,2,4-oxadiazol-3-yl)biphenyl-4-yl]methyl-N-propylamino]-1-methylpyrazole-4-carboxylic acid Starting from the compound (0.14 g) obtained in Working Example 31 d), substantially the same procedure as in Working Example 2 was followed to afford the title compound as colorless crystals (0.11 t, 83%), m.p.197°–198° C. (recrystallized from ethyl acetate-isopropyl ether).

Elemental Analysis for $C_{23}H_{23}N_5O_4 \cdot 0.2H_2O$:

|  | C (%) | H (%) | N (%) |
|---|---|---|---|
| Calcd.: | 63.21; | 5.40; | 16.02 |
| Found: | 63.36; | 5.37; | 15.75 |

$^1$H-NMR(200MHz,CDCl$_3$) δ: 0.89(3H,t), 1.32–1.53(2H,m), 3.12(2H,t), 3.76(3H,s), 4.14(2H,s), 7.13(2H,d), 7.20–7.37(3H,m), 7.44–7.65(2H,m), 7.81(1H,s), 8.06(1H, dd), 9.06(1H,bd). IR (nujol) cm$^{-1}$: 3170, 1750, 1715, 1545, 1490, 1230, 1190.

Working Example 33

Ethyl 2-[N-[2'-(2,5-dihydro-5-oxo-1,2,4-oxadiazol-3-yl)biphenyl-4-yl]methyl-N-propylamino]quinoline-3-carboxylate a) Ethyl 2-propylaminoquinoline-3-carboxylate An solution of ethyl 2-chloroquinoline-3-carboxylate (1.1 g) [(K. Shimizu et al., J. Pharm. Soc. Jpn., 87, 672(1967)] and propylamine (1.8 g) in ethanol (20 ml) was heated at 95° C. for 8 hours in a sealed tube. The reaction mixture was concentrated under reduced pressure, to which was added a saturated aqueous solution of sodium hydrogencarbonate, followed by extraction with chloroform.

The extract was dried over anhydrous sodium sulfate, then the solvent was distilled off. The residue was purified by column chromatography on silica gel to afford the title compound as a yellow oil (0.98 g, 80%). $^1$H-NMR(200MHz, CDCl$_3$) δ: 1.05(3H,t), 1.44(3H,t), 1.64–1.83(2H,m), 3.53–3.65(2H,m), 4.39(2H,q), 7.12–7.20(1H,m), 7.53–7.67(3H,m), 7.97(1H,brs), 8.63(1H,s). IR(neat)cm$^{-1}$: 3375, 2955, 1690, 1620, 1285, 1200.

b) Ethyl 2-[N-(2'-cyanobiphenyl-4-yl)methyl-N-propylamino]quinoline-3-carboxylate Starting from the compound (1.2 g) obtained in Working Example 33 a), substantially the same procedure as in Working Example 23 b) was followed to afford the title compound as a yellow oil (1.3 g, 64%). $^1$H-NMR(200(MHz,CDCl$_3$) δ: 0.83(3H,t), 1.41(3H,t), 1.55–1.74(2H,m), 3.35(2H,t), 4.38(2H,q), 4.92(2H,s), 7.23–7.78(12H,m), 8.33(1H,s). IR(neat)cm$^{-1}$: 2960, 2220, 1720, 1620, 1590, 1490, 1475, 1430, 1225, 1200, 1070, 755.

c) Ethyl 2-[N-(2'-hydroxycarbamimidoylbiphenyl-4-yl)methyl-N-propylamino]quinoline-3-carboxylate Starting from the compound (1.3 g) obtained in Working Example 33 b), substantially the same procedure as in Working Example 3 b) was followed to afford the title compound as a yellow powder (0.77g, 53%), m.p.61°–67° C. $^1$H-NMR(200MHz,CDCl$_3$) δ: 0.82(3H,t), 1.40(3H,t), 1.53–1.73(2H,m), 3.34(2H,t), 4.33–4.43(4H,m), 4.88(2H,s), 7.23–7.74(12H,m), 8.23(1H,s). IR(neat)cm$^{-1}$: 3400, 3370, 1710, 1620, 1595, 1490, 1430, 1205.

d) Ethyl 2-[N-[2'-(2,5-dihydro-5-oxo-1,2,4-oxadiazol-3-yl)biphenyl]methyl-N-propylamino]quinoline-3-carboxylate Starting from the compound (0.35 g) obtained in Working Example 33 c), substantially the same procedure as in Working Example 5 d) was followed to afford the title compound as pale yellow prisms (0.27 g, 72%), m.p.155°–156° C. (isopropanol).

Elemental Analysis for $C_{30}H_{26}N_4O_4$:

|  | C (%) | H (%) | N (%) |
|---|---|---|---|
| Calcd.: | 70.85; | 5.55; | 11.02 |
| Found: | 70.55; | 5.51; | 10.97 |

$^1$H-NMR(200MHz,CDCl$_3$) δ: 0.83(3H,t), 1.41(3H,t), 1.55–1.74(2H,m), 3.34(2H,t), 4.38(2H,q), 4.90(2H,s), 7.23–7.87(12H,m), 8.34(1H,s). IR(nujol)cm$^{-1}$: 3130, 1780, 1670, 1490, 750.

Working Example 34

2-[N-[2'-(2,5-dihydro-5-oxo-1,2,4-oxadiazol-3-yl)biphenyl-4-]methyl-N-propylamino]quinoline-3-carboxylic acid Starting from the compound (0.20 g) obtained in Working Example 33 d), substantially the same procedure as in Working Example 2 was followed to afford the title compound as a yellow powder (0.14 g, 75%).

Elemental Analysis for $C_{28}H_{24}N_4O_4 \cdot 0.5H_2O$:

|  | C (%) | H (%) | N (%) |
|---|---|---|---|
| Calcd.: | 68.70; | 5.15; | 11.45 |
| Found: | 68.90; | 5.01; | 11.35 |

$^1$H-NMR(200MHz,CDCl$_3$) δ: 0.93 (3H,t), 1.45–1.63(2H, m), 3.53(2H,t), 4.40(2H,s), 7.05(2H,d), 7.20(2H,d), 7.38–7.92(6H,m), 7.88(1H,d), 8.08(2H,t), 9.12(1H,s). IR(nujol)cm$^{-1}$: 1780, 1620, 1590, 760.

Working Example 35

Ethyl 2-[N-[2'-(2,5-dihydro-5-oxo-1,2,4-thiadiazol-3-yl)biphenyl-4-yl]methyl-N-propylamino]quinoline-3-carboxylate To a solution of the compound (0.42 g) obtained in Working Example 33 c) in dichloromethane (5 ml) was added dropwise under ice-cooling a solution of 1,1'-thiocarbonyldiimidazole (0.18 g) in dichloromethane (3 ml). The mixture was stirred for 15 minutes, to which were added chloroform (32 ml), silica gel (Merck, Art7734, 4 g) and methanol (8 ml). The mixture was stirred for further 15 hours at room temperature. Silica gel was filtered off, and the filtrate was concentrated under reduced pressure. The residue was purified by column chromatography on silica gel. The product thus obtained was recrystallized from isopropyl ether to afford the title compound as yellow prisms (0.19 g, 42%), m.p.124°–125° C.

Elemental Analysis for $C_{30}H_{28}N_4O_3S$:

|  | C (%) | H (%) | N (%) | S (%) |
|---|---|---|---|---|
| Calcd.: | 68.68; | 5.38; | 10.68; | 6.11 |
| Found: | 68.50; | 5.34; | 10.71; | 6.06 |

$^1$H-NMR(200MHz,CDCl$_3$) δ: 0.82(3H,t), 1.42(3H,t), 1.56–1.72(2H,m), 3.32(2H,t), 4.40(2H,q), 7.24–7.73(11H, m), 8.00(1H,d), 8.15(1H,brs), 8.34(1H,s). IR(nujol)cm$^{-1}$:

1715, 1665, 1500, 1200, 1065, 750.

Working Example 36

2-[N-[2'-(2,5-dihydro-5-oxo-1,2,4-thiadiazol-3-yl)biphenyl-4-yl]methyl-N-propylamino]quinoline-3-carboxylic acid Starting from the compound (0.12 g) obtained in Working Example 35, substantially the same procedure as in Working Example 2 was followed to afford the title compound as a yellow powder (0.11 g, 93%), m.p.118°–124° C.

| Elemental Analysis for $C_{28}H_{24}N_4O_3S \cdot \frac{2}{3}H_2O$: | | | |
|---|---|---|---|
| | C (%) | H (%) | N (%) |
| Calcd.: | 66.13; | 5.02; | 11.02 |
| Found: | 66.29; | 4.80; | 10.91 |

$^1$H-NMR(200MHz,CDCl$_3$) δ: 0.87(3H,t), 1.40–1.58(2H,m), 3.32(2H,t), 4.42(2H,s), 7.19(2H,d), 7.29–7.90(9H,m), 7.99(1H,d), 8.11(1H,d), 8.96(1H,brs), 9.06(1H,s). IR(nujol)cm$^{-1}$: 1695. 1620, 1590, 760.

Experimental Example 1

Inhibitory Effect of Binding of Angiotensin-II to Angiotensin II Receptor

[Method]

An experiment of inhibition on the binding of angiotensin II (A-II) receptor was performed by modified the method of Douglas et al. [Endocrinology, 102, 685–696 (1978)]. An A-II receptor membrane fraction was prepared from bovine adrenal cortex.

The compound of the present invention ($10^{-6}$M or $10^{-7}$M) and $^{125}$I-angiotensin II ($^{125}$I-AII) (2.44KBq/50 microliter) were added to the receptor membrane fraction, and the mixture was incubated at room temperature for one hour. The receptor-bound and free I-AII were separated through a filter (Whatman GF/B filter), and the radioactivity of $^{125}$I-AII bound to the receptor was determined.

[Results]

The results relating to the compounds of the present invention are shown in the table 1.

Experimental Example 2

Inhibitory Effect of the Compound of the Present Invention on AII-induced Pressor Response

[Method]

Jcl:SD rats (9 week old, male) were used. On the previous day of the experiment, rats were applied with cannulation into the femoral artery and vein under anesthesia with pentobarbital Na. These animals were fasted but allowed to access freely to drinking water until the experiment was started. Just on the day of conducting the experiment, the artery cannula was connected with a blood-pressure transducer, and the average blood pressure was recorded by polygraph. Before administration of the drug, the pressor action due to intravenous administration of A-II (100 ng/kg) as the control was determined. The drugs were orally administered, then, at each point of the determination, A-II was administered intravenously, and the pressor action was similarly determined. By comparing the pressor action before and after administration of the drug, the percent inhibition by the drug was evaluated.

[Results]

The results relating to the compounds of the present invention are shown in Table 1.

TABLE 1

| Example | Structural Formula | Radioreceptor assay [% inhibition] | Pressor Response [p.o.] 0.3 mg/kg | 1 mg/kg |
|---|---|---|---|---|
| 2 | (structure shown) | 52 ($10^{-6}$M) 17 ($10^{-7}$M) | +++ | +++ [a] |

TABLE 1-continued

| Example | Structural Formula | Radioreceptor assay [% inhibition] | Pressor Response [p.o.] 0.3 mg/kg | 1 mg/kg |
|---|---|---|---|---|
| 4 | (structure) | 61 ($10^{-6}$M) 20 ($10^{-7}$M) | NT | +++ |
| 6 | (structure) | 55 ($10^{-6}$M) 16 ($10^{-7}$M) | NT | +++ | a)+++ ≧ 70% > ++ ≧ 50% > +
NT: Not tested

Formulation Examples

When the compound (I) of the present invention is used as a therapeutic agent for circulatory disturbances such as hypertension, heart diseases, cerebral apoplexy and nephritis, it can be used in accordance with, for example, the following formulations.

1. Capsules

| | |
|---|---|
| (1) 4-[N-butyl-N-[2'-(2,5-dihydro-5-oxo-1,2,4-oxadiazol-3-yl)biphenyl-4-yl]methyl] aminopyrimidine-5-carboxylic acid | 10 mg |
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

2. Tablet

| | |
|---|---|
| (1) 4-[N-butyl-N-[2'-(2,5-dihydro-5-oxo-1,2,4-oxadiazol-3-yl)biphenyl-4-yl]methyl] aminopyrimidine-5-carboxylic acid | 10 mg |
| (2) lactose | 35 mg |
| (3) corn starch | 150 mg |
| (4) microcrystalline cellulose | 30 mg |
| (5) magnesium stearate | 5 mg |
| one table | 230 mg |

(1), (2), (3), two thirds of (4) and a half of (5) are mixed and then granulated, followed by subjecting the mixture to compression molding.

3. Injections

| | |
|---|---|
| (1) 4-[N-butyl-N-[2'-(2,5-dihydro-5-oxo-1,2,4-oxadiazol-3-yl)biphenyl-4-yl]methyl] aminopyrimidine-5-carboxylic acid disodium salt | 10 mg |
| (2) inositol | 100 mg |
| (3) benzyl alcohol | 20 mg |

3. Injections

|  |  |
|---|---|
| one ampoule | 130 mg |

(1), (2) and (3) are dissolved in water for injection to make the whole volume 2 ml, which is filled into an ampoule. The whole process is conducted under sterile conditions.

4. Capsules

| (1) 4-[N-butyl-N-[2'-(2,5-dihydro-5-oxo-1,2,4-thiadiazol-3-yl)biphenyl-4-yl]methyl]aminopyrimidine-5-carboxylic acid | 10 mg |
|---|---|
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

5. Tablets

| (1) 4-[N-butyl-N-[2'-(2,5-dihydro-5-oxo-1,2,4-thiadiazol-3yl)biphenyl-4-yl]methyl]aminopyrimidine-5-carboxylic acid | 10 mg |
|---|---|
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

6. Injections

| (1) 4-[N-butyl-N-[2'-(2,5-dihydro-5-oxo-1,2,4-thiadiazol-3-yl)biphenyl-4-yl]methyl]aminopyridine-5-carboxylic acid disodium salt | 10 mg |
|---|---|
| (2) inositol | 100 mg |
| (3) benzyl alcohol | 20 mg |
| one ampoule | 130 mg |

(1), (2), (3) are dissolved in water for injection to make the whole volume 2 ml, which is filled into an ampoule. The whole process is conducted under sterile conditions.

7. Capsules

| (1) 2-[N-[2,5-dihydro-5-oxo-1,2,4-oxadiazol-3-yl)biphenyl-4-yl]methyl-N-propyl]aminopyridine-3-carboxylic acid | 10 mg |
|---|---|
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

8. Tablets

| (1) 2-[N-[2'-(2,5-dihydro-5-oxo-1,2,4-oxadiazol-3-yl)biphenyl-4-yl]methyl-N-propyl]aminopyridine-3-carboxylic acid | 10 mg |
|---|---|
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

9. Injections

| (1) 2-[N-[2'-(2,5-dihydro-5-oxo-1,2,4-oxadiazol-3-yl)biphenyl-4-yl]methyl-N-propyl]aminopyridine-3-carboxylic acid disodium salt | 10 mg |
|---|---|
| (2) inositol | 100 mg |
| (3) benzyl alcohol | 20 mg |
| one ampoule | 130 mg |

(1), (2) and (3) are dissolved in water for injection to make the whole volume 2 ml, which is filled into an ampoule. The whole process is conducted under sterile conditions.

10. capsules

| (1) 2-[N-[2'-(2,5-dihydro-5-oxo-1,2,4-thiadiazol-3-yl)biphenyl-4-yl]methyl-N-propyl]aminopyridine-3-carboxylic acid | 10 mg |
|---|---|
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled in a gelatin capsule.

11. Tablets

| (1) 2-[N-[2'-(2,5-dihydro-5-oxo-1,2,4-thiadiazol-3-yl)biphenyl-4-yl]methyl-N-propyl]aminopyridine-3-carboxylic acid | 10 mg |
|---|---|
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

12. Injections

| (1) 2-[N-[2'-(2,5-dihydro-5-oxo-1,2,4-thiadiazol-3-yl)biphenyl-4-yl]methyl-N-propyl]aminopyridine-3-carboxylic acid disodium salt | 10 mg |
|---|---|
| (2) inositol | 100 mg |

| 12. Injections | |
|---|---|
| (3) benzyl alcohol | 20 mg |
| one ampoule | 130 mg |

(1), (2) and (3) are dissolved in water for injection to make the whole volume 2 ml, which is filled into an ampoule. The whole process is conducted under sterile conditions.

What is claimed is:

1. Compounds represented by the formula

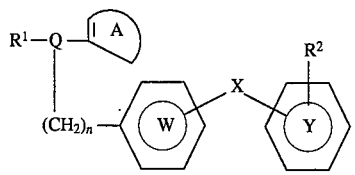

wherein $R^1$ is a $C_{1-8}$ alkyl, $C_{2-8}$ alkenyl, $C_{2-8}$ alkynyl, $C_{3-6}$ cycloalkyl or $C_{3-6}$ cycloakenyl which may be substituted with hydroxy, amino, N—$C_{1-4}$ alkylamino, N,N—di—$C_{1-4}$ alkylamino, halogen, $C_{1-4}$ alkoxy or $C_{1-4}$ alkylthio, aryl or aralkyl group which may be substituted with halogen, nitro, an optionally substituted amino, $C_{1-4}$ alkoxy, $C_{1-4}$ alkythio or $C_{1-4}$ alkyl and which may be bound through a group of the formula: —N(R)$^9$— wherein $R^9$ is hydrogen or an optionally substituted $C_{1-4}$ alkyl group, —O— or —S(O)$_m$— wherein m is an integer of 0 to 2, or a $C_{1-8}$ alkanoyl, $C_{3-8}$ alkenoyl, $C_{3-8}$ alkynoyl, or $C_{4-7}$ cycloalkylcarbonyl group which may be substituted with hydroxyl, amino, N—$C_{1-4}$ alkylamino, N,N—di—$C_{1-4}$ alkylamino, halogen, $C_{1-4}$ alkoxy or $C_{1-4}$ alkylthio group; $R^2$ is a 5–7 membered heterocyclic residue having, as a group capable of constituting the ring, a carbonyl group, thiocarbonyl group, or an optionally oxidized sulfur atom which may be substituted with a group of the formula:

1) —CH($R^4$)—OCOR$^5$, wherein $R^4$ is hydrogen, $C_{1-6}$ alkyl, $C_{2-6}$ alkenyl or $C_{3-8}$ cycloalkyl, and $R^5$ is $C_{1-6}$ alkyl, $C_{2-6}$ alkenyl, $C_{3-8}$ cycloalkyl, $C_{1-3}$ alkyl substituted with $C_{3-8}$ cycloalkyl, $C_{2-3}$ alkenyl substituted with $C_{3-8}$ cycloalkyl, optionally substituted aryl $C_{1-6}$ alkoxy, $C_{2-8}$ alkenyloxy, $C_{3-8}$ cycloalkoxy, $C_{1-3}$ alkoxy substituted with $C_{3-8}$ cycloalkyl, $C_{2-3}$ alkenyloxy substituted with $C_{3-8}$ cycloalkyl or optionally substituted aryloxy,
2) an optionally substituted alkyl,
3) acyl,
4) halogen,
5) nitro,
6) cyano,
7) $C_{1-4}$ alkoxy or 8) optionally substituted amino; Q is CH or N; X is a direct bond or a divalent atomic chain having a straight chain of an atomic length of two or less between the ring Y and the ring W, and may have a side chain; rings W and Y are each an aromatic hydrocarbon residue or 4–7 membered hetero-cyclic residue containing one or more of N, S or O, which may be substituted with halogen, nitro, cyano, $C_{1-4}$ alkoxy or an optionally substituted amino group; n is an integer of 1 or 2; the ring A is a 5–8 membered cyclic hydrocarbon residue or heterocyclic ring having at least one unsaturated bond selected from the group consisting of

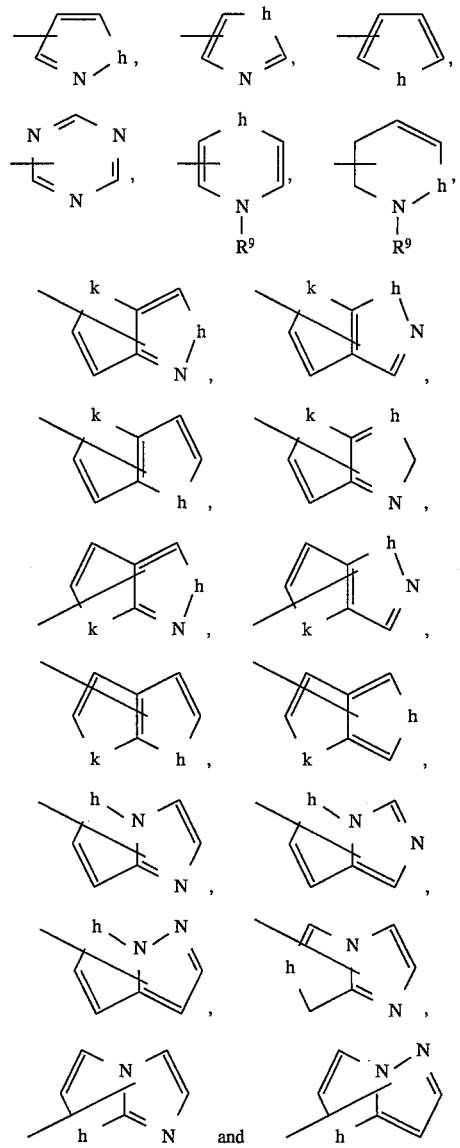

wherein h and k independently stand for

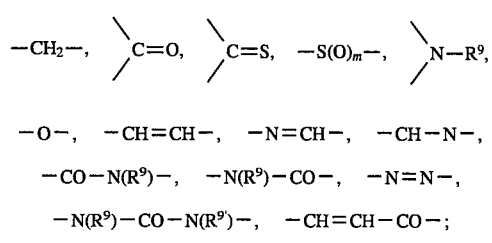

wherein $R^9$ and are $R^{9'}$ independently H or an optionally substituted $C_{1-4}$ alkyl group and m is an integer of 1 to 2, which may be substituted with 1) an optionally esterified or amidated carboxyl, tetrazolyl, trifluoro-methanesulfonic acid amide, phosphoric acid or sulfonic acid, wherein said groups may be protected with an optionally substituted lower alkyl group or acyl group,
2) halogen,
3) nitro,
4) cyano,
5) optionally substituted amino, 6) a group represented by the formula: —U—$R^6$, wherein U stands for a bond, —O—, —S— or —CO— and $R^6$ stands for hydrogen, an optionally substituted lower alkyl group, a group represented by the formula: —$(CH_2)_l$—CO—D', wherein D' stands for hydrogen, hydroxyl group, amino, N—$C_{1-4}$ alkylamino, N-N-di-$C_{1-4}$ alkylamino, $C_{1-6}$ alkoxy group whose alkyl moiety is optionally substituted with hydroxyl, optionally substituted amino, halogen, $C_{1-6}$ alkoxy, $C_{1-6}$ alkylthio, optionally substituted dioxolenyl, or a group represented by the formula —O—$CH(R^7)OCOR^8$, wherein $R^7$ stands for hydrogen, $C_{1-6}$ alkyl group or $C_{5-7}$ cycloalkyl group, and $R^8$ stands for $C_{1-6}$ alkyl group, $C_{2-8}$ alkenyl group, $C_{5-7}$ cycloalkyl group, $C_{1-3}$ alkyl group substituted with $C_{5-7}$ cycloalkyl group or aryl group, $C_{2-3}$ alkenyl group substituted with $C_{5-7}$ cycloalkyl or aryl group, optionally substituted aryl group, $C_{1-6}$ alkoxy group, $C_{2-8}$ alkenyloxy group, $C_{5-7}$ cycloalkoxy group, $C_{1-3}$ alkoxy group substituted with $C_{5-7}$ cycloalkyl or aryl group, $C_{2-3}$ alkenyloxy group substituted with $C_{5-7}$ cycloalkyl or aryl group or aryloxy group, and l denotes 0 or 2, and two of the substituents are optionally bonded to each other to form a ring; or a salt thereof.

2. The compound or a salt thereof as claimed in claim 1, wherein the atom adjacent to the position where the ring A is bound to Q is a carbon atom substituted with an optionally esterified or amidated carboxyl, tetrazolyl, trifluoromethanesulfonic amide, phosphoric acid or sulfonic acid group, which may be protected with an optionally substituted lower alkyl or acyl group, or a salt thereof.

3. The compound or a salt thereof as claimed in claim 1, wherein $R^1$ is alkyl, alkenyl, alkynyl, cycloalkyl or cycloakenyl which may be bound through a group of the formula: —$N(R^9)$— wherein $R^9$ is hydrogen or optionally substituted $C_{1-4}$ alkyl, —O— or —$S(O)_m$— wherein m is an integer of 0 to 2 and which may be substituted with hydroxy, optionally substituted amino, halogen, $C_{1-4}$ alkoxy or $C_{1-4}$ alkylthio.

4. The compound or a salt thereof as claimed in claim 1, wherein $R^1$ is aryl or aralkyl which may be bound through a group of the formula: —$N(R^9)$— wherein $R^9$ is hydrogen or optionally substituted $C_{1-4}$ alkyl, —O— or —$S(O)_m$— wherein m is an integer of 0 to 2 and which may be substituted with halogen, nitro, optionally substituted amino, $C_{1-4}$ alkoxy, $C_{1-4}$ alkylthio or $C_{1-4}$ alkyl.

5. The compound or a salt thereof as claimed in claim 1, wherein $R^1$ is $C_{1-8}$ alkyl or $C_{2-8}$ alkenyl which may be bound through a group of the formula: —$N(R^9)$— wherein $R^9$ is hydrogen or optionally substituted $C_{1-4}$ alkyl, —O— or —$S(O)_m$— wherein m is an integer of 0 to 2 and which may be substituted with hydroxy, amino, N—$C_{1-4}$ alkylamino, N,N-di-$C_{1-4}$ alkylamino, halogen, $C_{1-4}$ alkoxy or $C_{1-4}$ alkylthio.

6. The compound or a salt thereof as claimed in claim 1, Wherein $R^1$ is $C_{1-5}$ alkyl or $C_{2-5}$ alkenyl which may be substituted with hydroxy, amino, halogen or $C_{1-4}$ alkoxy.

7. The compound or a salt thereof as claimed in claim 1, wherein $R^1$ is alkanoyl, alkenoyl, alkynoyl, cycloalkylcarbonyl, aralkynoyl or benzoyl.

8. The compound or a salt thereof as claimed in claim 1, wherein $R^1$ is alkanoyl, alkenoyl, alkynoyl or cycloakylcarbonyl which may be substituted with a group of hydroxyl optionally substituted amino, halogen, $C_{1-4}$ alkoxy or $C_{1-4}$ alkylthio.

9. The compound or a salt thereof as claimed in claim 1, wherein $R^1$ is $C_{1-8}$ alkanoyl, $C_{3-8}$ alkenoyl, $C_{3-8}$ alkynoyl, or $C_{4-7}$ cycloalkylcarbonyl which may be substituted with a group of hydroxyl, amino, N—$C_{1-4}$ alkylamino, N,N-di-$C_{1-4}$ alkylamino, halogen, $C_{1-4}$ alkoxy or $C_{1-4}$ alkylthio.

10. The compound or a salt thereof as claimed in claim 1, wherein $R^2$ is an optionally substituted 5-7 membered N-containing heterocyclic residue having, as a group capable of constituting the ring, a carbonyl group, a thiocarbonyl group, an optionally oxidized sulfur atom or a group convertible thereinto, and having hydrogen atom capable of being protonated.

11. The compound or a salt thereof as claimed in claim 1, wherein $R^2$ is a group selected from the class consisting of

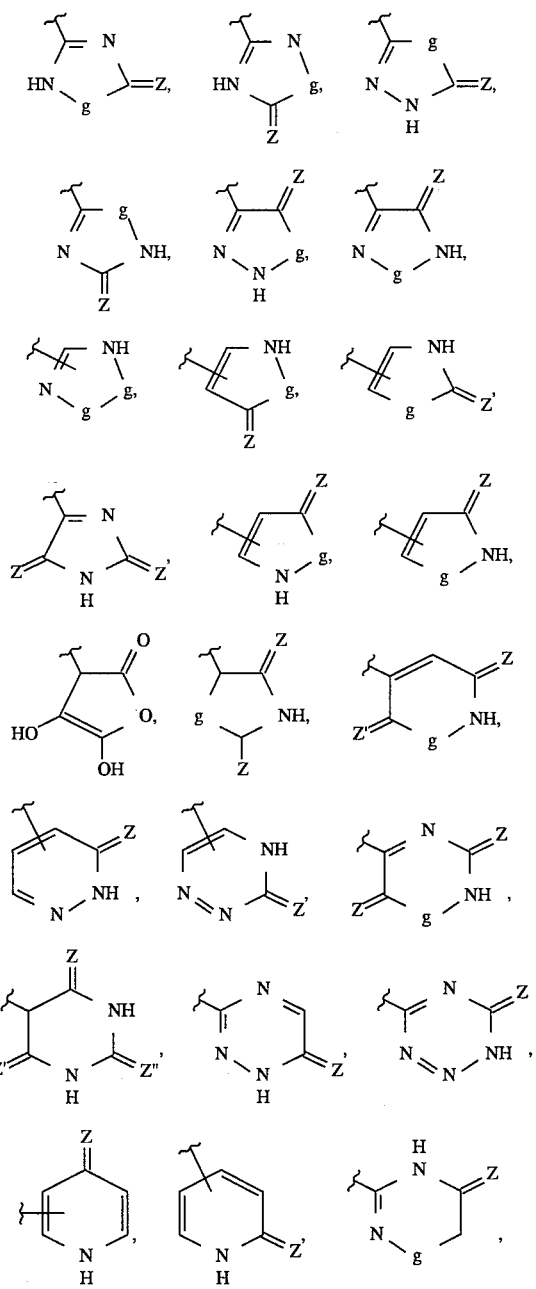

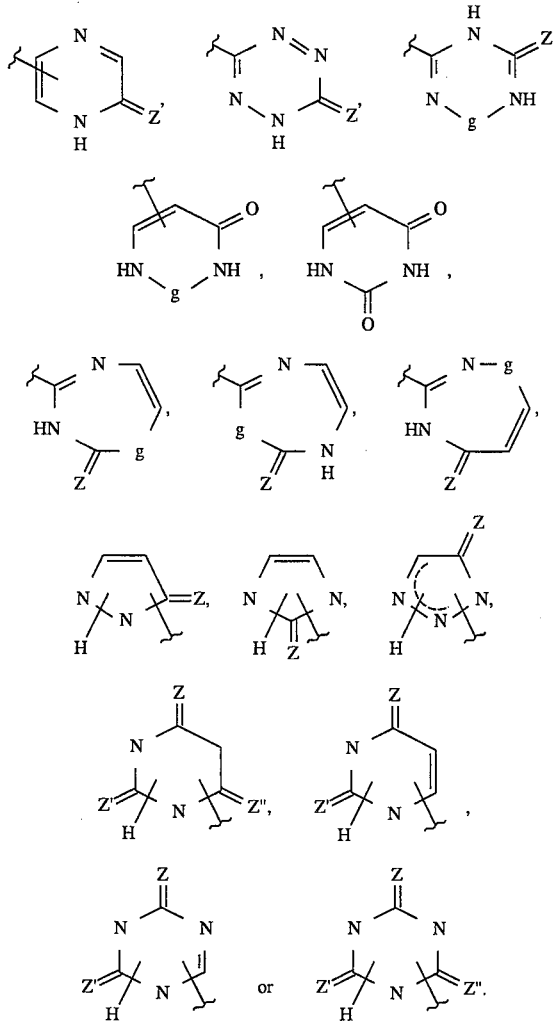

wherein g is —CH₂—, —NR⁹— wherein R⁹ is hydrogen or optionally substituted $C_{1-4}$ alkyl, —O— or —S(O)$_m$— wherein m is an integer of 0 to 2, and >=Z, >=Z' and >=Z" are independently a carbonyl group, a thiocarbonyl group, an optionally oxidized sulfur atom or a group convertible thereinto.

12. The compound or a salt thereof as claimed in claim 1, wherein R² is a group of the formula:

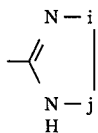

wherein i is —O— or —S— and j is a carbonyl group, a thiocarbonyl group, an optionally oxidized sulfur atom or a group convertible thereinto.

13. The compound or a salt thereof as claimed in claim 1, wherein rings W and Y are independently phenyl, pyridyl, pyrimidinyl, pyridazinyl, pyrazinyl, thienyl, furyl, pyrrolyl, imidazolyl, pyrazolyl, isothiazolyl, isoxazolyl, benzofuranyl, isobenzofuranyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl or pterdinyl, which may be substituted with halogen, nitro, cyano, $C_{1-4}$ alkoxy or optionally substituted amino.

14. The compound or a salt thereof as claimed in claim 1, wherein W is phenylene group.

15. The compound or a salt thereof as claimed in claim 1, wherein Y is phenyl group.

16. The compound or a salt thereof as claimed in claim 1, wherein X is a direct bond, $C_{1-4}$ alkylene, —CO—, —O—, —S—, —NH—, —CO—NH—, —O—CH₂—, —S—CH₂— or —CH=CH—.

17. The compound or a salt thereof as claimed in claim 1, wherein X is a direct bond.

18. The compound or a salt thereof as claimed in claim 1, wherein n is an integer of 1.

19. The compound or a salt thereof as claimed in claim 1, wherein, ring A is a group of the class consisting of

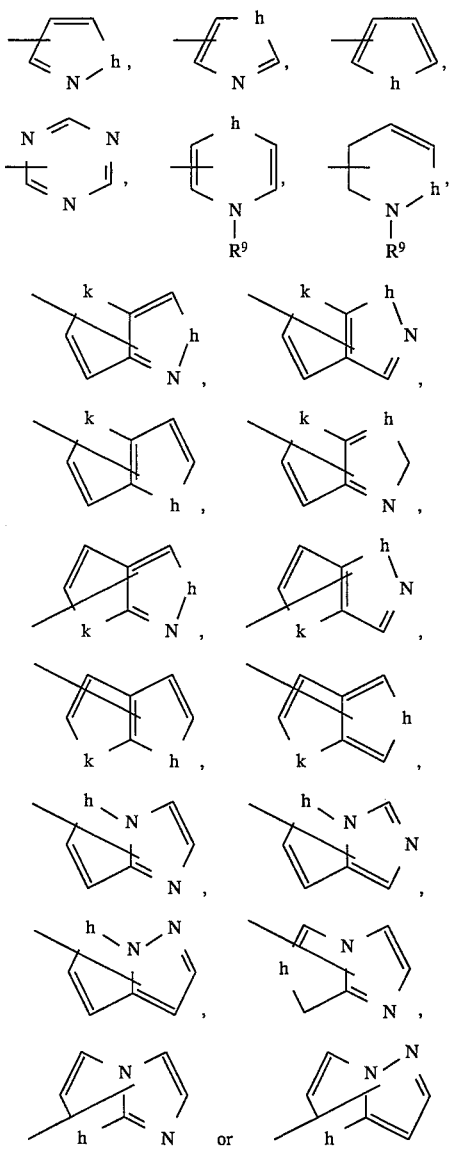

wherein h an k independently stand for —CH₂—, C=O, C=S, S(O)$_m$, N—R⁹, —O—, CH=CH—, —N=CH—, —CH—N—, —CO—N(R⁹)—, —N(R⁹)—CO—, —N=N—, —N(R⁹)—CO—N(R⁹')—, —CH=CH—CO—; wherein R⁹ and R⁹' are independently H or an optionally substituted lower alkyl group and m is an integer of 1 to 2.

20. The compound or a salt thereof as claimed in claim 1, wherein ring A is a group of the class consisting of

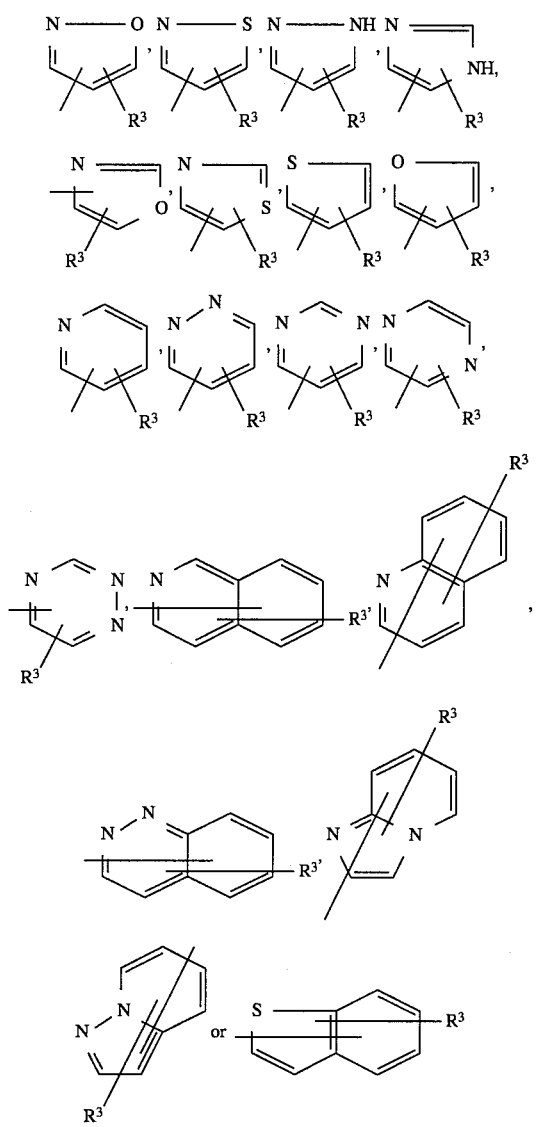

wherein R³ is an optionally esterified or amidated carboxyl, tetrazolyl, trifluoromethanesulfonic amide, phosphoric acid or sulfonic acid group, which may be protected with optionally substituted lower alkyl or acyl.

21. The compound or a salt thereof as claimed in claim 1 or 2, wherein ring A is a group of the class consisting of

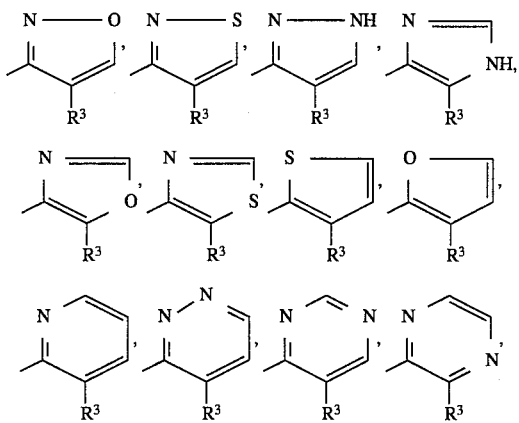

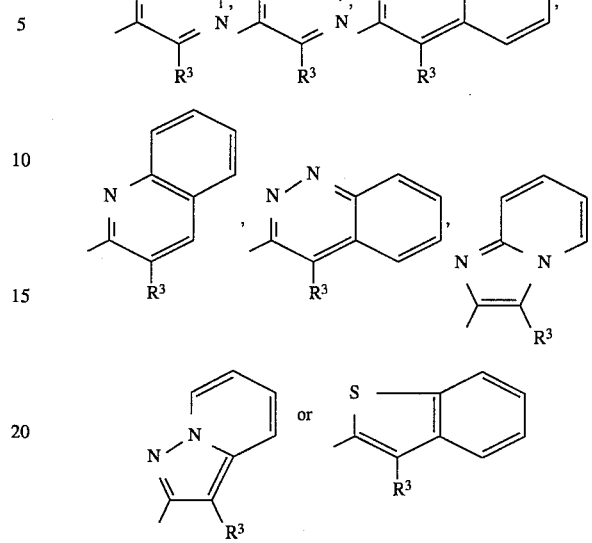

wherein R³ is an optionally esterified or amidated carboxyl, tetrazolyl, trifluoromethanesulfonic amide, phosphoric acid or sulfonic acid group, which may be protected with an optionally substituted lower alkyl or acyl.

22. The compound or a salt thereof as claimed in claim 1, wherein ring A is a group of thiophen, pyrazole, pyridine, pyrimidine, pyrazine, quinoline or isoqunoline skeltone.

23. The compound or a salt thereof as claimed in claim 22, wherein R³ is a group of the formula: —CO—D; wherein D is hydroxy, optionally substituted amino or optionally substituted alkoxy.

24. The compound or a salt thereof as claimed in claim 23, wherein the optionally substituted alkoxy is $C_{1-6}$ alkoxy whose alkyl moiety may be substituted by hydroxy, optionally substituted amino, halogen, $C_{1-6}$ alkoxy, $C_{1-6}$ alkylthio or optionally substituted dioxolenyl, or a group of the formula: —O—CH(R⁴)—OCOR⁵ wherein R⁴ is hydrogen, $C_{1-6}$ alkyl, $C_{2-6}$ alkenyl or $C_{3-8}$ cycloalkyl; and R⁵ is $C_{1-6}$ alkyl, $C_{2-6}$ alkenyl, $C_{3-8}$ cycloalkyl, $C_{1-3}$ alkyl substituted with $C_{3-8}$ cycloalkyl or aryl, $C_{2-3}$ alkenyl optionally substituted with $C_{3-8}$ cycloalkyl or aryl, aryl, $C_{1-6}$ alkoxy, $C_{2-8}$ alkenyloxy, $C_{3-8}$ cycloalkyloxy, $C_{1-3}$ alkoxy substituted with $C_{3-8}$ cycloalkyl or aryl, $C_{2-3}$ alkenyloxy substituted with $C_{3-8}$ cycloalkyl or aryl, or aryloxy.

25. The compound or a salt thereof as claimed in claim 23, wherein R³ is an optionally esterified carboxy group.

26. The compound or a salt thereof as claimed in claim 1, wherein structure of the formula:

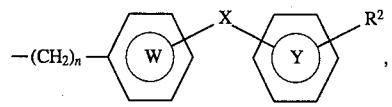

is the structure of the formula:

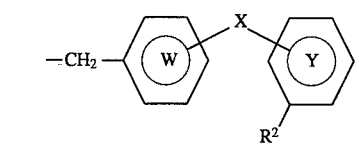

27. The compound or a salt thereof as claimed in claim 1, wherein the formula:

is the structure of the class consisting of

[structures with -CH₂-biphenyl groups bearing various heterocyclic substituents]

28. A compound of the formula (Ia):

wherein
$R^1$ is $C_{1-5}$ alkyl or $C_{1-8}$ alkanoyl, which may be substituted with hydroxy, amino, N—$C_{1-4}$ alkylamino, N,N-di-$C_{1-4}$ alkylamino, halogen, $C_{1-4}$ alkoxy or $C_{1-4}$ alkylthio;

$R^2$ is oxadiazolyl or thiadiazolyl which may be substituted oxo-or thioxo group optionally protected with optionally substituted $C_{1-4}$ alkyl or acyl, and ring A is a group selected from the class consisting of

[various heterocyclic ring structures with $R^3$ substituents]

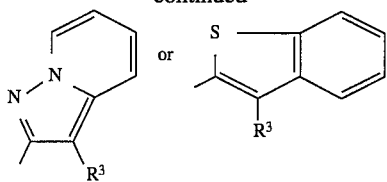

wherein R³ is a group of the formula: —CO—D" wherein D" is hydroxy, amino, N—C$_{1-4}$ alkylamino, N,N-di-C$_{1-4}$ alkylamino or C$_{1-4}$ alkoxy whose alkyl moiety may be substituted by hydroxy, amino, halogen, C$_{2-6}$ alkanoyloxy, 1—C$_{1-6}$ alkoxycarbonyl or C$_{1-4}$ alkoxy, or tetrazolyl optionally protected with C$_{1-4}$ alkyl or acyl.

29. The compound as claimed in claim 1, which is 2-[N-[2'-(2,5-dihydro-5-oxo-1,2,4-oxadiazol-3-yl)biphenyl-4-yl)-[N-propylamino]pyridine-3-carboxylic acid.

30. The compound as claimed in claim 1, which is 2-[N-[2'-(2,5-dihydro-5-oxo-1,2,4-thiadiazol-3-yl)biphenyl-4-yl]methyl-N-propylamino]pyridine-3-carboxylic acid.

31. The compound as claimed in claim 1, which is 2-[N-butyl-N-[2'-(2,5-dihydro-5-oxo-1,2,4-oxadiazol-3-yl-)biphenyl-4-yl]methylamino]pyridine-3-carboxylic acid.

32. Compounds represented by the formula

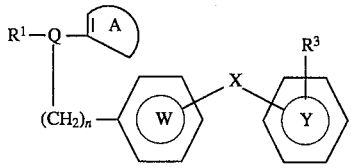

wherein R¹ is a C$_{1-8}$ alkyl, C$_{2-8}$ alkenyl, C$_{2-8}$ alkynyl, C$_{3-6}$ cycloalkyl or C$_{3-6}$ cycloakenyl which may be substituted with hydroxy, amino, N—C$_{1-4}$ alkylamino, N,N-di-C$_{1-4}$ alkylamino, halogen, C$_{1-4}$ alkoxy or C$_{1-4}$ alkylthio, aryl or aralkyl group which may be substituted with halogen, nitro, an optionally substituted amino, C$_{1-4}$ alkoxy, C$_{1-4}$ alkylthio or C$_{1-4}$ alkyl and which may be bound through a group of the formula: —N(R)⁹— wherein R⁹ is hydrogen or an optionally substituted C$_{1-4}$ alkyl group, —O— or —S(O)$_m$— wherein m is an integer of 0 to 2, or a C$_{1-8}$ alkanoyl, C$_{3-8}$ alkenoyl, C$_{3-8}$ alkynoyl, or C$_{4-7}$ cycloalkylcarbonyl group which may be substituted with hydroxyl, amino, N—C$_{1-4}$ alkylamino, N,N-di-C$_{1-4}$ alkylamino, halogen, C$_{1-4}$ alkoxy or C$_{1-4}$ alkylthio group; R² is 2,5-dihydro-5-oxo-1,2,4-oxadiazol-3-yl, 2,5-dihydro-5-oxo-1,2,4-thiadiazol-3-yl or 2,5-dihydro-5-thioxo-1,2,4-oxadiazol-3-yl group, each of which may be substituted with a group of the formula:

1) —CH(R⁴)—OCOR⁵, wherein R⁴ is hydrogen, C$_{1-6}$ alkyl, C$_{2-6}$ alkenyl or C$_{3-8}$ cycloalkyl and R⁵ is C$_{1-6}$ alkyl, C$_{2-6}$ alkenyl, C$_{3-8}$ cycloalkyl, C$_{1-3}$ alkyl substituted with C$_{3-8}$ cycloalkyl, C$_{2-3}$ alkenyl substituted with C$_{3-8}$ cycloalkyl, optionally substituted aryl, C$_{1-6}$ alkoxy, C$_{2-8}$ alkenyloxy, C$_{3-8}$ cycloalkoxy, C$_{1-3}$ alkoxy substituted with C$_{3-8}$ cycloalkyl, C$_{2-3}$ alkenyloxy substituted with C$_{3-8}$ cycloalkyl or optionally substituted aryloxy, 2), an optionally substituted alkyl,
3) acyl,
4) halogen,
5) nitro,
6) cyano,
7) C$_{1-4}$ alkoxy or
8) optionally substituted amino; Q is CH or N; X is a direct bond or a divalent atomic chain having a straight chain of an atomic length of two or less between the ring Y and the ring W, and may have a side chain; rings W and Y are each an aromatic hydrocarbon residue or 4–7 membered hetero-cyclic residue containing one or more of N, S or O, which may be substituted with halogen, nitro, cyano, C$_{1-4}$ alkoxy or an optionally substituted amino group; n is an integer of 1 or 2; the ring A is a 5–8 membered cyclic hydrocarbon residue or heterocyclic ring having at least one unsaturated bound selected from the class consisting of

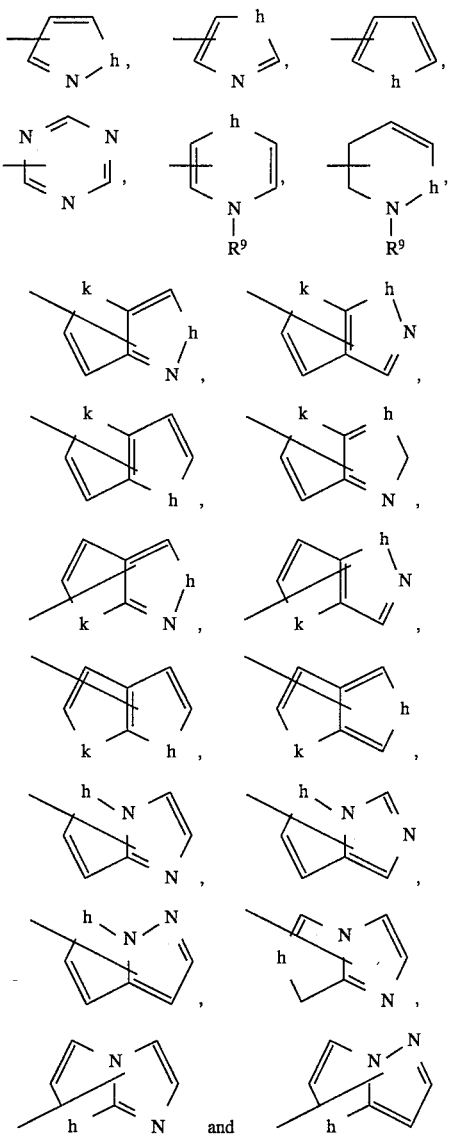

wherein h and k independently stand for

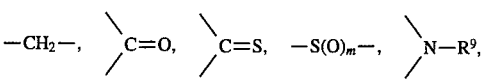

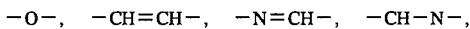

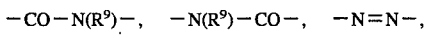

wherein R⁹ and R⁹' are independently H or an optionally substituted C$_{1-4}$ alkyl group and m is an integer of 1 to 2, which may be substituted with 1) an optionally esterified or amidated carboxyl, tetrazolyl, trifluoro-methanesulfonic acid amide, phosphoric acid or sulfonic acid, wherein said groups may be protected with an optionally substituted lower alkyl group or acyl group,
2) halogen,
3) nitro,
4) cyano,
5) optionally substituted amino,
6) a group represented by the formula: —U—$R^6$, wherein U stands for a bond, —O—, —S— or —CO— and $R^6$ stands for hydrogen, an optionally substituted lower alkyl group, or a group represented by the formula: —$(CH_2)_f$—CO—D', wherein D' stands for hydrogen, hydroxyl group, amino, N—$C_{1-4}$ alkylamino, N-N-di-$C_{1-4}$ alkylamino, $C_{1-6}$ alkoxy group whose alkyl moiety is optionally substituted with hydroxyl, optionally substituted amino, halogen, $C_{1-6}$ alkoxy, $C_{1-6}$ alkylthio, optionally substituted dioxolenyl, or a group represented by the formula —O—$CH(R^7)OCOR^8$, wherein $R^7$ stands for hydrogen, $C_{1-6}$ alkyl group or $C_{5-7}$ cycloalkyl group, and $R^8$ stands for $C_{1-6}$ alkyl group, $C_{2-8}$ alkenyl group, $C_{5-7}$ cycloalkyl group, $C_{1-3}$ alkyl group substituted with $C_{5-7}$ cycloalkyl group or aryl group, $C_{2-3}$ alkenyl group substituted with $C_{5-7}$ cycloalkyl or aryl group, optionally substituted aryl group, $C_{1-6}$ alkoxy group, $C_{2-8}$ alkenyloxy group, $C_{5-7}$ cycloalkoxy group, $C_{1-3}$ alkoxy group substituted with $C_{5-7}$ cycloalkyl or aryl group, $C_{2-3}$ alkenyloxy group substituted with $C_{5-7}$ cycloalkyl or aryl group or aryloxy group, and 1 denotes 0 or 2, and two of the substituents are optionally bonded to each other to form a ring; or a salt thereof.

33. A pharmaceutical composition for antagonizing angiotensin II which comprises a therapeutically effective amount of a compound as claimed in claim 1 or a pharmaceutically acceptable salt thereof in admixture with a pharmaceutical acceptable carrier, excipient or diluent.

34. A method for antagonizing angiotensin II in a mammal which comprises administering to said mammal a therapeutically effective amount of a compound as claimed in claim 1 or a pharmaceutically acceptable salt thereof.

* * * * *

UNITED STATES PATENT AND TRADEMARK OFFICE
CERTIFICATE OF CORRECTION

PATENT NO. : 5,500,427  Page 1 of 4
DATED : March 19, 1996
INVENTOR(S) : Keiji KUBO et al.

It is certified that error appears in the above-indentified patent and that said Letters Patent is hereby corrected as shown below:

Col. 63, line 29, change "$-N(R)^9-$" to -- $-N(R^9)-$ --;

line 44, after "aryl" insert --,--.

Col. 64, line 56, change "$R^9$ and are $R^{9'}$" to -- $R^9$ and $R^{9'}$ are--;

line 57, change "1to 2" to --1 to 2--.

Col. 65, line 63, after "hydroxyl" insert --,--.

Col. 66, lines 16-20, delete

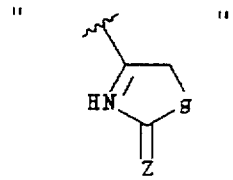

UNITED STATES PATENT AND TRADEMARK OFFICE
CERTIFICATE OF CORRECTION

PATENT NO. : 5,500,427
DATED : March 19, 1996
INVENTOR(S) : Keiji KUBO et al.

It is certified that error appears in the above-indentified patent and that said Letters Patent is hereby corrected as shown below:

and insert

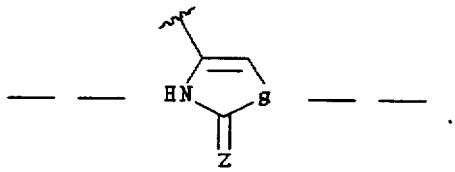

In the Claims:

Claim 19, col. 68, line 14, delete ",";
line 59, delete "h an k" and insert --h and k--; change "C=O" to -->C=O--;
line 60, delete "C-S, S(O)$_m$, N-R$^9$" and insert -->C=S, -S(O)$_m$-, >N-R$^9$--.

Claim 23, col. 70, line 32, change "claim 22" to --claim 20--.

UNITED STATES PATENT AND TRADEMARK OFFICE
CERTIFICATE OF CORRECTION

PATENT NO. : 5,500,427
DATED : March 19, 1996
INVENTOR(S) : Keiji KUBO et al.

It is certified that error appears in the above-indentified patent and that said Letters Patent is hereby corrected as shown below:

Claim 32, col. 73, lines 25-30, delete

"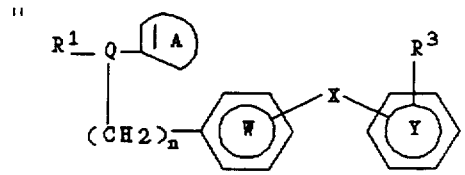"

and insert

-- 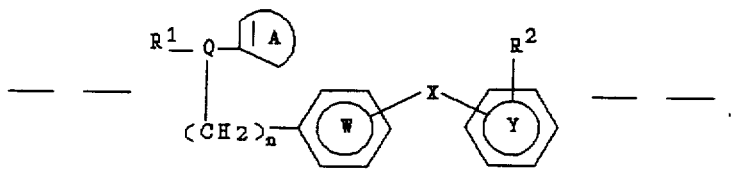 --.

line 40, delete "-N(R)$^9$-" and insert -- -N($R^9$)- --;

UNITED STATES PATENT AND TRADEMARK OFFICE
CERTIFICATE OF CORRECTION

PATENT NO. : 5,500,427
DATED : March 19, 1996
INVENTOR(S) : Keiji Kubo, et al

It is certified that error appears in the above-indentified patent and that said Letters Patent is hereby corrected as shown below:

Col. 74, line 60, delete " -CH-N-" and insert -- -CH=N- --.

Signed and Sealed this

Tenth Day of December, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,500,427
DATED : March 19, 1996
INVENTOR(S) : Keiji KUBO et al.

It is certified that error appears in the above-indentified patent and that said Letters Patent is hereby corrected as shown below:

Please note that Column 66, lines 16-20, contains a typographical error wherein

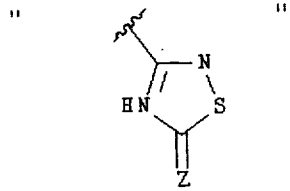

should read

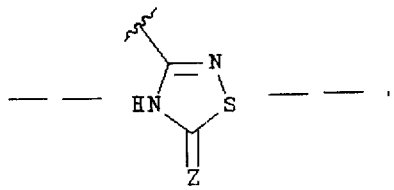

UNITED STATES PATENT AND TRADEMARK OFFICE
CERTIFICATE OF CORRECTION

PATENT NO. : 5,500,427
DATED : March 19, 1996
INVENTOR(S) : Keiji KUBO et al.

It is certified that error appears in the above-indentified patent and that said Letters Patent is hereby corrected as shown below:

Claim 19, column 68, line 60, delete "C=S, S(O)$_m$, N-R$^9$" and insert -->C=S, -S(O)$_m$-, >N-R$^9$--.

Signed and Sealed this

Twenty-first Day of October 1997

Attest:

BRUCE LEHMAN

Attesting Officer

Commissioner of Patents and Trademarks